US010227591B2

(12) United States Patent
Kowalik et al.

(10) Patent No.: US 10,227,591 B2
(45) Date of Patent: Mar. 12, 2019

(54) MODULATION OF HUMAN CYTOMEGALOVIRUS REPLICATION BY MICRO-RNA 132 (MIR132), MICRO-RNA 145 (MIR145) AND MICRO-RNA 212 (MIR212)

(71) Applicant: University of Massachusetts, Boston, MA (US)

(72) Inventors: Timothy F. Kowalik, Princeton, MA (US); Mariluz Rodriguez-Gonzalez, Worcester, MA (US); Alexander Lagadinos, Worcester, MA (US)

(73) Assignee: University of Massachusetts, Boston, MA (US)

( * ) Notice: Subject to any disclaimer, the term of this patent is extended or adjusted under 35 U.S.C. 154(b) by 0 days.

(21) Appl. No.: 15/383,600

(22) Filed: Dec. 19, 2016

(65) Prior Publication Data

US 2017/0101640 A1 Apr. 13, 2017

Related U.S. Application Data

(60) Division of application No. 14/563,512, filed on Dec. 8, 2014, now Pat. No. 9,562,232, which is a division of application No. 13/227,117, filed on Sep. 7, 2011, now Pat. No. 8,933,045, which is a continuation of application No. PCT/US2010/027040, filed on Mar. 11, 2010.

(60) Provisional application No. 61/159,420, filed on Mar. 11, 2009, provisional application No. 61/159,391, filed on Mar. 11, 2009.

(51) Int. Cl.

| | |
|---|---|
| ***C12N 15/113*** | (2010.01) |
| ***A61K 31/522*** | (2006.01) |
| ***A61K 31/7105*** | (2006.01) |
| ***A61K 35/50*** | (2015.01) |
| ***A61K 45/06*** | (2006.01) |
| ***C12Q 1/70*** | (2006.01) |
| ***G01N 33/569*** | (2006.01) |

(52) U.S. Cl.

CPC ........ *C12N 15/1133* (2013.01); *A61K 31/522* (2013.01); *A61K 31/7105* (2013.01); *A61K 35/50* (2013.01); *A61K 45/06* (2013.01); *C12N 15/1131* (2013.01); *C12Q 1/705* (2013.01); *G01N 33/56994* (2013.01); *C12N 2310/11* (2013.01); *C12N 2310/113* (2013.01); *C12N 2310/14* (2013.01); *C12N 2310/141* (2013.01); *C12N 2310/315* (2013.01); *C12N 2320/31* (2013.01); *C12Q 2600/158* (2013.01); *C12Q 2600/178* (2013.01); *G01N 2333/03* (2013.01)

(58) Field of Classification Search

CPC ............ A01K 2207/05; C12N 15/1133; C12N 2310/11; C12N 2310/113; C12N 2310/14

See application file for complete search history.

(56) References Cited

U.S. PATENT DOCUMENTS

| | | | | |
|---|---|---|---|---|
| 8,933,045 | B2 | 1/2015 | Kowalik et al. | |
| 9,562,232 | B2 | 2/2017 | Kowalik et al. | |
| 2009/0156535 | A1* | 6/2009 | Vanicek | G06F 19/18 514/44 R |
| 2011/0151430 | A1 | 6/2011 | Kowalik et al. | |

FOREIGN PATENT DOCUMENTS

| | | | |
|---|---|---|---|
| WO | WO-04/071430 | A2 | 8/2004 |
| WO | WO-05/118806 | A2 | 12/2005 |
| WO | WO-08/127587 | A2 | 10/2008 |
| WO | WO-09/033185 | A1 | 3/2009 |
| WO | WO2009/033185 | A1 * | 3/2009 |

OTHER PUBLICATIONS

Moon et al. Trends in Cell Biology 13:13-22 (Year: 2003).*
Leoh et al. Mol. Cancer Res. 10, pp. 376-391 (Year: 2012).*
Swaminathan et al. J. Mol. Biol. 426, 1178-1197 (Year: 2014).*
Tocci, et. al., "Effects of the Nucleoside Analog 2'-Nor2' Dexyguanosine on Human Cytomegalovrius Replication" Antimicrobial Agents and Chemotherapy, 1984, 25(2):247-252.
Grey et al., "Identification and function of human cytomegalovirus microRNAs" Journal of Clinical Virology, 2008, 41:186-191.
Wang et al. "Human Cytomegalovirus Infection Alters the Expression of Cellular MicroRNA Species That Affect Its Replication" Journal of Virology, 2008, 82(18):9065-9074.
International Preliminary Report on Patentability issued in Application No. PCT/US2010/027040, dated Sep. 13, 2011.
International Search Report issued in Application No. PCT/US2010/027040, dated Feb. 11, 2011.
Written Opinion issued in Application No. PCT/US2010/027040, dated Sep. 11, 2011.

* cited by examiner

*Primary Examiner* — Brian Whiteman
(74) *Attorney, Agent, or Firm* — McCarter & English, LLP

(57) ABSTRACT

The present invention relates to miR145, miR132, miR212, and the genes or gene products regulated by these miRNAs. miR145 is downregulated in cells infected with HCMV. This downregulation modulates expression of miR145 target genes, including IRS-1. Transfection of cells with a miR145 agent, such as a miR145 mimetic, reduces HCMV replication and protein expression. miR132 and miR212 are upregulated in cells infected with HCMV. This upregulation modulates expression of miR132 and miR212 target genes, including MeCP2 and RICS. Transfection of cells with a miR132 and/or a miR212 antagonist reduces HCMV replication and protein expression. Accordingly, the invention provides methods of attenuating HCMV replication by modulating, for example, miR145, miR132, and/or miR212, and targets thereof. Also provided are methods of detecting an HCMV infection, and compositions and kits useful for attenuating HCMV replication.

26 Claims, 29 Drawing Sheets

Specification includes a Sequence Listing.

| Sample | ΔΔCT | Fold Change |
|---|---|---|
| miR-145 – 24 hpi | 1.003 | -2.00416321 |
| miR-145 – 48 hpi | 1.612667 | -3.058166594 |
| miR-145 – 72 hpi | 1.581667 | -2.99315502 |
| miR-145 – 96 hpi | 0.068667 | -1.04874723 |

Homo sapiens miR-145 stem-loop (SEQ ID NO: 1)

```
5' c   u  u      c  uc    u  c          uagau
    acc ug ccuca gg  cagu uu ccaggaaucccu     g
    ||| || ||||| ||  |||| || ||||||||||||     c
    ugg ac ggagu uc  guca aa gguccuuagggg     u
3' u   u  u      -  uu    u  a          uagaa
```

Homo sapiens miR145 mature (processed) (SEQ ID NO: 2)

5' guccaguuuucccaggaaucccu 3'

Homo sapiens miR-132 stem-loop (SEQ ID NO: 3)

```
5'c    cccc     -  c a     a           uuc            --gu g
  cgc     gcgu cu c gggc accguggcu   gauuguuacu     g g
  |||     |||| || | |||| |||||||||   ||||||||||     |
  gcg     cgca ga g cccg ugguaccga   cugacaaugg     c a
3'c    cacc     c  c c     c           cau            aggu a
```

*Fig. 20A*

Homo sapiens miR132 mature (processed) (SEQ ID NO: 4)

5' UAACAGUCUACAGCCAUGGUCG 3'

*Fig. 20B*

Homo sapiens miR-212 stem-loop (SEQ ID NO: 5)

```
5'cggggcaccccgccccgga   c   c   -ca  u     cu      c      ccc
                     cag gcg cgg   cc uggcu  agacug uuacug   gggc
                     ||| ||| |||   || |||||  |||||| ||||||   ||| c
                     guc cgc cgg   gg acuga  ucugac aaugac   cccg
3'----------ccgccccg   -   a   acc  c     cc      -      --u
```

*Fig. 20C*

Homo sapiens miR212 mature (processed) (SEQ ID NO: 6)

5' uaacagucuccagucacggcc 3'

*Fig. 20D*

IRS-1 (SEQ ID NO: 7; gi187761322)

GGTTGTTTTTCGGAGCCTCCCTCTGCTCAGCGTTGGTGGTGGCGGTGGCAGCATGGCGAGCCCTCCGGAGAGCGATGGC
TTCTCGGACGTGCGCAAGGTGGGCTACCTGCGCAAACCCAAGAGCATGCACAAACGCTTCTTCGTACTGCGCGCGGCCA
GCGAGGCTGGGGGCCCGGCGCGCCTCGAGTACTACGAGAACGAGAAGAAGTGGCGGCACAAGTCGAGCGCCCCCAAAC
GCTCGATCCCCCTTGAGAGCTGCTTCAACATCAACAAGCGGGCTGACTCCAAGAACAAGCACCTGGTGGCTCTCTACACC
CGGGACGAGCACTTTGCCATCGCGGCGGACAGCGAGGCCGAGCAAGACAGCTGGTACCAGGCTCTCCTACAGCTGCACA
ACCGTGCTAAGGGCCACCACGACGGAGCTGCGGCCCTCGGGGCGGGAGGTGGTGGGGGCAGCTGCAGCGGCAGCTCC
GGCCTTGGTGAGGCTGGGGAGGACTTGAGCTACGGTGACGTGCCCCCAGGACCCGCATTCAAAGAGGTCTGGCAAGTGA
TCCTGAAGCCCAAGGGCCTGGGTCAGACAAAGAACCTGATTGGTATCTACCGCCTTTGCCTGACCAGCAAGACCATCAGC
TTCGTGAAGCTGAACTCGGAGGCAGCGGCCGTGGTGCTGCAGCTGATGAACATCAGGCGCTGTGGCCACTCGGAAAACT
TCTTCTTCATCGAGGTGGGCCGTTCTGCCGTGACGGGGCCCGGGGAGTTCTGGATGCAGGTGGATGACTCTGTGGTGGC
CCAGAACATGCACGAGACCATCCTGGAGGCCATGCGGGCCATGAGTGATGAGTTCCGCCCTCGCAGCAAGAGCCAGTCC
TCGTCCAACTGCTCTAACCCCATCAGCGTCCCCCTGCGCCGGCACCATCTCAACAATCCCCCGCCCAGCCAGGTGGGGCT
GACCCGCCGATCACGCACTGAGAGCATCACCGCCACCTCCCCGGCCAGCATGGTGGGCGGGAAGCCAGGCTCCTTCCGT
GTCCGCGCCTCCAGTGACGGCGAAGGCACCATGTCCCGCCCAGCCTCGGTGGACGGCAGCCCTGTGAGTCCCAGCACCA
ACAGAACCCACGCCCACCGGCATCGGGGCAGCGCCCGGCTGCACCCCCCGCTCAACCACAGCCGCTCCATCCCCATGCC
GGCTTCCCGCTGCTCGCCTTCGGCCACCAGCCCGGTCAGTCTGTCGTCCAGTAGCACCAGTGGCCATGGCTCCACCTCG
GATTGTCTCTTCCCACGGCGATCTAGTGCTTCGGTGTCTGGTTCCCCCAGCGATGGCGGTTTCATCTCCTCGGATGAGTAT
GGCTCCAGTCCCTGCGATTTCCGGAGTTCCTTCCGCAGTGTCACTCCGGATTCCCTGGGCCACACCCCACCAGCCCGCGG
TGAGGAGGAGCTAAGCAACTATATCTGCATGGGTGGCAAGGGGCCCTCCACCCTGACCGCCCCCAACGGTCACTACATTT
TGTCTCGGGGTGGCAATGGCCACCGCTGCACCCCAGGAACAGGCTTGGGCACGAGTCCAGCCTTGGCTGGGGATGAAGC
AGCCAGTGCTGCAGATCTGGATAATCGGTTCCGAAAGAGAACTCACTCGGCAGGCACATCCCCTACCATTACCCACCAGA
AGACCCCGTCCCAGTCCTCAGTGGCTTCCATTGAGGAGTACACAGAGATGATGCCTGCCTACCCACCAGGAGGTGGCAGT
GGAGGCCGACTGCCGGGACACAGGCACTCCGCCTTCGTGCCCACCCGCTCCTACCCAGAGGAGGGTCTGGAAATGCACC
CCTTGGAGCGTCGGGGGGGGCACCACCGCCCAGACAGCTCCACCCTCCACACGGATGATGGCTACATGCCCATGTCCCC
AGGGGTGGCCCCAGTGCCCAGTGGCCGAAAGGGCAGTGGAGACTATATGCCCATGAGCCCCAAGAGCGTATCTGCCCCA
CAGCAGATCATCAATCCCATCAGACGCCATCCCCAGAGAGTGGACCCCAATGGCTACATGATGATGTCCCCCAGCGGTGG
CTGCTCTCCTGACATTGGAGGTGGCCCCAGCAGCAGCAGCAGCAGCAGCAACGCCGTCCCTTCCGGGACCAGCTATGGA
AAGCTGTGGACAAACGGGGTAGGGGGCCACCACTCTCATGTCTTGCCTCACCCCAAACCCCCAGTGGAGAGCAGCGGTG
GTAAGCTCTTACCTTGCACAGGTGACTACATGAACATGTCACCAGTGGGGGACTCCAACACCAGCAGCCCCTCCGACTGC
TACTACGGCCCTGAGGACCCCCAGCACAAGCCAGTCCTCTCCTACTACTCATTGCCAAGATCCTTTAAGCACACCCAGCGC
CCCGGGGAGCCGGAGGAGGGTGCCCGGCATCAGCACCTCCGCCTTTCCACTAGCTCTGGTCGCCTTCTCTATGCTGCAA
CAGCAGATGATTCTTCCTCTTCCACCAGCAGCGACAGCCTGGGTGGGGGATACTGCGGGGCTAGGCTGGAGCCCAGCCT
TCCACATCCCCACCATCAGGTTCTGCAGCCCCATCTGCCTCGAAAGGTGGACACAGCTGCTCAGACCAATAGCCGCCTGG
CCCGGCCCACGAGGCTGTCCCTGGGGGATCCCAAGGCCAGCACCTTACCTCGGGCCCGAGAGCAGCAGCAGCAGCAGC
AGCCCTTGCTGCACCCTCCAGAGCCCAAGAGCCCGGGGGAATATGTCAATATTGAATTTGGGAGTGATCAGTCTGGCTAC
TTGTCTGGCCCGGTGGCTTTCCACAGCTCACCTTCTGTCAGGTGTCCATCCCAGCTCCAGCCAGCTCCCAGAGAGGAAGA
GACTGGCACTGAGGAGTACATGAAGATGGACCTGGGGCCGGGCCGGAGGGCAGCCTGGCAGGAGAGCACTGGGGTCGA
GATGGGCAGACTGGGCCCTGCACCTCCCGGGGCTGCTAGCATTTGCAGGCCTACCCGGGCAGTGCCCAGCAGCCGGGG
TGACTACATGACCATGCAGATGAGTTGTCCCCGTCAGAGCTACGTGGACACCTCGCCAGCTGCCCCTGTAAGCTATGCTG
ACATGCGAACAGGCATTGCTGCAGAGGAGGTGAGCCTGCCCAGGGCCACCATGGCTGCTGCCTCCTCATCCTCAGCAGC
CTCTGCTTCCCCGACTGGGCCTCAAGGGGCAGCAGAGCTGGCTGCCCACTCGTCCCTGCTGGGGGGCCCACAAGGACCT
GGGGGCATGAGCGCCTTCACCCGGGTGAACCTCAGTCCTAACCGCAACCAGAGTGCCAAAGTGATCCGTGCAGACCCAC
AAGGGTGCCGGCGGAGGCATAGCTCCGAGACTTTCTCCTCAACACCCAGTGCCACCCGGGTGGGCAACACAGTGCCCTT
TGGAGCGGGGGCAGCAGTAGGGGGCGGTGGCGGTAGCAGCAGCAGCAGCGAGGATGTGAAACGCCACAGCTCTGCTTC
CTTTGAGAATGTGTGGCTGAGGCCTGGGGAGCTTGGGGGAGCCCCCAAGGAGCCAGCCAAACTGTGTGGGGCTGCTGG
GGGTTTGGAGAATGGTCTTAACTACATAGACCTGGATTTGGTCAAGGACTTCAAACAGTGCCCTCAGGAGTGCACCCCTGA
ACCGCAGCCTCCCCCACCCCCACCCCCTCATCAACCCCTGGGCAGCGGTGAGAGCAGCTCCACCCGCCGCTCAAGTGAG
GATTTAAGCGCCTATGCCAGCATCAGTTTCCAGAAGCAGCCAGAGGACCGTCAGTAGCTCAACTGGACATCACAGCAGAA
TGAAGACCTAAATGACCTCAGCAAATCCTCTTCTAACTCATGGGTACCCAGACTCTAAATATTTCATGATTCACAACTAGGA
CCTCATATCTTCCTCATCAGTAGATGGTACGATGCATCCATTTCAGTTTGTTTACTTTATCCAATCCTCAGGATTTCATTGAC
TGAACTGCACGTTCTATATTGTGCCAAGCGAAAAAAAAAAAATGCACTGTGACACCAGAATAATGAGTCTGCATAAACTTCAT
CTTCAACCTTAAGGACTTAGCTGGCCACAGTGAGCTGATGTGCCCACCACCGTGTCATGAGAGAATGGGTTTACTCTCAAT
GCATTTTCAAGATACATTTCATCTGCTGCTGAAACTGTGTACGACAAAGCATCATTGTAAATTATTTCATACAAAACTGTTCA
CGTTGGGTGGAGAGAGTATTAAATATTTAACATAGGTTTTGATTTATATGTGTAATTTTTTAAATGAAAATGTAACTTTTCTTA
CAGCACATCTTTTTTTTGGATGTGGATGGAGGTATACAATGTTCTGTTGTAAAGAGTGGAGCAAATGC

IRS-1 (SEQ ID NO: 7; gi187761322) *(continued)*

TTAAAACAAGGCTTAAAAGAGTAGAATAGGGTATGATCCTTGTTTTAAGATTGTAATTCAGAAAACATAATATAAGAATCATAGTG
CCATAGATGGTTCTCAATTGTATAGTTATATTTGCTGATACTATCTCTTGTCATATAAACCTGATGTTGAGCTGAGTTCCTTATAA
GAATTAATCTTAATTTTGTATTTTTTCCTGTAAGACAATAGGCCATGTTAATTAAACTGAAGAAGGATATATTTGGCTGGGTGTTTT
CAAATGTCAGCTTAAAATTGGTAATTGAATGGAAGCAAAATTATAAGAAGAGGAAATTAAAGTCTTCCATTGCATGTATTGTAAAC
AGAAGGAGATGGGTGATTCCTTCAATTCAAAAGCTCTCTTTGGAATGAACAATGTGGGCGTTTGTAAATTCTGGAAATGTCTTTC
TATTCATAATAAACTAGATACTGTTGATCTTTTCTTCTGTCCCCTCCCCCCACCACTTCTGTAAGTTTCCTGCTCTATTCCCACCA
TTTTTTTCTGTGCACACATTATGATATATTTCATTTCCTGCATTGTCTTGAGAAAGATGGTAAGGCAAGTGAGCTGTTGCTAACCA
GAAATTAAAATTCCAGTAAGTGTTTTTCATTATGACCAGGGCTATGTGTCACCTTCCCTAAGACTCTTACCTTATCTCATATTTTTT
GAGAACTTCCAGTGTTACATTATTTAACTGAATGTAATTGGCCCATTTGCCTTGGTGGGTGCTGGCCTATTAGTGATTAGTTAAC
AAAACACAGCGTACAGAGAGCACAGAAAAGCTTAATGACCTGCTACTGAAACACCTAGCCAGCAGTGAAAATGTTAATTCTTTTC
TTGTTTGGAAAGTATACACGTCTTGGAATTTTTTCCACGTGAAAAACAAATGGCAATGAATGCATTTAAAGATATTGCCGACAGAT
TTTTAAATCTTTTTACCAGGAAACTTCCTAAAGGTTAAATGAATTAATGCAAATATCAGGCTCCCTCTGAGTCTGTGGGAGCCTCT
ATCTCTCTATCAGGAATTCGCATCCCTACTATTGGGAGGAGCAACATTTTATTTCTCTGAACGCCTAAGCTCCCTGGGTGGGAG
TGGGGACTACAAGGTAGGGGCCAGGGTTGGAGGGCATTGTAGTGGCTGCTGCCTCCTGATGAACTGTTTGGGGACCCCAGCT
CTACTCAAAAGGGAGCGGAGATAAATGGAACCCCTCACACTGCTGAGGCCCGTGTTACTGTTCATTCAGCCAGGTGGCATGTA
CCTCACAGACTGTTGTGCAGTGTCCGTTATTGCAGATTTTAATCATTTGCATGCTCATCAATTTCTAAGATAAATAGGGTCTAGA
GTCATAAGAATCCATTGTTTTCAAGGAACTTGCAGAATTACATCATTTCCTATTAGTAGAGAGCACTACCCATTTTGAAAATCTGA
TATGAAAGTTGTTTTTTACTCTTGTAAAAAAAGACTTTCTTAGTCAAACTAACTTTTCATATTTTCAAGCATTCTGATTCATACTCTT
GCTAGTGGAAGAAGAGAGCAAGCTGCCCTGCTCTTTTCCTTTGAGGACTGAAATAGTTAAAGAGAAATCAATGAACAAAGTCAC
TCCCAACCATTTTCCTGTAAAGCTGGTTATTATTTCTCAAGGAACCTACACTTTGAATATGTGTTACCGAGATACCTCTACATGTG
GAATTATCAACATGTTTTGAATGAGAGCAGAAATGAACAGACTGGAAAAATCTATCTCTTGGTTTCTATTTCTCTGACTTTTTGAG
TCGAAAAGCATAAAGGTAGAAATTCTTATTTAAGCTGCTTCTAGTGGTGCCTGAGCTGGTTTTGATGGTGGCATCAAACTACCGA
TTTAAAACTGGAAGTTGCTGGTACTCAAACCAAAAGTTCATACTCTGGCGACACGAAGGGTTTCCTTTGAGCAACGTCAGCTGC
TGAGTCCTTGTGTTCAGTTCCCATTGAGGAGAGTTGGCTTTTATCCATTTCAAAGCATTTGTAGGCCAGCCAAGGGCTTTCATTA
TTGAGGCTTCTAGTGGCCTCTGGTTAACCTAGAAGTTAGTGGGTTTTTCTTGATGACACCAACCTCTCACAGCGTTTTTCCTTAG
AGACTTAAGCAGAGTTTTAAAATCCTCTTTTGCGAAAAGAACAAATATGTTTTATGACTTTGATGATATCTTCATTCTGGGCAAAA
GAATGGCCCTAGAACCAGCTAGAAGTGAAGAGAATCCATTAATGATCAACCACCTGAGTCAATAATGAGAAATCAGTACTGATG
TTACATTTGTGGCTATTTCTTGCTGACTTTCAAAGGTCAAGGACTCTTGACTAATCCAGTGACTGCAAAAATGGATCTACTAAAAG
TCATCTAGCCAGAAGTAGAGATTTTTAACCTTTCTTTCCCTGGCTTTTGTCTTCTAGCTATCATTTAAATTTGAGACATTTGAAGTA
TTAAGAAACAATTTTTCTGTATGGTAAGAAACAGTATTTTACAATACTGAAGCCCTGTTTTATTCAATCTTGCATCTTGAATACAAT
ATACCACAAAGTCGGAAACTTTATATTTATTTACTGCAGGTGGTTAAAAAAAGGGGGGAAAGGGTTTCACCATCCACTGACAACG
AGAGCCATGACAAATAGTATCCATGTGCAGTCTTCCAACTGCTGGTGACAATGACCCCATATTTGGTCTCATGCTGCTTTTGCA
GAGCACTCTGTAGGTTAGTCCATCACACAAGGAGGCCCTGAATCCAGACACTGTGAATTAAGACCTTGGCGGGGAGAGATGTG
ACCCTTTTGGTAGGAATGGGAAGAAGAATGGGTGGAAGCCAATATGAAATTTCTTCTTTGCAATGACTTGACAGGGGAGTTAAT
GTTCCTAGGATGCCATGAATGATGAATGTTAGTTGGAGGTAATGCTGTATATGTGTGTGTGTGTGTGTGTGTGTGTTTGTGTGT
GTGTATATATATGTGTGTGTGTATATATATGTGACATGTGTGTGTCTTTGTGTGTGTGTATATATATGTGACGTGTGTGTGGGATG
TGTGTGTGTATATATAGATGAATATATACAAATATATAGATATATACACACATATATAGATATATATACACATATATAGATATATATA
CACACATATATAGATACACATATGTGTGTGTGTGTATATATATATATATATATATATAGATGTATAGGCTTGTGAGAAACTTGAGA
GGAAGAAGCATGCTCTTCTAGGAATGTGAGGAAATATGACCTTGCCAAGACTAAAAGACCTCTAGACTGTGAGCTCAGTTATGG
AGAACAAAAACAGCTTCATAGTGAGTAGAACACCGAGGATAAACACTGGGGCCATGGGTCCTTTCTGAGGCAGCGCCACAGAA
GATCTTTGTGGTCCTTCCGTAGTTCTGTAAGTCTGTCTCCTAAGTATGGGTAGAGAATATGTAGCCTGTTGTGTGTCTCCCACTA
CTTGTAAACAGAGCATCACATTAGGGGCAGGGAGGAGGTGGAATGATATTGGAGGTGCTTAACCCTACTCGAGGAATTAATTAT
GAATAAAGAGCTTATAATTAGCTAACATGACTAGAAAACACATGACTTAGGTGGAGAGTTAGCTTTCTTTTCTAGTTTGTGTATGA
CTTGCCATTTGTGACGTATACACCAAAAGATCTGGTGTTTTAGACTTCTGCCATTCACTTGGCATTTAAATCTCTCTTTGCTTATG
CTGTTAACGAGTATGCCATAGGATAGGACAAATTCAGTAAACAGGAAAACTTGTCCATATTTGCATAGACATTTGTAGGGTTTTTT
TTTTCTTTTTCTTTTTAGAACTTCACCATTGGCTTAAGAATGTAGTTCCCAAAACAATTTTTTCTTGCAAAGTACTTTCCTTACACC
TCTTGGCTACAGGGTGGGCCAAATTAAACATATATGTATTTTCATTTAATGTATGTGCAGTTTGGTTTATCATCTTAAGATGGTGG
TGCTGCCCCGGTGCTACTTCATCTGTGTACACAAAGACCAATGCATGGTCTGTATTGCTACCAAAACATTTACTGTATATATGTT
TATAACATGTATTATGTATATATGTAATGGGTGCCAGGCCAGGTATATATTTTTTATTTAGAAGTGTTTCACTTTTCCAAGTTTTCT
TTATAGTGTTATGCTTATTTTCAATTTTTTTTTTCCTGATTCTGTCTGGTACTTAGAATTGTAGTGTCTTCATCATCAATTAAAGAAA
ACTGTCTAAATGAATTCATGGATGTAAATATTAGTGGTCCTTAATGTCTTTGATTGCTGGACATGAAACAAACTGCCAATTAAATT
TTGCGGAGACAAAAAAAA

*Fig. 21B*

MAPK (SEQ ID NO: 8; gi75709178)

GCCCCTCCCTCCGCCCGCCCGCCGGCCCGCCCGTCAGTCTGGCAGGCAGGCAGGCAATCGGTCCGAGTGGCTGTCGG
CTCTTCAGCTCTCCCGCTCGGCGTCTTCCTTCCTCCTCCCGGTCAGCGTCGGCGGCTGCACCGGCGGCGGCGCAGTCC
CTGCGGGAGGGGCGACAAGAGCTGAGCGGCGGCCGCCGAGCGTCGAGCTCAGCGCGGCGGAGGCGGCGGCGGCCC
GGCAGCCAACATGGCGGCGGCGGCGGCGGCGGGCGCGGGCCCGGAGATGGTCCGCGGGCAGGTGTTCGACGTGGG
GCCGCGCTACACCAACCTCTCGTACATCGGCGAGGGCGCCTACGGCATGGTGTGCTCTGCTTATGATAATGTCAACAAA
GTTCGAGTAGCTATCAAGAAAATCAGCCCCTTTGAGCACCAGACCTACTGCCAGAGAACCCTGAGGGAGATAAAAATCTT
ACTGCGCTTCAGACATGAGAACATCATTGGAATCAATGACATTATTCGAGCACCAACCATCGAGCAAATGAAAGATGTAT
ATATAGTACAGGACCTCATGGAAACAGATCTTTACAAGCTCTTGAAGACACAACACCTCAGCAATGACCATATCTGCTATT
TTCTCTACCAGATCCTCAGAGGGTTAAAATATATCCATTCAGCTAACGTTCTGCACCGTGACCTCAAGCCTTCCAACCTGC
TGCTCAACACCACCTGTGATCTCAAGATCTGTGACTTTGGCCTGGCCCGTGTTGCAGATCCAGACCATGATCACACAGG
GTTCCTGACAGAATATGTGGCCACACGTTGGTACAGGGCTCCAGAAATTATGTTGAATTCCAAGGGCTACACCAAGTCCA
TTGATATTTGGTCTGTAGGCTGCATTCTGGCAGAAATGCTTTCTAACAGGCCCATCTTTCCAGGGAAGCATTATCTTGACC
AGCTGAACCACATTTTGGGTATTCTTGGATCCCCATCACAAGAAGACCTGAATTGTATAATAAATTTAAAAGCTAGGAACT
ATTTGCTTTCTCTTCCACACAAAAATAAGGTGCCATGGAACAGGCTGTTCCCAAATGCTGACTCCAAAGCTCTGGACTTAT
TGGACAAAATGTTGACATTCAACCCACACAAGAGGATTGAAGTAGAACAGGCTCTGGCCCACCCATATCTGGAGCAGTA
TTACGACCCGAGTGACGAGCCCATCGCCGAAGCACCATTCAAGTTCGACATGGAATTGGATGACTTGCCTAAGGAAAAG
CTCAAAGAACTAATTTTTGAAGAGACTGCTAGATTCCAGCCAGGATACAGATCTTAAATTTGTCAGGACAAGGGCTCAGA
GGACTGGACGTGCTCAGACATCGGTGTTCTTCTTCCCAGTTCTTGACCCCTGGTCCTGTCTCCAGCCCGTCTTGGCTTAT
CCACTTTGACTCCTTTGAGCCGTTTGGAGGGGCGGTTTCTGGTAGTTGTGGCTTTTATGCTTTCAAAGAATTTCTTCAGTC
CAGAGAATTCCTCCTGGCAGCCCTGTGTGTGTCACCCATTGGTGACCTGCGGCAGTATGTACTTCAGTGCACCTACTGC
TTACTGTTGCTTTAGTCACTAATTGCTTTCTGGTTTGAAAGATGCAGTGGTTCCTCCCTCTCCTGAATCCTTTTCTACATGA
TGCCCTGCTGACCATGCAGCCGCACCAGAGAGAGATTCTTCCCCAATTGGCTCTAGTCACTGGCATCTCACTTTATGATA
GGGAAGGCTACTACCTAGGGCACTTTAAGTCAGTGACAGCCCCTTATTTGCACTTCACCTTTTGACCATAACTGTTTCCC
CAGAGCAGGAGCTTGTGGAAATACCTTGGCTGATGTTGCAGCCTGCAGCAAGTGCTTCCGTCTCCGGAATCCTTGGGGA
GCACTTGTCCACGTCTTTTCTCATATCATGGTAGTCACTAACATATATAAGGTATGTGCTATTGGCCCAGCTTTTAGAAAA
TGCAGTCATTTTTCTAAATAAAAAGGAAGTACTGCACCCAGCAGTGTCACTCTGTAGTTACTGTGGTCACTTGTACCATAT
AGAGGTGTAACACTTGTCAAGAAGCGTTATGTGCAGTACTTAATGTTTGTAAGACTTACAAAAAAAGATTTAAAGTGGCAG
CTTCACTCGACATTTGGTGAGAGAAGTACAAAGGTTGCAGTGCTGAGCTGTGGGCGGTTTCTGGGGATGTCCCAGGGTG
GAACTCCACATGCTGGTGCATATACGCCCTTGAGCTACTTCAAATGTGGGTGTTTCAGTAACCACGTTCCATGCCTGAGG
ATTTAGCAGAGAGGAACACTGCGTCTTTAAATGAGAAAGTATACAATTCTTTTTCCTTCTACAGCATGTCAGCATCTCAAG
TTCATTTTTCAACCTACAGTATAACAATTTGTAATAAAGCCTCCAGGAGCTCATGACGTGAAGCACTGTTCTGTCCTCAAG
TACTCAAATATTTCTGATACTGCTGAGTCAGACTGTCAGAAAAAGCTAGCACTAACTCGTGTTTGGAGCTCTATCCATATT
TTACTGATCTCTTTAAGTATTTGTTCCTGCCACTGTGTACTGTGGAGTTGACTCGGTGTTCTGTCCCAGTGCGGTGCCTC
CTCTTGACTTCCCCACTGCTCTCTGTGGTGAGAAATTTGCCTTGTTCAATAATTACTGTACCCTCGCATGACTGTTACAGC
TTTCTGTGCAGAGATGACTGTCCAAGTGCCACATGCCTACGATTGAAATGAAAACTCTATTGTTACCTCTGAGTTGTGTTC
CACGGAAAATGCTATCCAGCAGATCATTTAGGAAAAATAATTCTATTTTTAGCTTTTCATTTCTCAGCTGTCCTTTTTTCTT
GTTTGATTTTTGACAGCAATGGAGAATGGGTTATATAAAGACTGCCTGCTAATATGAACAGAAATGCATTTGTAATTCATG
AAAATAAATGTACATCTTCTATCTTCACATTCATGTTAAGATTCAGTGTTGCTTTCCTCTGGATCAGCGTGTCTGAATGGAC
AGTCAGGTTCAGGTTGTGCTGAACACAGAAATGCTCACAGGCCTCACTTTGCCGCCCAGGCACTGGCCCAGCACTTGGA
TTTACATAAGATGAGTTAGAAAGGTACTTCTGTAGGGTCCTTTTTACCTCTGCTCGGCAGAGAATCGATGCTGTCATGTTC
CTTTATTCACAATCTTAGGTCTCAAATATTCTGTCAAACCCTAACAAAGAAGCCCCGACATCTCAGGTTGGATTCCCTGGT
TCTCTCTAAAGAGGGCCTGCCCTTGTGCCCCAGAGGTGCTGCTGGGCACAGCCAAGAGTTGGGAAGGGCCGCCCCACA
GTACGCAGTCCTCACCACCCAGCCCAGGGTGCTCACGCTCACCACTCCTGTGGCTGAGGAAGGATAGCTGGCTCATCC
TCGGAAAACAGACCCACATCTCTATTCTTGCCCTGAAATACGCGCTTTTCACTTGCGTGCTCAGAGCTGCCGTCTGAAGG
TCCACACAGCATTGACGGGACACAGAAATGTGACTGTTACCGGATAACACTGATTAGTCAGTTTTCATTTATAAAAAAGCA
TTGACAGTTTTATTACTCTTGTTTCTTTTTAAATGGAAAGTTACTATTATAAGGTTAATTTGGAGTCCTCTTCTAAATAGAAA
ACCATATCCTTGGCTACTAACATCTGGAGACTGTGAGCTCCTTCCCATTCCCCTTCCTGGTACTGTGGAGTCAGATTGGC
ATGAAACCACTAACTTCATTCTAGAATCATTGTAGCCATAAGTTGTGTGCTTTTTATTAATCATGCCAAACATAATGTAACT
GGGCAGAGAATGGTCCTAACCAAGGTACCTATGAAAAGCGCTAGCTATCATGTGTAGTAGATGCATCATTTTGGCTCTTC
TTACATT

**MAPK (SEQ ID NO: 8; gi75709178), *(continued)***

TGTAAAAATGTACAGATTAGGTCATCTTAATTCATATTAGTGACACGGAACAGCACCTCCACTATTTGTATGT
TCAAATAAGCTTTCAGACTAATAGCTTTTTTGGTGTCTAAAATGTAAGCAAAAAATTCCTGCTGAAACATTCCA
GTCCTTTCATTTAGTATAAAAGAAATACTGAACAAGCCAGTGGGATGGAATTGAAAGAACTAATCATGAGGA
CTCTGTCCTGACACAGGTCCTCAAAGCTAGCAGAGATACGCAGACATTGTGGCATCTGGGTAGAAGAATAC
TGTATTGTGTGTGCAGTGCACAGTGTGTGGTGTGTGCACACTCATTCCTTCTGCTCTTGGGCACAGGCAGT
GGGTGTAGAGGTAACCAGTAGCTTTGAGAAGCTACATGTAGCTCACCAGTGGTTTTCTCTAAGGAATCACAA
AAGTAAACTACCCAACCACATGCCACGTAATATTTCAGCCATTCAGAGGAAACTGTTTTCTCTTTATTTGCTT
ATATGTTAATATGGTTTTTAAATTGGTAACTTTTATATAGTATGGTAACAGTATGTTAATACACACATACATAC
GCACACATGCTTTGGGTCCTTCCATAATACTTTTATATTTGTAAATCAATGTTTTGGAGCAATCCCAAGTTTAA
GGGAAATATTTTTGTAAATGTAATGGTTTTGAAAATCTGAGCAATCCTTTTGCTTATACATTTTTAAAGCATTT
GTGCTTTAAAATTGTTATGCTGGTGTTTGAAACATGATACTCCTGTGGTGCAGATGAGAAGCTATAACAGTG
AATATGTGGTTTCTCTTACGTCATCCACCTTGACATGATGGGTCAGAAACAAATGGAAATCCAGAGCAAGTC
CTCCAGGGTTGCACCAGGTTTACCTAAAGCTTGTTGCCTTTTCTTGTGCTGTTTATGCGTGTAGAGCACTCA
AGAAAGTTCTGAAACTGCTTTGTATCTGCTTTGTACTGTTGGTGCCTTCTTGGTATTGTACCCCAAAATTCTG
CATAGATTATTTAGTATAATGGTAAGTTAAAAAATGTTAAAGGAAGATTTTATTAAGAATCTGAATGTTTATTC
ATTATATTGTTACAATTTAACATTAACATTTATTTGTGGTATTTGTGATTTGGTTAATCTGTATAAAAATTGTAA
GTAGAAAGGTTTATATTTCATCTTAATTCTTTTGATGTTGTAAACGTACTTTTTAAAAGATGGATTATTTGAATG
TTTATGGCACCTGACTTGTAAAAAAAAAAAACTACAAAAAAATCCTTAGAATCATTAAATTGTGTCCCTGTATT
ACCAAAATAACACAGCACCGTGCATGTATAGTTTAATTGCAGTTTCATCTGTGAAAACGTGAAATTGTCTAGT
CCTTCGTTATGTTCCCCAGATGTCTTCCAGATTTGCTCTGCATGTGGTAACTTGTGTTAGGGCTGTGAGCTG
TTCCTCGAGTTGAATGGGGATGTCAGTGCTCCTAGGGTTCTCCAGGTGGTTCTTCAGACCTTCACCTGTGG
GGGGGGGGGTAGGCGGTGCCCACGCCCATCTCCTCATCCTCCTGAACTTCTGCAACCCCACTGCTGGGCA
GACATCCTGGGCAACCCCTTTTTTCAGAGCAAGAAGTCATAAAGATAGGATTTCTTGGACATTTGGTTCTTAT
CAATATTGGGCATTATGTAATGACTTATTTACAAAACAAAGATACTGGAAAATGTTTTGGATGTGGTGTTATG
GAAAGAGCACAGGCCTTGGACCCATCCAGCTGGGTTCAGAACTACCCCCTGCTTATAACTGCGGCTGGCTG
TGGGCCAGTCATTCTGCGTCTCTGCTTTCTTCCTCTGCTTCAGACTGTCAGCTGTAAAGTGGAAGCAATATT
ACTTGCCTTGTATATGGTAAAGATTATAAAAATACATTTCAACTGTTCAGCATAGTACTTCAAAGCAAGTACTC
AGTAAATAGCAAGTCTTTTTAAA

*Fig. 22B*

MeCP2 Nucleotide Sequence (SEQ ID NO: 9; gi160707948)

CCGGCGTCGGCGGCGCGCGCGCTCCCTCCTCTCGGAGAGAGGGCTGTGGTAAAAGCCGTCCGGAAAATGGCCGCC
GCCGCCGCCGCCGCGCCGAGCGGAGGAGGAGGAGGAGGCGAGGAGGAGAGACTGCTCCATAAAAATACAGACTC
ACCAGTTCCTGCTTTGATGTGACATGTGACTCCCCAGAATACACCTTGCTTCTGTAGACCAGCTCCAACAGGATTCCA
TGGTAGCTGGGATGTTAGGGCTCAGGGAAGAAAAGTCAGAAGACCAGGACCTCCAGGGCCTCAAGGACAAACCCCT
CAAGTTTAAAAAGGTGAAGAAAGATAAGAAAGAAGAGAAAGAGGGCAAGCATGAGCCCGTGCAGCCATCAGCCCAC
CACTCTGCTGAGCCCGCAGAGGCAGGCAAAGCAGAGACATCAGAAGGGTCAGGCTCCGCCCCGGCTGTGCCGGAA
GCTTCTGCCTCCCCCAAACAGCGGCGCTCCATCATCCGTGACCGGGGACCCATGTATGATGACCCCACCCTGCCTG
AAGGCTGGACACGGAAGCTTAAGCAAAGGAAATCTGGCCGCTCTGCTGGGAAGTATGATGTGTATTTGATCAATCCC
CAGGGAAAAGCCTTTCGCTCTAAAGTGGAGTTGATTGCGTACTTCGAAAAGGTAGGCGACACATCCCTGGACCCTAA
TGATTTTGACTTCACGGTAACTGGGAGAGGGAGCCCCTCCCGGCGAGAGCAGAAACCACCTAAGAAGCCCAAATCTC
CCAAAGCTCCAGGAACTGGCAGAGGCCGGGGACGCCCCAAAGGGAGCGGCACCACGAGACCCAAGGCGGCCACG
TCAGAGGGTGTGCAGGTGAAAAGGGTCCTGGAGAAAAGTCCTGGGAAGCTCCTTGTCAAGATGCCTTTTCAAACTTC
GCCAGGGGGCAAGGCTGAGGGGGGTGGGGCCACCACATCCACCCAGGTCATGGTGATCAAACGCCCCGGCAGGAA
GCGAAAAGCTGAGGCCGACCCTCAGGCCATTCCCAAGAAACGGGGCCGAAAGCCGGGGAGTGTGGTGGCAGCCGC
TGCCGCCGAGGCCAAAAAGAAAGCCGTGAAGGAGTCTTCTATCCGATCTGTGCAGGAGACCGTACTCCCCATCAAGA
AGCGCAAGACCCGGGAGACGGTCAGCATCGAGGTCAAGGAAGTGGTGAAGCCCCTGCTGGTGTCCACCCTCGGTG
AGAAGAGCGGGAAAGGACTGAAGACCTGTAAGAGCCCTGGGCGGAAAAGCAAGGAGAGCAGCCCCAAGGGGCGCA
GCAGCAGCGCCTCCTCACCCCCCAAGAAGGAGCACCACCACCATCACCACCACTCAGAGTCCCCAAAGGCCCCCGT
GCCACTGCTCCCACCCCTGCCCCCACCTCCACCTGAGCCCGAGAGCTCCGAGGACCCCACCAGCCCCCCTGAGCC
CCAGGACTTGAGCAGCAGCGTCTGCAAAGAGGAGAAGATGCCCAGAGGAGGCTCACTGGAGAGCGACGGCTGCCC
CAAGGAGCCAGCTAAGACTCAGCCCGCGGTTGCCACCGCCGCCACGGCCGCAGAAAAGTACAAACACCGAGGGGA
GGGAGAGCGCAAAGACATTGTTTCATCCTCCATGCCAAGGCCAAACAGAGAGGAGCCTGTGGACAGCCGGACGCCC
GTGACCGAGAGAGTTAGCTGACTTTACACGGAGCGGATTGCAAAGCAAACCAACAAGAATAAAGGCAGCTGTTGTCT
CTTCTCCTTATGGGTAGGGCTCTGACAAAGCTTCCCGATTAACTGAAATAAAAAATATTTTTTTTTCTTTCAGTAAACTT
AGAGTTTCGTGGCTTCAGGGTGGGAGTAGTTGGAGCATTGGGGATGTTTTTCTTACCGACAAGCACAGTCAGGTTGA
AGACCTAACCAGGGCCAGAAGTAGCTTTGCACTTTTCTAAACTAGGCTCCTTCAACAAGGCTTGCTGCAGATACTACT
GACCAGACAAGCTGTTGACCAGGCACCTCCCCTCCCGCCCAAACCTTTCCCCCATGTGGTCGTTAGAGACAGAGCGA
CAGAGCAGTTGAGAGGACACTCCCGTTTTCGGTGCCATCAGTGCCCCGTCTACAGCTCCCCCAGCTCCCCCCACCTC
CCCCACTCCCAACCACGTTGGGACAGGGAGGTGTGAGGCAGGAGAGACAGTTGGATTCTTTAGAGAAGATGGATAT
GACCAGTGGCTATGGCCTGTGCGATCCCACCCGTGGTGGCTCAAGTCTGGCCCCACACCAGCCCCAATCCAAAACT
GGCAAGGACGCTTCACAGGACAGGAAAGTGGCACCTGTCTGCTCCAGCTCTGGCATGGCTAGGAGGGGGGAGTCC
CTTGAACTACTGGGTGTAGACTGGCCTGAACCACAGGAGAGGATGGCCCAGGGTGAGGTGGCATGGTCCATTCTCA
AGGGACGTCCTCCAACGGGTGGCGCTAGAGGCCATGGAGGCAGTAGGACAAGGTGCAGGCAGGCTGGCCTGGGGT
CAGGCCGGGCAGAGCACAGCGGGGTGAGAGGGATTCCTAATCACTCAGAGCAGTCTGTGACTTAGTGGACAGGGG
AGGGGGCAAAGGGGGAGGAGAAGAAAATGTTCTTCCAGTTACTTTCCAATTCTCCTTTAGGGACAGCTTAGAATTATT
TGCACTATTGAGTCTTCATGTTCCCACTTCAAAACAAACAGATGCTCTGAGAGCAAACTGGCTTGAATTGGTGACATTT
AGTCCCTCAAGCCACCAGATGTGACAGTGTTGAGAACTACCTGGATTTGTATATATACCTGCGCTTGTTTTAAAGTGG
GCTCAGCACATAGGGTTCCCACGAAGCTCCGAAACTCTAAGTGTTTGCTGCAATTTTATAAGGACTTCCTGATTGGTT
TCTCTTCTCCCCTTCCATTTCTGCCTTTTGTTCATTTCATCCTTTCACTTCTTTCCCTTCCTCCGTCCTCCTCCTTCCTAG
TTCATCCCTTCTCTTCCAGGCAGCCGCGGTGCCCAACCACACTTGTCGGCTCCAGTCCCCAGAACTCTGCCTGCCCT
TTGTCCTCCTGCTGCCAGTACCAGCCCCACCCTGTTTTGAGCCCTGAGGAGGCCTTGGGCTCTGCTGAGTCCGACCT
GGCCTGTCTGTGAAGAGCAAGAGAGCAGCAAGGTCTTGCTCTCCTAGGTAGCCCCCTCTTCCCTGGTAAGAAAAAGC
AAAAGGCATTTCCCACCCTGAACAACGAGCCTTTTCACCCTTCTACTCTAGAGAAGTGGACTGGAGGAGCTGGGCCC
GATTTGGTAGTTGAGGAAAGCACAGAGGCCTCCTGTGGCCTGCCAGTCATCGAGTGGCCCAACAGGGGCTCCATGC
CAGCCGACCTTGACCTCACTCAGAAGTCCAGAGTCTAGCGTAGTGCAGCAGGGCAGTAGCGGTACCAATGCAGAAC
TCCCAAGACCCGAGCTGGGACCAGTACCTGGGTCCCCAGCCCTTCCTCTGCTCCCCCTTTTCCCTCGGAGTTCTTCT
TGAATGGCAATGTTTTGCTTTTGCTCGATGCAGACAGGGGGCCAGAACACCACACATTTCACTGTCTGTCTGGTCCAT
AGCTGTGGTGTAGGGGCTTAGAGGCATGGGCTTGCTGTGGGTTTTTAATTGATCAGTTTTCATGTGGGATCCCATCTT
TTTAACCTCTGTTCAGGAAGTCCTTATCTAGCTGCATATCTTCATCATATTGGTATATCCTTTTCTGTGTTTACAGAGAT
GTCTCTTATATCTAAATCTGTCCAACTGAGAAGTACCTTATCAAAGTAGCAAATGAGACAGCAGTCTTATGCTTCCAGA
AACACCCACAGGCATGTCCCATGTGAGCTGCTGCCATGAACTGTCAAGTGTGTGTTGTCTTGTGTATTTCAGTTATTG
TCCCTGGCTTCCTTACTATGGTGTAATCATGAAGGAGTGAAACATCATAGAAACTGTCTAGCACTTCCTTGCCAGTCTT
TAGTGATCAGGAACCATAGTTGACAGTTCCAATCAGTAGCTTAAGAAAAAACCGTGTT

*Fig. 23A* *(cont.)*

MeCP2 Nucleotide Sequence (SEQ ID NO: 9; gi160707948), *(continued)*

TGTCTCTTCTGGAATGGTTAGAAGTGAGGGAGTTTGCCCCGTTCTGTTTGTAGAGTCTCATAGTTGGACTTTCTAGCATATA
TGTGTCCATTTCCTTATGCTGTAAAAGCAAGTCCTGCAACCAAACTCCCATCAGCCCAATCCCTGATCCCTGATCCCTTCCA
CCTGCTCTGCTGATGACCCCCCCAGCTTCACTTCTGACTCTTCCCCAGGAAGGGAAGGGGGGTCAGAAGAGAGGGTGAG
TCCTCCAGAACTCTTCCTCCAAGGACAGAAGGCTCCTGCCCCCATAGTGGCCTCGAACTCCTGGCACTACCAAAGGACAC
TTATCCACGAGAGCGCAGCATCCGACCAGGTTGTCACTGAGAAGATGTTTATTTTGGTCAGTTGGGTTTTTATGTATTATAC
TTAGTCAAATGTAATGTGGCTTCTGGAATCATTGTCCAGAGCTGCTTCCCCGTCACCTGGGCGTCATCTGGTCCTGGTAAG
AGGAGTGCGTGGCCCACCAGGCCCCCCTGTCACCCATGACAGTTCATTCAGGGCCGATGGGGCAGTCGTGGTTGGGAAC
ACAGCATTTCAAGCGTCACTTTATTTCATTCGGGCCCCACCTGCAGCTCCCTCAAAGAGGCAGTTGCCCAGCCTCTTTCCC
TTCCAGTTTATTCCAGAGCTGCCAGTGGGGCCTGAGGCTCCTTAGGGTTTTCTCTCTATTTCCCCCTTTCTTCCTCATTCCC
TCGTCTTTCCCAAAGGCATCACGAGTCAGTCGCCTTTCAGCAGGCAGCCTTGGCGGTTTATCGCCCTGGCAGGCAGGGG
CCCTGCAGCTCTCATGCTGCCCCTGCCTTGGGGTCAGGTTGACAGGAGGTTGGAGGGAAAGCCTTAAGCTGCAGGATTC
TCACCAGCTGTGTCCGGCCCAGTTTTGGGGTGTGACCTCAATTTCAATTTTGTCTGTACTTGAACATTATGAAGATGGGGG
CCTCTTTCAGTGAATTTGTGAACAGCAGAATTGACCGACAGCTTTCCAGTACCCATGGGGCTAGGTCATTAAGGCCACATC
CACAGTCTCCCCCACCCTTGTTCCAGTTGTTAGTTACTACCTCCTCTCCTGACAATACTGTATGTCGTCGAGCTCCCCCCA
GGTCTACCCCTCCCGGCCCTGCCTGCTGGTGGGCTTGTCATAGCCAGTGGGATTGCCGGTCTTGACAGCTCAGTGAGCT
GGAGATACTTGGTCACAGCCAGGCGCTAGCACAGCTCCCTTCTGTTGATGCTGTATTCCCATATCAAAAGACACAGGGGA
CACCCAGAAACGCCACATCCCCCAATCCATCAGTGCCAAACTAGCCAACGGCCCCAGCTTCTCAGCTCGCTGGATGGCG
GAAGCTGCTACTCGTGAGCGCCAGTGCGGGTGCAGACAATCTTCTGTTGGGTGGCATCATTCCAGGCCCGAAGCATGAA
CAGTGCACCTGGGACAGGGAGCAGCCCCAAATTGTCACCTGCTTCTCTGCCCAGCTTTTCATTGCTGTGACAGTGATGGC
GAAAGAGGGTAATAACCAGACACAAACTGCCAAGTTGGGTGGAGAAAGGAGTTTCTTTAGCTGACAGAATCTCTGAATTTT
AAATCACTTAGTAAGCGGCTCAAGCCCAGGAGGGAGCAGAGGGATACGAGCGGAGTCCCCTGCGCGGGACCATCTGGAA
TTGGTTTAGCCCAAGTGGAGCCTGACAGCCAGAACTCTGTGTCCCCCGTCTAACCACAGCTCCTTTTCCAGAGCATTCCAG
TCAGGCTCTCTGGGCTGACTGGGCCAGGGGAGGTTACAGGTACCAGTTCTTTAAGAAGATCTTTGGGCATATACATTTTTA
GCCTGTGTCATTGCCCCAAATGGATTCCTGTTTCAAGTTCACACCTGCAGATTCTAGGACCTGTGTCCTAGACTTCAGGGA
GTCAGCTGTTTCTAGAGTTCCTACCATGGAGTGGGTCTGGAGGACCTGCCCGGTGGGGGGGCAGAGCCCTGCTCCCTCC
GGGTCTTCCTACTCTTCTCTCTGCTCTGACGGGATTTGTTGATTCTCTCCATTTTGGTGTCTTTCTCTTTTAGATATTGTATC
AATCTTTAGAAAAGGCATAGTCTACTTGTTATAAATCGTTAGGATACTGCCTCCCCCAGGGTCTAAAATTACATATTAGAGG
GGAAAAGCTGAACACTGAAGTCAGTTCTCAACAATTTAGAAGGAAAACCTAGAAAACATTTGGCAGAAAATTACATTTCGAT
GTTTTTGAATGAATACGAGCAAGCTTTTACAACAGTGCTGATCTAAAAATACTTAGCACTTGGCCTGAGATGCCTGGTGAG
CATTACAGGCAAGGGGAATCTGGAGGTAGCCGACCTGAGGACATGGCTTCTGAACCTGTCTTTTGGGAGTGGTATGGAAG
GTGGAGCGTTCACCAGTGACCTGGAAGGCCCAGCACCACCCTCCTTCCCACTCTTCTCATCTTGACAGAGCCTGCCCCAG
CGCTGACGTGTCAGGAAAACACCCAGGGAACTAGGAAGGCACTTCTGCCTGAGGGGCAGCCTGCCTTGCCCACTCCTGC
TCTGCTCGCCTCGGATCAGCTGAGCCTTCTGAGCTGGCCTCTCACTGCCTCCCCAAGGCCCCCTGCCTGCCCTGTCAGGA
GGCAGAAGGAAGCAGGTGTGAGGGCAGTGCAAGGAGGGAGCACAACCCCCAGCTCCCGCTCCGGGCTCCGACTTGTGC
ACAGGCAGAGCCCAGACCCTGGAGGAAATCCTACCTTTGAATTCAAGAACATTTGGGGAATTTGGAAATCTCTTTGCCCCC
AAACCCCCATTCTGTCCTACCTTTAATCAGGTCCTGCTCAGCAGTGAGAGCAGATGAGGTGAAAAGGCCAAGAGGTTTGG
CTCCTGCCCACTGATAGCCCCTCTCCCCGCAGTGTTTGTGTGTCAAGTGGCAAAGCTGTTCTTCCTGGTGACCCTGATTAT
ATCCAGTAACACATAGACTGTGCGCATAGGCCTGCTTTGTCTCCTCTATCCTGGGCTTTTGTTTTGCTTTTTAGTTTTGCTTT
TAGTTTTTCTGTCCCTTTTATTTAACGCACCGACTAGACACACAAAGCAGTTGAATTTTTATATATATATCTGTATATTGCACA
ATTATAAACTCATTTTGCTTGTGGCTCCACACACACAAAAAAAGACCTGTTAAAATTATACCTGTTGCTTAATTACAATATTT
CTGATAACCATAGCATAGGACAAGGGAAAATAAAAAAAGAAAAAAAAGAAAAAAAAACGACAAATCTGTCTGCTGGTCACT
TCTTCTGTCCAAGCAGATTCGTGGTCTTTTCCTCGCTTCTTTCAAGGGCTTTCCTGTGCCAGGTGAAGGAGGCTCCAGGCA
GCACCCAGGTTTTGCACTCTTGTTTCTCCCGTGCTTGTGAAAGAGGTCCCAAGGTTCTGGGTGCAGGAGCGCTCCCTTGA
CCTGCTGAAGTCCGGAACGTAGTCGGCACAGCCTGGTCGCCTTCCACCTCTGGGAGCTGGAGTCCACTGGGGTGGCCTG
ACTCCCCCAGTCCCCTTCCCGTGACCTGGTCAGGGTGAGCCCATGTGGAGTCAGCCTCGCAGGCCTCCCTGCCAGTAGG
GTCCGAGTGTGTTTCATCCTTCCCACTCTGTCGAGCCTGGGGGCTGGAGCGGAGACGGGAGGCCTGGCCTGTCTCGGAA
CCTGTGAGCTGCACCAGGTAGAACGCCAGGGACCCCAGAATCATGTGCGTCAGTCCAAGGGGTCCCCTCCAGGAGTAGT
GAAGACTCCAGAAATGTCCCTTTCTTCTCCCCCATCCTACGAGTAATTGCATTTGCTTTTGTAATTCTTAATGAGCAATATCT
GCTAGAGAGTTTAGCTGTAACAGTTCTTTTTGATCATCTTTTTTTAATAATTAGAAACACCAAAAAAATCCAGAAACTTGTTC
TTCCAAAGCAGAGAGCATTATAATCACCAGGGCCAAAAGCTTCCCTCCCTGCTGTCATTGCTTCTTCTGAGGCCTGAATCC
AAAAGAAAAACAGCCATAGGCCCTTTCAGTGGCCGGGCTACCCGTGAGCCCTTCGGAGGACCAGGGCTGGGGCAGCCTC
TGGGCCCACATCCGGGGCCAGCTCCGGCGTGTGTTCAGTGTTAGCAGTGGGTCATGATGCTCTTTCCCACCCAGCCTGG
GATAGGGGCAGAGGAGGCGAGGAGGCCGTTGCCGCTGATGTTTGGCCGTGAACAGG

*Fig. 23B* *(cont.)*

MeCP2 Nucleotide Sequence (SEQ ID NO: 9; gi160707948), *(continued)*

TGGGTGTCTGCGTGCGTCCACGTGCGTGTTTTCTGACTGACATGAAATCGACGCCCGAGTTAGCCTCACCCGGTG
ACCTCTAGCCCTGCCCGGATGGAGCGGGGCCCACCCGGTTCAGTGTTTCTGGGGAGCTGGACAGTGGAGTGCAA
AAGGCTTGCAGAACTTGAAGCCTGCTCCTTCCCTTGCTACCACGGCCTCCTTTCCGTTTGATTTGTCACTGCTTCAA
TCAATAACAGCCGCTCCAGAGTCAGTAGTCAATGAATATATGACCAAATATCACCAGGACTGTTACTCAATGTGTGC
CGAGCCCTTGCCCATGCTGGGCTCCCGTGTATCTGGACACTGTAACGTGTGCTGTGTTTGCTCCCCTTCCCCTTCC
TTCTTTGCCCTTTACTTGTCTTTCTGGGGTTTTTCTGTTTGGGTTTGGTTTGGTTTTTATTTCTCCTTTTGTGTTCCAAA
CATGAGGTTCTCTCTACTGGTCCTCTTAACTGTGGTGTTGAGGCTTATATTTGTGTAATTTTTGGTGGGTGAAAGGA
ATTTTGCTAAGTAAATCTCTTCTGTGTTTGAACTGAAGTCTGTATTGTAACTATGTTTAAAGTAATTGTTCCAGAGACA
AATATTTCTAGACACTTTTTCTTTACAAACAAAAGCATTCGGAGGGAGGGGGATGGTGACTGAGATGAGAGGGGAG
AGCTGAACAGATGACCCCTGCCCAGATCAGCCAGAAGCCACCCAAAGCAGTGGAGCCCAGGAGTCCCACTCCAAG
CCAGCAAGCCGAATAGCTGATGTGTTGCCACTTTCCAAGTCACTGCAAAACCAGGTTTTGTTCCGCCCAGTGGATT
CTTGTTTTGCTTCCCCTCCCCCCGAGATTATTACCACCATCCCGTGCTTTTAAGGAAAGGCAAGATTGATGTTTCCTT
GAGGGGAGCCAGGAGGGGATGTGTGTGTGCAGAGCTGAAGAGCTGGGGAGAATGGGGCTGGGCCCACCCAAGC
AGGAGGCTGGGACGCTCTGCTGTGGGCACAGGTCAGGCTAATGTTGGCAGATGCAGCTCTTCCTGGACAGGCCA
GGTGGTGGGCATTCTCTCTCCAAGGTGTGCCCCGTGGGCATTACTGTTTAAGACACTTCCGTCACATCCCACCCCA
TCCTCCAGGGCTCAACACTGTGACATCTCTATTCCCCACCCTCCCCTTCCCAGGGCAATAAAATGACCATGGAGGG
GGCTTGCACTCTCTTGGCTGTCACCCGATCGCCAGCAAAACTTAGATGTGAGAAAACCCCTTCCCATTCCATGGCG
AAAACATCTCCTTAGAAAAGCCATTACCCTCATTAGGCATGGTTTTGGGCTCCCAAAACACCTGACAGCCCCTCCCT
CCTCTGAGAGGCGGAGAGTGCTGACTGTAGTGACCATTGCATGCCGGGTGCAGCATCTGGAAGAGCTAGGCAGG
GTGTCTGCCCCCTCCTGAGTTGAAGTCATGCTCCCCTGTGCCAGCCCAGAGGCCGAGAGCTATGGACAGCATTGC
CAGTAACACAGGCCACCCTGTGCAGAAGGGAGCTGGCTCCAGCCTGGAAACCTGTCTGAGGTTGGGAGAGGTGC
ACTTGGGGCACAGGGAGAGGCCGGGACACACTTAGCTGGAGATGTCTCTAAAAGCCCTGTATCGTATTCACCTTCA
GTTTTTGTGTTTTGGGACAATTACTTTAGAAAATAAGTAGGTCGTTTTAAAAACAAAAATTATTGATTGCTTTTTTGTA
GTGTTCAGAAAAAAGGTTCTTTGTGTATAGCCAAATGACTGAAAGCACTGATATATTTAAAAACAAAAGGCAATTTAT
TAAGGAAATTTGTACCATTTCAGTAAACCTGTCTGAATGTACCTGTATACGTTTCAAAAACACCCCCCCCCACTGAA
TCCCTGTAACCTATTTATTATATAAAGAGTTTGCCTTATAAATTT

*Fig. 23C*

MeCP2 Polypeptide Sequence (SEQ ID NO:10; gi4826830)

MVAGMLGLREEKSEDQDLQGLKDKPLKFKKVKKDKKEEKEGKHEPVQPSAHHSAEPAEAGKAETS
EGSGSAPAVPEASASPKQRRSIIRDRGPMYDDPTLPEGWTRKLKQRKSGRSAGKYDVYLINPQGKA
FRSKVELIAYFEKVGDTSLDPNDFDFTVTGRGSPSRREQKPPKKPKSPKAPGTGRGRGRPKGSGTT
RPKAATSEGVQVKRVLEKSPGKLLVKMPFQTSPGGKAEGGGATTSTQVMVIKRPGRKRKAEADPQA
IPKKRGRKPGSVVAAAAAEAKKKAVKESSIRSVQETVLPIKKRKTRETVSIEVKEVVKPLLVSTLGEKS
GKGLKTCKSPGRKSKESSPKGRSSSASSPPKKEHHHHHHHSESPKAPVPLLPPLPPPPPEPESSED
PTSPPEPQDLSSSVCKEEKMPRGGSLESDGCPKEPAKTQPAVATAATAAEKYKHRGEGERKDIVSSS
MPRPNREEPVDSRTPVTERVS

*Fig. 24*

RICS Nucleotide Sequence (SEQ ID NO:11; gi218083782)

AAAGCAGTATGTGCTGAGAGAGGAGGATTAAGCTCCTGGAGGCAGAGCTCTCCCACACACTTGCTGGCTTGCTGGGC
TCCACTGACTGGACTGAAAACAGGGCCAAGAAAACTGCTGCTGCAGGGGGTCCTGAAAACAGCTGGAACCCGGCAGT
GATGTGGGACCTAACTTGAAGTTAACCTGTGGTGGTGAGGTTGGAACCAGTTGGATTATGATTTATTTTCTACACTCTT
GTACGGAATGCAGAGCTGTTGTATCCTGATGAATCTACTGCTAAATATAGTCATTTGGAATAATTTTAAGTATTGATCTT
AAAACTTGTACCACAACAAGAGTGTCTAAAAAGCACGGCAAGCTCATTACGTTCTTACGAACATTCATGAAGTCTCGTC
CAACAAAACAGAAGCTGAAGCAGCGGGGAATCTTGAAAGAGAGGGTGTTTGGTTGTGACCTGGGGGAACACCTTCTA
AATTCTGGTTTTGAAGTGCCGCAGGTTCTTCAAAGCTGCACAGCATTCATTGAGAGATATGGCATCGTGGATGGAATC
TATCGCCTTTCTGGTGTTGCCTCCAATATCCAGAGACTACGCCATGAATTTGACTCTGAGCACGTCCCCGACCTGACG
AAAGAACCGTATGTTCAGGACATCCATTCTGTGGGTTCCCTATGTAAGCTGTACTTCCGGGAACTCCCAAACCCTCTG
CTTACCTACCAGCTGTATGAGAAATTTTCTGATGCAGTTTCAGCAGCAACAGATGAAGAAAGGCTGATAAAAATCCACG
ATGTCATCCAGCAGCTCCCCCCACCACACTACAGAACACTGGAGTTCCTGATGAGACACTTGTCTCTTCTAGCTGACT
ATTGTTCCATCACAAATATGCATGCAAAAAATCTAGCAATTGTTTGGGCTCCAAACCTGTTAAGATCAAAACAGATAGAA
TCTGCCTGCTTCAGTGGAACAGCAGCTTTCATGGAAGTGAGGATTCAGTCTGTGGTTGTTGAGTTCATCCTGAATCAC
GTTGATGTGCTGTTCAGCGGCAGAATCAGCATGGCCATGCAAGAGGGGGCAGCTTCTCTATCAAGGCCCAAGTCCCT
CCTGGTATCCTCTCCATCCACCAAACTGCTGACATTGGAAGAGGCCCAGGCACGAACACAAGCTCAGGTCAATTCTCC
AATTGTGACGGAAAATAAATATATCGAAGTAGGAGAAGGACCTGCTGCACTTCAGGGGAAATTTCATACCATAATTGAG
TTCCCACTTGAAAGAAAGAGGCCTCAAAATAAGATGAAAAAGTCTCCTGTGGGTAGCTGGCGTTCCTTTTTCAACTTGG
GGAAATCATCATCTGTTTCTAAACGAAAGCTGCAGCGGAATGAGAGTGAGCCTTCAGAGATGAAAGCCATGGCTCTGA
AAGGTGGCAGGGCAGAAGGAACCCTCCGTTCAGCTAAAAGTGAGGAGTCTCTTACATCTCTCCATGCAGTTGATGGT
GATTCTAAGCTCTTCCGACCCAGAAGACCCAGATCTTCCAGTGATGCACTGTCTGCCTCTTTTAATGGAGAAATGCTG
GGGAACCGCTGTAACTCCTATGATAATCTGCCTCATGACAATGAGAGTGAGGAGGAAGGAGGGCTGCTTCATATCCC
AGCCCTTATGTCTCCTCATTCAGCTGAGGATGTTGACTTGAGCCCACCAGACATTGGAGTAGCCAGCCTGGATTTTGA
TCCAATGTCATTTCAATGTAGTCCTCCTAAGGCCGAATCAGAATGTCTGGAGAGTGGTGCTTCCTTTTTAGATTCACCA
GGATACTCCAAGGATAAACCAAGTGCCAATAAAAAGGATGCAGAAACAGGTAGTAGCCAATGTCAGACTCCAGGAAG
CACAGCAAGCTCTGAACCTGTCTCTCCTCTTCAGGAGAAACTGAGTCCATTCTTTACCCTGGACTTGAGCCCAACTGA
AGATAAATCATCTAAGCCATCCTCCTTTACTGAAAAGGTCGTCTATGCTTTCTCTCCGAAGATAGGACGGAAATTAAGC
AAATCACCTTCTATGAGCATATCTGAGCCAATTTCAGTGACCCTACCACCACGGGTGTCAGAAGTCATTGGTACAGTCT
CAAATACCACAGCTCAGAATGCATCATCTTCAACCTGGGACAAATGCGTTGAAGAAAGGGATGCCACAAATAGATCCC
CCACCCAGATAGTAAAGATGAAAACAAATGAGACAGTTGCCCAAGAAGCATATGAATCTGAAGTCCAGCCCCTGGACC
AGGTGGCTGCTGAAGAAGTAGAATTGCCAGGGAAAGAGGATCAGTCTGTCTCAAGCAGTCAGAGTAAGGCTGTAGCT
TCTGGACAGACTCAGACAGGAGCAGTTACCCATGACCCCCCTCAGGATTCCGTTCCTGTCAGTTCAGTCTCTCTTATC
CCACCACCACCGCCTCCGAAAAATGTTGCCCGAATGTTGGCGCTAGCATTAGCTGAGTCCGCACAGCAAGCCTCAAC
TCAGTCATTGAAGAGACCAGGGACCTCTCAGGCTGGGTATACAAATTATGGAGACATAGCGGTGGCTACAACTGAAG
ATAATCTGTCCAGTTCTTACTCTGCAGTTGCTCTAGATAAGGCCTATTTCCAAACCGATCGACCAGCAGAGCAGTTCCA
CCTCCAGAATAATGCACCAGGAAACTGTGACCATCCTCTACCAGAGACAACAGCTACTGGGGATCCTACCCATTCCAA
CACAACTGAATCTGGGGAGCAACATCACCAAGTAGACTTAACAGGGAATCAGCCACATCAAGCATATTTATCTGGGGA
CCCAGAAAAGGCCAGAATTACTTCAGTTCCCTTAGACTCAGAGAAGTCTGATGATCATGTAAGTTTCCCTGAAGACCA
GTCTGGGAAGAACAGTATGCCAACTGTCTCCTTCTTGGATCAGGACCAGTCTCCACCCCGTTTCTACAGTGGAGATCA
GCCTCCTTCTTATCTTGGTGCAAGTGTGGATAAACTCCATCACCCTTTAGAATTTGCAGACAAATCTCCCACACCTCCT
AATTTACCTAGCGATAAAATCTACCCTCCTTCTGGGTCCCCCGAAGAGAATACCAGCACAGCCACCATGACTTACATG
ACAACTACTCCAGCAACAGCCCAAATGAGCACCAAGGAAGCCAGCTGGGATGTGGCTGAACAACCCACCACTGCTGA
TTTTGCTGCTGCCACACTTCAGCGCACGCACAGAACTAATCGTCCCCTTCCCCCTCCGCCTTCCCAGAGATCTGCAGA
GCAGCCACCAGTTGTGGGGCAGGTACAAGCAGCAACCAATATAGGATTAAATAATTCCCACAAGGTTCAAGGAGTAGT
TCCAGTTCCAGAGAGGCCACCTGAACCTCGAGCCATGGATGACCCTGCGTCTGCCTTCATCAGTGACAGTGGTGCTG
CTGCTGCTCAGTGTCCCATGGCTACAGCTGTCCAGCCAGGCCTGCCTGAGAAAGTGCGGGACGGTGCCCGGGTCCC
GCTGCTGCACCTGCGCGCCGAGTCTGTCCCTGCGCATCCCTGTGGCTTTCCTGCACCACTGCCCCCCACCAGGATGA
TGGAGAGTAAGATGATTGCTGCCATACACTCCAGCAGTGCAGATGCCACCAGCAGTTCAAATTATCATTCCTTTGTCAC
TGCTTCATCCACCTCTGTGGACGATGCATTGCCTTTACCACTTCCTGTCCCACAACCTAAGCATGCTTCTCAGAAAACA
GTTTACTCCTCCTTTGCTAGGCCCGATGTCACCACTGAACCCTTTGGTCCAGATAACTGTTTGCATTTCAATATGACTC
CAAACTGCCAGTACCGTCCCCAGAGTGTACCTCCCCATCACAATAAATTGGAGCAGCACCAAGTGTATGGTGCCAGGT
CAGAGCCACCAGCCTCCATGGGTCTTCGTTATAACACATATGTGGCCCCAGGAAGAAACGCATCTGGACACCACTCCA
AGCCATGCAGCCGGGTCGAGTATGTGTCTTCTTTGAGCTCCTCTGTCAGGAATACCTGTTACCCCGAAGACATTCCAC
CGTACCCTACCATCCGGAGAGTGCAGTCTCTCCATGCTCCGCCGTCTTCCATGATTCGCTCTGTTCCCA

*Fig. 25A (cont.)*

**RICS Nucleotide Sequence (SEQ ID NO:11; gi218083782), *continued***

TTTCACGGACAGAAGTTCCCCCAGATGATGAGCCAGCCTACTGCCCAAGACCTCTGTACCAATATAAGCCATATCAGTCCT
CCCAGGCCCGCTCAGATTATCATGTCACTCAGCTTCAGCCTTACTTTGAGAATGGCCGGGTCCACTACAGGTATAGCCCA
TATTCCAGTTCTTCTAGTTCCTATTACAGTCCAGATGGGGCCCTGTGTGATGTGGATGCCTATGGCACAGTCCAGTTGAGA
CCCCTTCACCGCCTTCCCAATCGAGACTTTGCTTTCTACAATCCTAGGCTGCAAGGAAAGAGCTTGTACAGTTATGCTGGT
TTGGCTCCACGTCCCCGGGCCAACGTGACTGGCTATTTCTCTCCCAACGACCATAATGTAGTCAGCATGCCTCCGGCTGC
TGATGTGAAGCACACCTACACCTCATGGGATCTTGAGGACATGGAAAAATACCGCATGCAGTCCATCCGGAGAGAGAGCC
GTGCTCGGCAGAAGGTGAAAGGGCCTGTCATGTCCCAATATGATAACATGACCCCGGCGGTGCAGGACGACTTGGGTGG
GATCTATGTCATCCATCTGCGTAGTAAATCAGATCCTGGGAAAACTGGACTTCTCTCAGTGGCAGAAGGAAAGGAGAGCC
GCCATGCAGCCAAGGCCATCAGTCCCGAGGGAGAGGACCGCTTCTATAGGAGGCATCCCGAGGCAGAGATGGACAGAG
CCCACCATCACGGAGGCCATGGTAGCACGCAGCCGGAGAAGCCATCCCTGCCTCAGAAGCAGAGCAGCCTGAGGAGCA
GGAAGCTTCCTGACATGGGCTGCAGTCTTCCTGAGCACAGGGCACACCAAGAAGCAAGCCATAGGCAGTTCTGTGAGTC
AAAGAATGGGCCCCCTTATCCCCAGGGAGCTGGCCAGTTAGATTATGGGTCCAAAGGGATTCCAGACACTTCTGAGCCAG
TCAGCTACCACAACTCTGGAGTAAAATATGCTGCATCCGGGCAAGAATCTTTAAGACTGAACCACAAAGAGGTAAGGCTCT
CCAAAGAGATGGAGCGACCCTGGGTTAGGCAGCCTTCTGCCCCAGAGAAACACTCCAGAGACTGCTACAAGGAGGAAGA
ACACCTCACTCAGTCAATCGTCCCACCCCCTAAACCAGAGAGGAGTCATAGCCTCAAACTCCATCATACCCAGAACGTGG
AGAGGGACCCCAGTGTGCTGTACCAGTACCAACCACACGGCAAGCGCCAGAGCAGTGTGACTGTTGTGTCCCAGTATGA
TAACCTGGAAGATTACCACTCCCTGCCTCAGCACCAGCGAGGAGTCTTTGGAGGGGGCGGCATGGGGACGTATGTGCCC
CCTGGCTTTCCCCATCCACAGAGCAGGACCTATGCTACAGCGTTGGGTCAAGGGGCCTTCCTGCCCGCAGAGTTGTCCTT
GCAGCATCCTGAAACACAGATCCATGCAGAATGAGCCCTGCGAGCAATAGAGTTGAAGCAGCCTCTGCTGGACAGTGGA
CTGTTCTATTTTTTTCAATAACCAAAAAGATTAAACAAAAAATACTATAAAACCCCTGACCACATTTAAAAAATGATAATAAAA
GTAAACAAATCAGCATCTTTTTCCCCTTCCCTGCTTCATTACCCCCTCTTCCATCTATAGACTTTGTCATTTTTGTCTTTAGA
AAAGATCTGAAGGATGGTAAAGCCCCGTGCTGAAACCCAGTAGAGAAACCTGTCTCAGGACACACTTGCCATCTAGGGCT
AGCTTGAAAGAGCCTGAGGACTGCCTTTAACTGAATTTGAATTCAGCATTGTCCTTTCTTCTTAGTATTTGCTGCATAATTG
AGAGCAGTTCACATCGATTTCCTGGTAGGCGTCTGCATTCCCTGTTGTGTTCCTGCTTCTCCTTCAGTAGCTGCACAACTT
GCGCAGATCGACACACTGTTGTCACTTCATTCTCCCCGTCTGAGAAGGATCTTGTGTTCAGTTAGAGTCGTGGAAAAATCC
CTGATCCTTCAAGGTCAGTCAGACAGTTGGCAACATTATAATTAAAAATAAGAAATTAAGACTTTAAATTAAACATTTGGTAG
AGTCATCATAAAACACCAGACCACTTAGACTCAGGCTGAACCATACTCTTTCTATTCTTATTTTTCATCCTTGTTCCTCACGG
TTCAGTGAACAGGCTCATATCATGACAGAATGGACTTTTAAAAGTTAGTACTTAAGGAAACTTCTTTAGGTGGAAGAAAGTA
AAGTTCTTATTGTCAGTGAACTTTATTAGCACCAGAAATCTCTATTGATGCTTTTAATGCATTGCCTGCCTTCAGGTTTTCTT
CTTACCCCACCCCTCAATAAGATTTGGTGAATTGTAATTCTAGTAAAACATGTCATACCATTGGTTTTCCTAAATTATCAACT
TTCTTTCATTAAAAAAAAAAAAAAAAAAAAAAAAAGCCCAGCATGGTTTGACTGGATAGACACGCATAATTTATTATGAATATAAA
TTTCCATGTTTGTTTCTGTTCCTAAACCAGAGTACGAGGTCCCTGGGAATTTAAGTAGCTACGCATTATCTATTATTAGACT
GCAAGTTCCTGCAATAACTGCTTAGTTCACAGCCCCGTTTCACCAGTGGAGTTCTGGGCAGTTATTGCTGTCCTAAGGCAT
TACTGTCGTTTGCTTACTCTATACTTGTGTGGTCACAGTCTTCTTGTAATTACCATCTACACCAGCATTTCAGGTATAGCTCT
TTATAACTCTGGAGACATGTAAAACATGTTTAACACCCACGAGTTTTGAAAGTTGCATTCCTTATTAGAGTAGGAACTCTCT
AGCCCAACTCCATTCTATGTTCTCAGCTCCCTCCACCCCCCAAAATACATCAGACTAGCAAGGCAGTCCTATGTTTACAAA
ACGAGTTTAGATTGTCATTTCATTCCATAACTCTTAATAATACTCAAGTTTTATACATTCACGTATTTTAAATGCTCGGTCTGT
AGAAGACACTAGGAGAATTGCATTCCAATTACTGGATGGTTGCTGCTCTGGCTTTTTAGAACTTGAAATTAATTTTTATTTAG
AGCAAAGGAGGAAATCTTTTAAGAGGCTAAAATCATGCTGCTATTATTGCTGTGAAATTGTATAAAGATTAGGATTCATGCC
AGTTTTTATTTTAAAAAATAATGTGCATTTTAAGGGTTTATATTTAGAAAAAAATAAAATGTTTCAAGAACAACACATTGATAT
GTGGAAATATTCTATAAGGTTTTCTTTTGTTCCCTTAGAATTCATTGGAGGGATGCAGTAAAAACTGTAGTAGAAACCTTGA
AACACCCATATGTGAAAAGGTCTGTGGAAATTGAGGCCTCTACATTAAAAGTGCAGAACCAACTGTTTTACAGTCAAAGTG
CTAGGAAACCTGATAGGATACTTCCCTTTGGCACAAAAACACCCTGGGTGCTACATACAGGAGTATGACCTTTGGTGAATA
TGTGGCACTAATTTTTTTTACCTTAATCATATTCTTGTCAAGTAGGCAACCCATTGCCCCTTGGAGACCACACCAGCCCTGT
AAGTTCTCACCAGCAGCATGGAGATTAGGAAGAGGGGCTGCTGTGACCAGGAGATACACACGGCTTTAAGTAACTGAGAG
CCTAAAGAAAGTAACCCAGGGAGTCCGGTCCAGTTTTAATATTTGTGGATTTGTTGTCACACACATTGTTTAGTCCTGAAAC
TAAAACCTATTTTATAAATAGTAGGGTTAATTCCTCGAAACAATTTCTTTATTAATAAATGTCCTGTGGGTTTAGAAATATCA
GGTAAATATTTGAATACAGAATGATGATTGCAATTACTGTTACAAGCGTGAAACACAAACTTCAGATCAAATCTAGAGTTGC
TTCATTTAATGCATGCTAGCAACAGCCTTAACTTTGGATTCAGTTATTTGAAACACTTTTCCGGCATCTTTCCCTTTCTAATG
TTGTGGGGTGGAAACCGGATGGCAAATCACTGTGAGCCGGATACCTCAGCACAGTCCACCTTGTGTGTGACTTCACAAAT
GGGGGACTTCACAAATGGGGTAACTGAATGTTATTACTTTCAAATTTTGACATGGAGCATTATGATCAAGGAAATGGAGCT
GCCTTATACATTAAACCCGTGATTTAATCCTATTGACATTTTCATAGCCATGCCTCCAGATTTTATCTTTTTGGCAAAATTCT
GATTCCACAGTTTGGTCTGATTGAAATAAATATTCCCTGGACGTCTGGCTAAAAATTTTGCTAACAATCCCAGAGGTGCCAT
TTTCTTATTAATAAATTTCATTGGAGCCTTATTTCTTACTATATTCAATTTCGTTTCAAACCTGCAAGTCCCTGGGATGGTCC
CACGACTAGGG

**RICS Nucleotide Sequence (SEQ ID NO:11; gi218083782), *continued***

CCTGCACATTTCTTACAATGGCAAAGCATTTTTTAAAATTTAGGGTCAGGTTGAAAAATTCTAGGACTAATTCT
GTAGAGAGGAGGGACTGTTAACTAACGTGAGTGGGGACGGAGGAGTAGGTTACCACATTTGGAGCAGTAAT
AGATGCAAACGATGTAAATTTGAAATTTGCCCCTTTAGTTAAAGAAGGAGCCTGCAAAGTCCATTTCTCTGTT
TTCAGCCCTGTCAGTCACCCATTTAGGATGTTGGCAAAGTACTGCTTGAGCAGAATGTGTAAGAAAGTAATAA
TGAAAGCAAAAGTATGTCAGACAGTTACTTCTTCCACATGGTTAGAGGCATGTGATTTTCAGCACTGTGTGTT
ACAGAAATGTCAGGAATGGTGTATTATAACGTGTGCAAGATAATGTCAGTGTGCACAGAGGGTCTTTTTTCCT
TATCTGATTAGTACTGTTAATGTTCAAAGAATAAAAATGGTTTTACAGTTTAGATTCTGAGATAGCAAAACCTG
ATTTTTCAACCATGACCTGCATGAGAGAAGCATCCTAGGAAGTCTTAGATCATACTTTTGAGTTTTTAATTTTA
ATTTATATAGTGTTTTTTTATGTCTTAATATTTTTGTGAACTGGTGTAAATTGTTAATGCATATAAGCTTGTGTAT
TTTTGTAAATAGTTTTGTGATTTATTTCTTGCCCCATATGTAAATATTTAGAGTCTCATTTCTTGCAAACTTATTT
GAAGCTGAGTTGTGGGTTTGGGTTTTGTTTGTTTCTTTGGTTGCAGGGTGGGGTGGGGGGTGGCAGGGGAG
GGAGGAAGGGATTTTTGTACCTGGAGATGGAGATATCTTGTGGTTTAAAGCAAATGTCCCACTGAAAGTGAT
TCAAATATCAACAGAATTATTTCAGGTTAAAACAGA

*Fig. 25C*

RICS Polypeptide Sequence (SEQ ID NO:12; gi29469071)

MKSRPTKQKLKQRGILKERVFGCDLGEHLLNSGFEVPQVLQSCTAFIERYGIVDGIYRLSGVASNIQRLRHEFDSEH
VPDLTKEPYVQDIHSVGSLCKLYFRELPNPLLTYQLYEKFSDAVSAATDEERLIKIHDVIQQLPPPHYRTLEFLMRHL
SLLADYCSITNMHAKNLAIVWAPNLLRSKQIESACFSGTAAFMEVRIQSVVVEFILNHVDVLFSGRISMAMQEGAAS
LSRPKSLLVSSPSTKLLTLEEAQARTQAQVNSPIVTENKYIEVGEGPAALQGKFHTIIEFPLERKRPQNKMKKSPVG
SWRSFFNLGKSSSVSKRKLQRNESEPSEMKAMALKGGRAEGTLRSAKSEESLTSLHAVDGDSKLFRPRRPRSSS
DALSASFNGEMLGNRCNSYDNLPHDNESEEEGGLLHIPALMSPHSAEDVDLSPPDIGVASLDFDPMSFQCSPPKA
ESECLESGASFLDSPGYSKDKPSANKKDAETGSSQCQTPGSTASSEPVSPLQEKLSPFFTLDLSPTEDKSSKPSS
FTEKVVYAFSPKIGRKLSKSPSMSISEPISVTLPPRVSEVIGTVSNTTAQNASSSTWDKCVEERDATNRSPTQIVKM
KTNETVAQEAYESEVQPLDQVAAEEVELPGKEDQSVSSSQSKAVASGQTQTGAVTHDPPQDSVPVSSVSLIPPPP
PPKNVARMLALALAESAQQASTQSLKRPGTSQAGYTNYGDIAVATTEDNLSSSYSAVALDKAYFQTDRPAEQFHL
QNNAPGNCDHPLPETTATGDPTHSNTTESGEQHHQVDLTGNQPHQAYLSGDPEKARITSVPLDSEKSDDHVSFP
EDQSGKNSMPTVSFLDQDQSPPRFYSGDQPPSYLGASVDKLHHPLEFADKSPTPPNLPSDKIYPPSGSPEENTST
ATMTYMTTTPATAQMSTKEASWDVAEQPTTADFAAATLQRTHRTNRPLPPPPSQRSAEQPPVVGQVQAATNIGL
NNSHKVQGVVPVPERPPEPRAMDDPASAFISDSGAAAAQCPMATAVQPGLPEKVRDGARVPLLHLRAESVPAHP
CGFPAPLPPTRMMESKMIAAIHSSSADATSSSNYHSFVTASSTSVDDALPLPLPVPQPKHASQKTVYSSFARPDVT
TEPFGPDNCLHFNMTPNCQYRPQSVPPHHNKLEQHQVYGARSEPPASMGLRYNTYVAPGRNASGHHSKPCSRV
EYVSSLSSSVRNTCYPEDIPPYPTIRRVQSLHAPPSSMIRSVPISRTEVPPDDEPAYCPRPLYQYKPYQSSQARSD
YHVTQLQPYFENGRVHYRYSPYSSSSSSYYSPDGALCDVDAYGTVQLRPLHRLPNRDFAFYNPRLQGKSLYSYA
GLAPRPRANVTGYFSPNDHNVVSMPPAADVKHTYTSWDLEDMEKYRMQSIRRESRARQKVKGPVMSQYDNMTP
AVQDDLGGIYVIHLRSKSDPGKTGLLSVAEGKESRHAAKAISPEGEDRFYRRHPEAEMDRAHHHGGHGSTQPEK
PSLPQKQSSLRSRKLPDMGCSLPEHRAHQEASHRQFCESKNGPPYPQGAGQLDYGSKGIPDTSEPVSYHNSGV
KYAASGQESLRLNHKEVRLSKEMERPWVRQPSAPEKHSRDCYKEEEHLTQSIVPPPKPERSHSLKLHHTQNVER
DPSVLYQYQPHGKRQSSVTVVSQYDNLEDYHSLPQHQRGVFGGGGMGTYVPPGFPHPQSRTYATALGQGAFLP
AELSLQHPETQIHAE

*Fig. 26*

SEQUENCE LISTING

```
<160> NUMBER OF SEQ ID NOS: 14

<210> SEQ ID NO 1
<211> LENGTH: 88
<212> TYPE: RNA
<213> ORGANISM: Homo sapiens

<400> SEQUENCE: 1

caccuugucc ucacggucca guuuucccag gaaucccuua gaugcuaaga uggggauucc      60

uggaaauacu guucuugagg ucaugguu                                         88


<210> SEQ ID NO 2
<211> LENGTH: 23
<212> TYPE: RNA
<213> ORGANISM: Homo sapiens

<400> SEQUENCE: 2

guccaguuuu cccaggaauc ccu                                              23
```

<210> SEQ ID NO 3
<211> LENGTH: 101
<212> TYPE: RNA
<213> ORGANISM: Homo sapiens

<400> SEQUENCE: 3
ccgcccccgc gucuccaggg caaccguggc uuucgauugu uacuguggga acuggaggua 60
acagucuaca gccauggucg ccccgcagca cgcccacgcg c 101

<210> SEQ ID NO 4
<211> LENGTH: 22
<212> TYPE: RNA
<213> ORGANISM: Homo sapiens

<400> SEQUENCE: 4
uaacagucua cagccauggu cg 22

<210> SEQ ID NO 5
<211> LENGTH: 110
<212> TYPE: RNA
<213> ORGANISM: Homo sapiens

<400> SEQUENCE: 5
cggggcaccc cgcccggaca gcgcgccggc accuuggcuc uagacugcuu acugcccggg 60
ccgcccucag uaacagucuc cagucacggc caccgacgcc uggccccgcc 110

<210> SEQ ID NO 6
<211> LENGTH: 21
<212> TYPE: RNA
<213> ORGANISM: Homo sapiens

<400> SEQUENCE: 6
uaacagucuc cagucacggc c 21

<210> SEQ ID NO 7
<211> LENGTH: 8743
<212> TYPE: DNA
<213> ORGANISM: Homo sapiens

<400> SEQUENCE: 7
ggttgttttt cggagcctcc ctctgctcag cgttggtggt ggcggtggca gcatggcgag 60
ccctccggag agcgatggct tctcggacgt gcgcaaggtg ggctacctgc gcaaacccaa 120
gagcatgcac aaacgcttct tcgtactgcg cgcggccagc gaggctgggg gcccggcgcg 180
cctcgagtac tacgagaacg agaagaagtg gcggcacaag tcgagcgccc ccaaacgctc 240
gatccccctt gagagctgct tcaacatcaa caagcgggct gactccaaga acaagcacct 300
ggtggctctc tacacccggg acgagcactt tgccatcgcg gcggacagcg aggccgagca 360
agacagctgg taccaggctc tcctacagct gcacaaccgt gctaagggcc accacgacgg 420
agctgcggcc ctcggggcgg gaggtggtgg gggcagctgc agcggcagct ccggccttgg 480
tgaggctggg gaggacttga gctacggtga cgtgccccca ggacccgcat tcaaagaggt 540
ctggcaagtg atcctgaagc ccaagggcct gggtcagaca aagaacctga ttggtatcta 600
ccgcctttgc ctgaccagca agaccatcag cttcgtgaag ctgaactcgg aggcagcggc 660
cgtggtgctg cagctgatga acatcaggcg ctgtggccac tcggaaaact tcttcttcat 720
cgaggtgggc cgttctgccg tgacggggcc cggggagttc tggatgcagg tggatgactc 780
tgtggtggcc cagaacatgc acgagaccat cctggaggcc atgcgggcca tgagtgatga 840

-continued

```
gttccgccct cgcagcaaga gccagtcctc gtccaactgc tctaacccca tcagcgtccc    900
cctgcgccgg caccatctca acaatccccc gcccagccag gtggggctga cccgccgatc    960
acgcactgag agcatcaccg ccacctcccc ggccagcatg gtgggcggga agccaggctc   1020
cttccgtgtc cgcgcctcca gtgacggcga aggcaccatg tcccgcccag cctcggtgga   1080
cggcagccct gtgagtccca gcaccaacag aacccacgcc caccggcatc ggggcagcgc   1140
ccggctgcac cccccgctca accacagccg ctccatcccc atgccggctt cccgctgctc   1200
gccttcggcc accagcccgg tcagtctgtc gtccagtagc accagtggcc atggctccac   1260
ctcggattgt ctcttcccac ggcgatctag tgcttcggtg tctggttccc ccagcgatgg   1320
cggtttcatc tcctcggatg agtatggctc cagtccctgc gatttccgga gttccttccg   1380
cagtgtcact ccggattccc tgggccacac ccccaccagcc cgcggtgagg aggagctaag   1440
caactatatc tgcatgggtg gcaaggggcc ctccaccctg accgccccca acggtcacta   1500
cattttgtct cggggtggca atggccaccg ctgcacccca ggaacaggct tgggcacgag   1560
tccagccttg gctggggatg aagcagccag tgctgcagat ctggataatc ggttccgaaa   1620
gagaactcac tcggcaggca catcccctac cattacccac cagaagaccc cgtcccagtc   1680
ctcagtggct tccattgagg agtacacaga gatgatgcct gcctacccac caggaggtgg   1740
cagtggaggc cgactgccgg gacacaggca ctccgccttc gtgcccaccc gctcctaccc   1800
agaggagggt ctggaaatgc accccttgga gcgtcggggg gggcaccacc gcccagacag   1860
ctccaccctc cacacggatg atggctacat gcccatgtcc ccaggggtgg ccccagtgcc   1920
cagtggccga aagggcagtg gagactatat gcccatgagc cccaagagcg tatctgcccc   1980
acagcagatc atcaatccca tcagacgcca tccccagaga gtggacccca atggctacat   2040
gatgatgtcc cccagcggtg gctgctctcc tgacattgga ggtggcccca gcagcagcag   2100
cagcagcagc aacgccgtcc cttccgggac cagctatgga aagctgtgga caaacggggt   2160
agggggccac cactctcatg tcttgcctca ccccaaaccc ccagtggaga gcagcggtgg   2220
taagctctta ccttgcacag gtgactacat gaacatgtca ccagtggggg actccaacac   2280
cagcagcccc tccgactgct actacggccc tgaggacccc cagcacaagc cagtcctctc   2340
ctactactca ttgccaagat cctttaagca cacccagcgc cccggggagc cggaggaggg   2400
tgcccggcat cagcacctcc gcctttccac tagctctggt cgccttctct atgctgcaac   2460
agcagatgat tcttcctctt ccaccagcag cgacagcctg ggtgggggat actgcggggc   2520
taggctggag cccagccttc cacatcccca ccatcaggtt ctgcagcccc atctgcctcg   2580
aaaggtggac acagctgctc agaccaatag ccgcctggcc cggcccacga ggctgtccct   2640
gggggatccc aaggccagca ccttacctcg ggcccgagag cagcagcagc agcagcagcc   2700
cttgctgcac cctccagagc ccaagagccc gggggaatat gtcaatattg aatttgggag   2760
tgatcagtct ggctacttgt ctggcccggt ggctttccac agctcacctt ctgtcaggtg   2820
tccatcccag ctccagccag ctcccagaga ggaagagact ggcactgagg agtacatgaa   2880
gatggacctg gggccgggcc ggagggcagc ctggcaggag agcactgggg tcgagatggg   2940
cagactgggc cctgcacctc ccggggctgc tagcatttgc aggcctaccc gggcagtgcc   3000
cagcagccgg ggtgactaca tgaccatgca gatgagttgt ccccgtcaga gctacgtgga   3060
cacctcgcca gctgcccctg taagctatgc tgacatgcga acaggcattg ctgcagagga   3120
ggtgagcctg cccagggcca ccatggctgc tgcctcctca tcctcagcag cctctgcttc   3180
cccgactggg cctcaagggg cagcagagct ggctgcccac tcgtccctgc tgggggggccc   3240
```

```
acaaggacct gggggcatga gcgccttcac ccgggtgaac ctcagtccta accgcaacca   3300
gagtgccaaa gtgatccgtg cagacccaca agggtgccgg cggaggcata gctccgagac   3360
tttctcctca acacccagtg ccacccgggt gggcaacaca gtgccctttg gagcgggggc   3420
agcagtaggg ggcggtggcg gtagcagcag cagcagcgag gatgtgaaac gccacagctc   3480
tgcttccttt gagaatgtgt ggctgaggcc tggggagctt gggggagccc ccaaggagcc   3540
agccaaactg tgtggggctg ctgggggttt ggagaatggt cttaactaca tagacctgga   3600
tttggtcaag gacttcaaac agtgccctca ggagtgcacc cctgaaccgc agcctccccc   3660
acccccaccc cctcatcaac ccctgggcag cggtgagagc agctccaccc gccgctcaag   3720
tgaggattta agcgcctatg ccagcatcag tttccagaag cagccagagg accgtcagta   3780
gctcaactgg acatcacagc agaatgaaga cctaaatgac ctcagcaaat cctcttctaa   3840
ctcatgggta cccagactct aaatatttca tgattcacaa ctaggacctc atatcttcct   3900
catcagtaga tggtacgatg catccatttc agtttgttta ctttatccaa tcctcaggat   3960
ttcattgact gaactgcacg ttctatattg tgccaagcga aaaaaaaaaa tgcactgtga   4020
caccagaata atgagtctgc ataaacttca tcttcaacct taaggactta gctggccaca   4080
gtgagctgat gtgcccacca ccgtgtcatg agagaatggg tttactctca atgcattttc   4140
aagatacatt tcatctgctg ctgaaactgt gtacgacaaa gcatcattgt aaattatttc   4200
atacaaaact gttcacgttg ggtggagaga gtattaaata tttaacatag gttttgattt   4260
atatgtgtaa ttttttaaat gaaaatgtaa cttttcttac agcacatctt tttttggat    4320
gtgggatgga ggtatacaat gttctgttgt aaagagtgga gcaaatgctt aaaacaaggc   4380
ttaaaagagt agaatagggt atgatccttg ttttaagatt gtaattcaga aaacataata   4440
taagaatcat agtgccatag atggttctca attgtatagt tatatttgct gatactatct   4500
cttgtcatat aaacctgatg ttgagctgag ttccttataa gaattaatct taattttgta   4560
tttttcctg taagacaata ggccatgtta attaaactga agaaggatat atttggctgg    4620
gtgttttcaa atgtcagctt aaaattggta attgaatgga agcaaaatta taagaagagg   4680
aaattaaagt cttccattgc atgtattgta aacagaagga gatgggtgat tccttcaatt   4740
caaaagctct ctttggaatg aacaatgtgg gcgtttgtaa attctggaaa tgtctttcta   4800
ttcataataa actagatact gttgatcttt tcttctgtcc cctcccccca ccacttctgt   4860
aagtttcctg ctctattccc accatttttt tctgtgcaca cattatgata tatttcattt   4920
cctgcattgt cttgagaaag atggtaaggc aagtgagctg ttgctaacca gaaattaaaa   4980
ttccagtaag tgtttttcat tatgaccagg gctatgtgtc accttcccta agactcttac   5040
cttatctcat attttttgag aacttccagt gttacattat ttaactgaat gtaattggcc   5100
catttgcctt ggtgggtgct ggcctattag tgattagtta acaaaacaca gcgtacagag   5160
agcacagaaa agcttaatga cctgctactg aaacacctag ccagcagtga aaatgttaat   5220
tcttttcttg tttggaaagt atacacgtct tggaattttt tccacgtgaa aaacaaatgg   5280
caatgaatgc atttaaagat attgccgaca gatttttaaa tctttttacc aggaaacttc   5340
ctaaaggtta aatgaattaa tgcaaatatc aggctccctc tgagtctgtg ggagcctcta   5400
tctctctatc aggaattcgc atccctacta ttgggaggag caacatttta tttctctgaa   5460
cgcctaagct ccctgggtgg gagtggggac tacaaggtag ggccagggt tggagggcat    5520
tgtagtggct gctgcctcct gatgaactgt ttggggaccc cagctctact caaaagggag   5580
cggagataaa tggaacccct cacactgctg aggcccgtgt tactgttcat tcagccaggt   5640
```

```
ggcatgtacc tcacagactg ttgtgcagtg tccgttattg cagattttaa tcatttgcat   5700
gctcatcaat ttctaagata aatagggtct agagtcataa gaatccattg ttttcaagga   5760
acttgcagaa ttacatcatt tcctattagt agagagcact acccattttg aaaatctgat   5820
atgaaagttg ttttttactc ttgtaaaaaa agactttctt agtcaaacta acttttcata   5880
ttttcaagca ttctgattca tactcttgct agtggaagaa gagagcaagc tgccctgctc   5940
ttttcctttg aggactgaaa tagttaaaga gaaatcaatg aacaaagtca ctcccaacca   6000
ttttcctgta aagctggtta ttatttctca aggaacctac actttgaata tgtgttaccg   6060
agatacctct acatgtggaa ttatcaacat gttttgaatg agagcagaaa tgaacagact   6120
ggaaaaatct atctcttggt ttctatttct ctgacttttt gagtcgaaaa gcataaaggt   6180
agaaattctt atttaagctg cttctagtgg tgcctgagct ggttttgatg gtggcatcaa   6240
actaccgatt taaaactgga agttgctggt actcaaacca aaagttcata ctctggcgac   6300
acgaagggtt tcctttgagc aacgtcagct gctgagtcct tgtgttcagt tcccattgag   6360
gagagttggc ttttatccat ttcaaagcat ttgtaggcca gccaagggct ttcattattg   6420
aggcttctag tggcctctgg ttaacctaga agttagtggg tttttcttga tgacaccaac   6480
ctctcacagc gtttttcctt agagacttaa gcagagtttt aaaatcctct tttgcgaaaa   6540
gaacaaatat gttttatgac tttgatgata tcttcattct gggcaaaaga atggccctag   6600
aaccagctag aagtgaagag aatccattaa tgatcaacca cctgagtcaa taatgagaaa   6660
tcagtactga tgttacattt gtggctattt cttgctgact ttcaaaggtc aaggactctt   6720
gactaatcca gtgactgcaa aaatggatct actaaaagtc atctagccag aagtagagat   6780
ttttaacctt tctttccctg gcttttgtct tctagctatc atttaaattt gagacatttg   6840
aagtattaag aaacaatttt tctgtatggt aagaaacagt attttacaat actgaagccc   6900
tgttttattc aatcttgcat cttgaataca atataccaca aagtcggaaa ctttatattt   6960
atttactgca ggtggttaaa aaaagggggg aaagggtttc accatccact gacaacgaga   7020
gccatgacaa atagtatcca tgtgcagtct tccaactgct ggtgacaatg accccatatt   7080
tggtctcatg ctgcttttgc agagcactct gtaggttagt ccatcacaca aggaggccct   7140
gaatccagac actgtgaatt aagaccttgg cggggagaga tgtgaccctt ttggtaggaa   7200
tgggaagaag aatgggtgga agccaatatg aaatttcttc tttgcaatga cttgacaggg   7260
gagttaatgt tcctaggatg ccatgaatga tgaatgttag ttggaggtaa tgctgtatat   7320
gtgtgtgtgt gtgtgtgtgt gtgtttgtgt gtgtgtatat atatgtgtgt gtgtatatat   7380
atgtgacatg tgtgtgtctt tgtgtgtgtg tatatatatg tgacgtgtgt gtgggatgtg   7440
tgtgtgtata tatagatgaa tatatacaaa tatatagata tatacacaca tatatagata   7500
tatatacaca tatatagata tatatacaca catatataga tacacatatg tgtgtgtgtg   7560
tatatatata tatatatata tatagatgta taggcttgtg agaaacttga gaggaagaag   7620
catgctcttc taggaatgtg aggaaatatg accttgccaa gactaaaaga cctctagact   7680
gtgagctcag ttatggagaa caaaaacagc ttcatagtga gtagaacacc gaggataaac   7740
actggggcca tgggtccttt ctgaggcagc gccacagaag atctttgtgg tccttccgta   7800
gttctgtaag tctgtctcct aagtatgggt agagaatatg tagcctgttg tgtgtctccc   7860
actacttgta aacagagcat cacattaggg gcagggagga ggtggaatga tattggaggt   7920
gcttaaccct actcgaggaa ttaattatga ataaagagct tataattagc taacatgact   7980
agaaaacaca tgacttaggt ggagagttag ctttcttttc tagtttgtgt atgacttgcc   8040
```

atttgtgacg tatacaccaa aagatctggt gttttagact tctgccattc acttggcatt 8100
taaatctctc tttgcttatg ctgttaacga gtatgccata ggataggaca aattcagtaa 8160
acaggaaaac ttgtccatat ttgcatagac atttgtaggg tttttttttt ctttttcttt 8220
ttagaacttc accattggct taagaatgta gttcccaaaa caatttttttc ttgcaaagta 8280
ctttccttac acctcttggc tacagggtgg gccaaattaa acatatatgt attttcattt 8340
aatgtatgtg cagtttggtt tatcatctta agatggtggt gctgccccgg tgctacttca 8400
tctgtgtaca caaagaccaa tgcatggtct gtattgctac caaaacattt actgtatata 8460
tgtttataac atgtattatg tatatatgta atgggtgcca ggccaggtat atatttttta 8520
tttagaagtg tttcactttt ccaagttttc tttatagtgt tatgcttatt ttcaattttt 8580
tttttcctga ttctgtctgg tacttagaat tgtagtgtct tcatcatcaa ttaaagaaaa 8640
ctgtctaaat gaattcatgg atgtaaatat tagtggtcct taatgtcttt gattgctgga 8700
catgaaacaa actgccaatt aaattttgcg gagacaaaaa aaa 8743

<210> SEQ ID NO 8
<211> LENGTH: 5916
<212> TYPE: DNA
<213> ORGANISM: Homo sapiens

<400> SEQUENCE: 8
gcccctccct ccgcccgccc gccggcccgc ccgtcagtct ggcaggcagg caggcaatcg 60
gtccgagtgg ctgtcggctc ttcagctctc ccgctcggcg tcttccttcc tcctcccggt 120
cagcgtcggc ggctgcaccg gcggcggcgc agtccctgcg ggaggggcga caagagctga 180
gcggcggccg ccgagcgtcg agctcagcgc ggcggaggcg gcggcggccc ggcagccaac 240
atggcggcgg cggcggcggc gggcgcgggc ccggagatgg tccgcgggca ggtgttcgac 300
gtggggccgc gctacaccaa cctctcgtac atcggcgagg gcgcctacgg catggtgtgc 360
tctgcttatg ataatgtcaa caaagttcga gtagctatca agaaaatcag ccccttttgag 420
caccagacct actgccagag aaccctgagg gagataaaaa tcttactgcg cttcagacat 480
gagaacatca ttggaatcaa tgacattatt cgagcaccaa ccatcgagca aatgaaagat 540
gtatatatag tacaggacct catggaaaca gatctttaca agctcttgaa gacacaacac 600
ctcagcaatg accatatctg ctattttctc taccagatcc tcagagggtt aaaatatatc 660
cattcagcta acgttctgca ccgtgacctc aagccttcca acctgctgct caacaccacc 720
tgtgatctca agatctgtga ctttggcctg gcccgtgttg cagatccaga ccatgatcac 780
acagggttcc tgacagaata tgtggccaca cgttggtaca gggctccaga aattatgttg 840
aattccaagg gctacaccaa gtccattgat atttggtctg taggctgcat tctggcagaa 900
atgctttcta acaggcccat ctttccaggg aagcattatc ttgaccagct gaaccacatt 960
ttgggtattc ttggatcccc atcacaagaa gacctgaatt gtataataaa tttaaaagct 1020
aggaactatt tgctttctct tccacacaaa aataaggtgc catggaacag gctgttccca 1080
aatgctgact ccaaagctct ggacttattg gacaaaatgt tgacattcaa cccacacaag 1140
aggattgaag tagaacaggc tctggcccac ccatatctgg agcagtatta cgacccgagt 1200
gacgagccca tcgccgaagc accattcaag ttcgacatgg aattggatga cttgcctaag 1260
gaaaagctca aagaactaat ttttgaagag actgctagat tccagccagg atacagatct 1320
taaatttgtc aggacaaggg ctcagaggac tggacgtgct cagacatcgg tgttcttctt 1380
cccagttctt gacccctggt cctgtctcca gcccgtcttg gcttatccac tttgactcct 1440

```
ttgagccgtt tggaggggcg gtttctggta gttgtggctt ttatgctttc aaagaatttc   1500
ttcagtccag agaattcctc ctggcagccc tgtgtgtgtc acccattggt gacctgcggc   1560
agtatgtact tcagtgcacc tactgcttac tgttgcttta gtcactaatt gctttctggt   1620
ttgaaagatg cagtggttcc tccctctcct gaatcctttt ctacatgatg ccctgctgac   1680
catgcagccg caccagagag agattcttcc ccaattggct ctagtcactg gcatctcact   1740
ttatgatagg gaaggctact acctagggca ctttaagtca gtgacagccc cttatttgca   1800
cttcaccttt tgaccataac tgtttcccca gagcaggagc ttgtggaaat accttggctg   1860
atgttgcagc ctgcagcaag tgcttccgtc tccggaatcc ttggggagca cttgtccacg   1920
tcttttctca tatcatggta gtcactaaca tatataaggt atgtgctatt ggcccagctt   1980
ttagaaaatg cagtcatttt tctaaataaa aaggaagtac tgcacccagc agtgtcactc   2040
tgtagttact gtggtcactt gtaccatata gaggtgtaac acttgtcaag aagcgttatg   2100
tgcagtactt aatgtttgta agacttacaa aaaaagattt aaagtggcag cttcactcga   2160
catttggtga gagaagtaca aaggttgcag tgctgagctg tgggcggttt ctggggatgt   2220
cccagggtgg aactccacat gctggtgcat atacgccctt gagctacttc aaatgtgggt   2280
gtttcagtaa ccacgttcca tgcctgagga tttagcagag aggaacactg cgtctttaaa   2340
tgagaaagta tacaattctt tttccttcta cagcatgtca gcatctcaag ttcatttttc   2400
aacctacagt ataacaattt gtaataaagc ctccaggagc tcatgacgtg aagcactgtt   2460
ctgtcctcaa gtactcaaat atttctgata ctgctgagtc agactgtcag aaaaagctag   2520
cactaactcg tgtttggagc tctatccata ttttactgat ctctttaagt atttgttcct   2580
gccactgtgt actgtggagt tgactcggtg ttctgtccca gtgcggtgcc tcctcttgac   2640
ttccccactg ctctctgtgg tgagaaattt gccttgttca ataattactg taccctcgca   2700
tgactgttac agctttctgt gcagagatga ctgtccaagt gccacatgcc tacgattgaa   2760
atgaaaactc tattgttacc tctgagttgt gttccacgga aaatgctatc cagcagatca   2820
tttaggaaaa ataattctat ttttagcttt tcatttctca gctgtccttt tttcttgttt   2880
gatttttgac agcaatggag aatgggttat ataaagactg cctgctaata tgaacagaaa   2940
tgcatttgta attcatgaaa ataaatgtac atcttctatc ttcacattca tgttaagatt   3000
cagtgttgct ttcctctgga tcagcgtgtc tgaatggaca gtcaggttca ggttgtgctg   3060
aacacagaaa tgctcacagg cctcactttg ccgcccaggc actggcccag cacttggatt   3120
tacataagat gagttagaaa ggtacttctg tagggtcctt tttacctctg ctcggcagag   3180
aatcgatgct gtcatgttcc tttattcaca atcttaggtc tcaaatattc tgtcaaaccc   3240
taacaaagaa gccccgacat ctcaggttgg attccctggt tctctctaaa gagggcctgc   3300
ccttgtgccc cagaggtgct gctgggcaca gccaagagtt gggaagggcc gccccacagt   3360
acgcagtcct caccacccag cccagggtgc tcacgctcac cactcctgtg gctgaggaag   3420
gatagctggc tcatcctcgg aaaacagacc cacatctcta ttcttgccct gaaatacgcg   3480
cttttcactt gcgtgctcag agctgccgtc tgaaggtcca cacagcattg acgggacaca   3540
gaaatgtgac tgttaccgga taacactgat tagtcagttt tcatttataa aaaagcattg   3600
acagttttat tactcttgtt tctttttaaa tggaaagtta ctattataag gttaatttgg   3660
agtcctcttc taaatagaaa accatatcct tggctactaa catctggaga ctgtgagctc   3720
cttcccattc cccttcctgg tactgtggag tcagattggc atgaaaccac taacttcatt   3780
```

-continued

```
ctagaatcat tgtagccata agttgtgtgc tttttattaa tcatgccaaa cataatgtaa   3840
ctgggcagag aatggtccta accaaggtac ctatgaaaag cgctagctat catgtgtagt   3900
agatgcatca ttttggctct tcttacattt gtaaaaatgt acagattagg tcatcttaat   3960
tcatattagt gacacggaac agcacctcca ctatttgtat gttcaaataa gctttcagac   4020
taatagcttt tttggtgtct aaaatgtaag caaaaaattc ctgctgaaac attccagtcc   4080
tttcatttag tataaaagaa atactgaaca agccagtggg atggaattga aagaactaat   4140
catgaggact ctgtcctgac acaggtcctc aaagctagca gagatacgca gacattgtgg   4200
catctgggta gaagaatact gtattgtgtg tgcagtgcac agtgtgtggt gtgtgcacac   4260
tcattccttc tgctcttggg cacaggcagt gggtgtagag gtaaccagta gctttgagaa   4320
gctacatgta gctcaccagt ggttttctct aaggaatcac aaaagtaaac tacccaacca   4380
catgccacgt aatatttcag ccattcagag gaaactgttt tctctttatt tgcttatatg   4440
ttaatatggt ttttaaattg gtaactttta tatagtatgg taacagtatg ttaatacaca   4500
catacatacg cacacatgct ttgggtcctt ccataatact tttatatttg taaatcaatg   4560
ttttggagca atcccaagtt taagggaaat atttttgtaa atgtaatggt tttgaaaatc   4620
tgagcaatcc ttttgcttat acatttttaa agcatttgtg ctttaaaatt gttatgctgg   4680
tgtttgaaac atgatactcc tgtggtgcag atgagaagct ataacagtga atatgtggtt   4740
tctcttacgt catccacctt gacatgatgg gtcagaaaca aatggaaatc cagagcaagt   4800
cctccagggt tgcaccaggt ttacctaaag cttgttgcct tttcttgtgc tgtttatgcg   4860
tgtagagcac tcaagaaagt tctgaaactg ctttgtatct gctttgtact gttggtgcct   4920
tcttggtatt gtaccccaaa attctgcata gattatttag tataatggta agttaaaaaa   4980
tgttaaagga agattttatt aagaatctga atgtttattc attatattgt tacaatttaa   5040
cattaacatt tatttgtggt atttgtgatt tggttaatct gtataaaaat tgtaagtaga   5100
aaggtttata tttcatctta attcttttga tgttgtaaac gtacttttta aaagatggat   5160
tatttgaatg tttatggcac ctgacttgta aaaaaaaaaa actacaaaaa aatccttaga   5220
atcattaaat tgtgtccctg tattaccaaa ataacacagc accgtgcatg tatagtttaa   5280
ttgcagtttc atctgtgaaa acgtgaaatt gtctagtcct tcgttatgtt ccccagatgt   5340
cttccagatt tgctctgcat gtggtaactt gtgttagggc tgtgagctgt tcctcgagtt   5400
gaatggggat gtcagtgctc ctagggttct ccaggtggtt cttcagacct tcacctgtgg   5460
ggggggggt aggcggtgcc cacgcccatc tcctcatcct cctgaacttc tgcaacccca   5520
ctgctgggca gacatcctgg gcaacccctt ttttcagagc aagaagtcat aaagatagga   5580
tttcttggac atttggttct tatcaatatt gggcattatg taatgactta tttacaaaac   5640
aaagatactg gaaaatgttt tggatgtggt gttatggaaa gagcacaggc cttggaccca   5700
tccagctggg ttcagaacta ccccctgctt ataactgcgg ctggctgtgg gccagtcatt   5760
ctgcgtctct gctttcttcc tctgcttcag actgtcagct gtaaagtgga agcaatatta   5820
cttgccttgt atatggtaaa gattataaaa atacatttca actgttcagc atagtacttc   5880
aaagcaagta ctcagtaaat agcaagtctt tttaaa                             5916
```

<210> SEQ ID NO 9
<211> LENGTH: 10241
<212> TYPE: DNA
<213> ORGANISM: Homo sapiens

<400> SEQUENCE: 9

```
ccggcgtcgg cggcgcgcgc gctccctcct ctcggagaga gggctgtggt aaaagccgtc     60
cggaaaatgg ccgccgccgc cgccgccgcg ccgagcggag gaggaggagg aggcgaggag    120
gagagactgc tccataaaaa tacagactca ccagttcctg ctttgatgtg acatgtgact    180
ccccagaata caccttgctt ctgtagacca gctccaacag gattccatgg tagctgggat    240
gttagggctc agggaagaaa agtcagaaga ccaggacctc cagggcctca aggacaaacc    300
cctcaagttt aaaaaggtga agaaagataa gaaagaagag aaagagggca agcatgagcc    360
cgtgcagcca tcagcccacc actctgctga gcccgcagag gcaggcaaag cagagacatc    420
agaagggtca ggctccgccc cggctgtgcc ggaagcttct gcctccccca aacagcggcg    480
ctccatcatc cgtgaccggg gacccatgta tgatgacccc accctgcctg aaggctggac    540
acggaagctt aagcaaagga aatctggccg ctctgctggg aagtatgatg tgtatttgat    600
caatccccag ggaaaagcct ttcgctctaa agtggagttg attgcgtact tcgaaaaggt    660
aggcgacaca tccctggacc ctaatgattt tgacttcacg gtaactggga gagggagccc    720
ctcccggcga gagcagaaac cacctaagaa gcccaaatct cccaaagctc caggaactgg    780
cagaggccgg ggacgcccca aagggagcgg caccacgaga cccaaggcgg ccacgtcaga    840
gggtgtgcag gtgaaaaggg tcctggagaa aagtcctggg aagctccttg tcaagatgcc    900
ttttcaaact tcgccagggg gcaaggctga gggggggtggg gccaccacat ccacccaggt    960
catggtgatc aaacgccccg gcaggaagcg aaaagctgag gccgaccctc aggccattcc   1020
caagaaacgg ggccgaaagc cggggagtgt ggtggcagcc gctgccgccg aggccaaaaa   1080
gaaagccgtg aaggagtctt ctatccgatc tgtgcaggag accgtactcc ccatcaagaa   1140
gcgcaagacc cgggagacgg tcagcatcga ggtcaaggaa gtggtgaagc ccctgctggt   1200
gtccaccctc ggtgagaaga gcgggaaagg actgaagacc tgtaagagcc ctgggcggaa   1260
aagcaaggag agcagcccca aggggcgcag cagcagcgcc tcctcacccc ccaagaagga   1320
gcaccaccac catcaccacc actcagagtc cccaaaggcc cccgtgccac tgctcccacc   1380
cctgccccca cctccacctg agcccgagag ctccgaggac cccaccagcc cccctgagcc   1440
ccaggacttg agcagcagcg tctgcaaaga ggagaagatg cccagaggag gctcactgga   1500
gagcgacggc tgccccaagg agccagctaa gactcagccc gcggttgcca ccgccgccac   1560
ggccgcagaa aagtacaaac accgagggga gggagagcgc aaagacattg tttcatcctc   1620
catgccaagg ccaaacagag aggagcctgt ggacagccgg acgcccgtga ccgagagagt   1680
tagctgactt tacacggagc ggattgcaaa gcaaaccaac aagaataaag gcagctgttg   1740
tctcttctcc ttatgggtag ggctctgaca aagcttcccg attaactgaa ataaaaaata   1800
ttttttttc tttcagtaaa cttagagttt cgtggcttca gggtgggagt agttggagca    1860
ttggggatgt ttttcttacc gacaagcaca gtcaggttga agacctaacc agggccagaa   1920
gtagctttgc acttttctaa actaggctcc ttcaacaagg cttgctgcag atactactga   1980
ccagacaagc tgttgaccag gcacctcccc tcccgcccaa acctttcccc catgtggtcg   2040
ttagagacag agcgacagag cagttgagag gacactcccg ttttcggtgc catcagtgcc   2100
ccgtctacag ctcccccagc tccccccacc tcccccactc ccaaccacgt tgggacaggg   2160
aggtgtgagg caggagagac agttggattc tttagagaag atggatatga ccagtggcta   2220
tggcctgtgc gatcccaccc gtggtggctc aagtctggcc ccacaccagc cccaatccaa   2280
aactggcaag gacgcttcac aggacaggaa agtggcacct gtctgctcca gctctggcat   2340
```

```
ggctaggagg ggggagtccc ttgaactact gggtgtagac tggcctgaac cacaggagag   2400
gatggcccag ggtgaggtgg catggtccat tctcaaggga cgtcctccaa cgggtggcgc   2460
tagaggccat ggaggcagta ggacaaggtg caggcaggct ggcctggggt caggccgggc   2520
agagcacagc ggggtgagag ggattcctaa tcactcagag cagtctgtga cttagtggac   2580
aggggagggg gcaaaggggg aggagaagaa aatgttcttc cagttacttt ccaattctcc   2640
tttagggaca gcttagaatt atttgcacta ttgagtcttc atgttcccac ttcaaaacaa   2700
acagatgctc tgagagcaaa ctggcttgaa ttggtgacat ttagtccctc aagccaccag   2760
atgtgacagt gttgagaact acctggattt gtatatatac ctgcgcttgt tttaaagtgg   2820
gctcagcaca tagggttccc acgaagctcc gaaactctaa gtgtttgctg caattttata   2880
aggacttcct gattggtttc tcttctcccc ttccatttct gccttttgtt catttcatcc   2940
tttcacttct ttcccttcct ccgtcctcct ccttcctagt tcatcccttc tcttccaggc   3000
agccgcggtg cccaaccaca cttgtcggct ccagtcccca gaactctgcc tgccctttgt   3060
cctcctgctg ccagtaccag ccccaccctg ttttgagccc tgaggaggcc ttgggctctg   3120
ctgagtccga cctggcctgt ctgtgaagag caagagagca gcaaggtctt gctctcctag   3180
gtagccccct cttccctggt aagaaaaagc aaaaggcatt tcccaccctg aacaacgagc   3240
cttttcaccc ttctactcta gagaagtgga ctggaggagc tgggcccgat ttggtagttg   3300
aggaaagcac agaggcctcc tgtggcctgc cagtcatcga gtggcccaac aggggctcca   3360
tgccagccga ccttgacctc actcagaagt ccagagtcta gcgtagtgca gcagggcagt   3420
agcggtacca atgcagaact cccaagaccc gagctgggac cagtacctgg gtccccagcc   3480
cttcctctgc tccccctttt ccctcggagt tcttcttgaa tggcaatgtt ttgcttttgc   3540
tcgatgcaga caggggggcca gaacaccaca catttcactg tctgtctggt ccatagctgt   3600
ggtgtagggg cttagaggca tgggcttgct gtgggttttt aattgatcag ttttcatgtg   3660
ggatcccatc tttttaacct ctgttcagga agtccttatc tagctgcata tcttcatcat   3720
attggtatat ccttttctgt gtttacagag atgtctctta tatctaaatc tgtccaactg   3780
agaagtacct tatcaaagta gcaaatgaga cagcagtctt atgcttccag aaacacccac   3840
aggcatgtcc catgtgagct gctgccatga actgtcaagt gtgtgttgtc ttgtgtattt   3900
cagttattgt ccctggcttc cttactatgg tgtaatcatg aaggagtgaa acatcataga   3960
aactgtctag cacttccttg ccagtcttta gtgatcagga accatagttg acagttccaa   4020
tcagtagctt aagaaaaaac cgtgtttgtc tcttctggaa tggttagaag tgagggagtt   4080
tgccccgttc tgtttgtaga gtctcatagt tggactttct agcatatatg tgtccatttc   4140
cttatgctgt aaaagcaagt cctgcaacca aactcccatc agcccaatcc ctgatccctg   4200
atcccttcca cctgctctgc tgatgacccc cccagcttca cttctgactc ttccccagga   4260
agggaagggg ggtcagaaga gagggtgagt cctccagaac tcttcctcca aggacagaag   4320
gctcctgccc ccatagtggc ctcgaactcc tggcactacc aaaggacact tatccacgag   4380
agcgcagcat ccgaccaggt tgtcactgag aagatgttta ttttggtcag ttgggttttt   4440
atgtattata cttagtcaaa tgtaatgtgg cttctggaat cattgtccag agctgcttcc   4500
ccgtcacctg ggcgtcatct ggtcctggta agaggagtgc gtggcccacc aggcccccct   4560
gtcacccatg acagttcatt cagggccgat ggggcagtcg tggttgggaa cacagcattt   4620
caagcgtcac tttatttcat tcgggcccca cctgcagctc cctcaaagag gcagttgccc   4680
agcctctttc ccttccagtt tattccagag ctgccagtgg ggcctgaggc tccttagggt   4740
```

```
tttctctcta tttcccccttt tcttcctcat tccctcgtct ttcccaaagg catcacgagt   4800
cagtcgcctt tcagcaggca gccttggcgg tttatcgccc tggcaggcag gggccctgca   4860
gctctcatgc tgcccctgcc ttggggtcag gttgacagga ggttggaggg aaagccttaa   4920
gctgcaggat tctcaccagc tgtgtccggc ccagttttgg ggtgtgacct caatttcaat   4980
tttgtctgta cttgaacatt atgaagatgg gggcctcttt cagtgaattt gtgaacagca   5040
gaattgaccg acagctttcc agtacccatg gggctaggtc attaaggcca catccacagt   5100
ctcccccacc cttgttccag ttgttagtta ctacctcctc tcctgacaat actgtatgtc   5160
gtcgagctcc ccccaggtct acccctcccg gccctgcctg ctggtgggct tgtcatagcc   5220
agtgggattg ccggtcttga cagctcagtg agctggagat acttggtcac agccaggcgc   5280
tagcacagct cccttctgtt gatgctgtat tcccatatca aaagacacag gggacaccca   5340
gaaacgccac atcccccaat ccatcagtgc caaactagcc aacggcccca gcttctcagc   5400
tcgctggatg gcggaagctg ctactcgtga gcgccagtgc gggtgcagac aatcttctgt   5460
tgggtggcat cattccaggc ccgaagcatg aacagtgcac ctgggacagg gagcagcccc   5520
aaattgtcac ctgcttctct gcccagcttt tcattgctgt gacagtgatg gcgaaagagg   5580
gtaataacca gacacaaact gccaagttgg gtggagaaag gagtttcttt agctgacaga   5640
atctctgaat tttaaatcac ttagtaagcg gctcaagccc aggagggagc agagggatac   5700
gagcggagtc ccctgcgcgg gaccatctgg aattggttta gcccaagtgg agcctgacag   5760
ccagaactct gtgtcccccg tctaaccaca gctccttttc cagagcattc cagtcaggct   5820
ctctgggctg actgggccag gggaggttac aggtaccagt tctttaagaa gatctttggg   5880
catatacatt tttagcctgt gtcattgccc caaatggatt cctgtttcaa gttcacacct   5940
gcagattcta ggacctgtgt cctagacttc agggagtcag ctgtttctag agttcctacc   6000
atggagtggg tctggaggac ctgcccggtg ggggggcaga gccctgctcc ctccgggtct   6060
tcctactctt ctctctgctc tgacgggatt tgttgattct ctccattttg gtgtctttct   6120
cttttagata ttgtatcaat ctttagaaaa ggcatagtct acttgttata aatcgttagg   6180
atactgcctc ccccagggtc taaaattaca tattagaggg gaaaagctga acactgaagt   6240
cagttctcaa caatttagaa ggaaaaccta gaaaacattt ggcagaaaat tacatttcga   6300
tgtttttgaa tgaatacgag caagctttta caacagtgct gatctaaaaa tacttagcac   6360
ttggcctgag atgcctggtg agcattacag gcaaggggaa tctggaggta gccgacctga   6420
ggacatggct tctgaacctg tcttttggga gtggtatgga aggtggagcg ttcaccagtg   6480
acctggaagg cccagcacca ccctccttcc cactcttctc atcttgacag agcctgcccc   6540
agcgctgacg tgtcaggaaa acacccaggg aactaggaag gcacttctgc ctgaggggca   6600
gcctgccttg cccactcctg ctctgctcgc ctcggatcag ctgagccttc tgagctggcc   6660
tctcactgcc tccccaaggc cccctgcctg ccctgtcagg aggcagaagg aagcaggtgt   6720
gagggcagtg caaggaggga gcacaacccc cagctcccgc tccgggctcc gacttgtgca   6780
caggcagagc ccagaccctg gaggaaatcc tacctttgaa ttcaagaaca tttggggaat   6840
ttggaaatct ctttgccccc aaacccccat tctgtcctac ctttaatcag gtcctgctca   6900
gcagtgagag cagatgaggt gaaaaggcca agaggtttgg ctcctgccca ctgatagccc   6960
ctctccccgc agtgtttgtg tgtcaagtgg caaagctgtt cttcctggtg accctgatta   7020
tatccagtaa cacatagact gtgcgcatag gcctgctttg tctcctctat cctgggcttt   7080
tgttttgctt tttagttttg cttttagttt ttctgtccct tttatttaac gcaccgacta   7140
```

```
gacacacaaa gcagttgaat ttttatatat atatctgtat attgcacaat tataaactca   7200
ttttgcttgt ggctccacac acacaaaaaa agacctgtta aaattatacc tgttgcttaa   7260
ttacaatatt tctgataacc atagcatagg acaagggaaa ataaaaaaag aaaaaaaaga   7320
aaaaaaaacg acaaatctgt ctgctggtca cttcttctgt ccaagcagat tcgtggtctt   7380
ttcctcgctt ctttcaaggg ctttcctgtg ccaggtgaag gaggctccag gcagcaccca   7440
ggttttgcac tcttgtttct cccgtgcttg tgaaagaggt cccaaggttc tgggtgcagg   7500
agcgctccct tgacctgctg aagtccggaa cgtagtcggc acagcctggt cgccttccac   7560
ctctgggagc tggagtccac tggggtggcc tgactccccc agtccccttc ccgtgacctg   7620
gtcagggtga gcccatgtgg agtcagcctc gcaggcctcc ctgccagtag ggtccgagtg   7680
tgtttcatcc ttcccactct gtcgagcctg ggggctggag cggagacggg aggcctggcc   7740
tgtctcggaa cctgtgagct gcaccaggta gaacgccagg gaccccagaa tcatgtgcgt   7800
cagtccaagg ggtcccctcc aggagtagtg aagactccag aaatgtccct ttcttctccc   7860
ccatcctacg agtaattgca tttgcttttg taattcttaa tgagcaatat ctgctagaga   7920
gtttagctgt aacagttctt tttgatcatc ttttttttaat aattagaaac accaaaaaaa   7980
tccagaaact tgttcttcca aagcagagag cattataatc accagggcca aaagcttccc   8040
tccctgctgt cattgcttct tctgaggcct gaatccaaaa gaaaaacagc cataggccct   8100
ttcagtggcc gggctacccg tgagcccttc ggaggaccag ggctggggca gcctctgggc   8160
ccacatccgg ggccagctcc ggcgtgtgtt cagtgttagc agtgggtcat gatgctcttt   8220
cccacccagc ctgggatagg ggcagaggag gcgaggaggc cgttgccgct gatgtttggc   8280
cgtgaacagg tgggtgtctg cgtgcgtcca cgtgcgtgtt ttctgactga catgaaatcg   8340
acgcccgagt tagcctcacc cggtgacctc tagccctgcc cggatggagc ggggcccacc   8400
cggttcagtg tttctgggga gctggacagt ggagtgcaaa aggcttgcag aacttgaagc   8460
ctgctccttc ccttgctacc acggcctcct ttccgtttga tttgtcactg cttcaatcaa   8520
taacagccgc tccagagtca gtagtcaatg aatatatgac caaatatcac caggactgtt   8580
actcaatgtg tgccgagccc ttgcccatgc tgggctcccg tgtatctgga cactgtaacg   8640
tgtgctgtgt ttgctcccct tccccttcct tctttgccct ttacttgtct ttctggggtt   8700
tttctgtttg ggtttggttt ggtttttatt tctccttttg tgttccaaac atgaggttct   8760
ctctactggt cctcttaact gtggtgttga ggcttatatt tgtgtaattt ttggtgggtg   8820
aaaggaattt tgctaagtaa atctcttctg tgtttgaact gaagtctgta ttgtaactat   8880
gtttaaagta attgttccag agacaaatat ttctagacac tttttcttta caaacaaaag   8940
cattcggagg gagggggatg gtgactgaga tgagagggga gagctgaaca gatgacccct   9000
gcccagatca gccagaagcc acccaaagca gtggagccca ggagtcccac tccaagccag   9060
caagccgaat agctgatgtg ttgccacttt ccaagtcact gcaaaaccag gttttgttcc   9120
gcccagtgga ttcttgtttt gcttcccctc cccccgagat tattaccacc atcccgtgct   9180
tttaaggaaa ggcaagattg atgtttcctt gaggggagcc aggaggggat gtgtgtgtgc   9240
agagctgaag agctggggag aatggggctg ggcccaccca agcaggaggc tgggacgctc   9300
tgctgtgggc acaggtcagg ctaatgttgg cagatgcagc tcttcctgga caggccaggt   9360
ggtgggcatt ctctctccaa ggtgtgcccc gtgggcatta ctgtttaaga cacttccgtc   9420
acatcccacc ccatcctcca gggctcaaca ctgtgacatc tctattcccc accctcccct   9480
tcccagggca ataaaatgac catggagggg gcttgcactc tcttggctgt cacccgatcg   9540
```

```
ccagcaaaac ttagatgtga gaaaacccct tcccattcca tggcgaaaac atctccttag   9600

aaaagccatt accctcatta ggcatggttt tgggctccca aaacacctga cagcccctcc   9660

ctcctctgag aggcggagag tgctgactgt agtgaccatt gcatgccggg tgcagcatct   9720

ggaagagcta ggcagggtgt ctgccccctc ctgagttgaa gtcatgctcc cctgtgccag   9780

cccagaggcc gagagctatg gacagcattg ccagtaacac aggccaccct gtgcagaagg   9840

gagctggctc cagcctggaa acctgtctga ggttgggaga ggtgcacttg ggcacagggg   9900

agaggccggg acacacttag ctggagatgt ctctaaaagc cctgtatcgt attcaccttc   9960

agtttttgtg ttttgggaca attactttag aaaataagta ggtcgtttta aaaacaaaaa  10020

ttattgattg ctttttgta gtgttcagaa aaaaggttct ttgtgtatag ccaaatgact  10080

gaaagcactg atatatttaa aaacaaaagg caatttatta aggaaatttg taccatttca  10140

gtaaacctgt ctgaatgtac ctgtatacgt ttcaaaaaca cccccccccc actgaatccc  10200

tgtaacctat ttattatata aagagtttgc cttataaatt t                       10241


<210> SEQ ID NO 10
<211> LENGTH: 486
<212> TYPE: PRT
<213> ORGANISM: Homo sapiens

<400> SEQUENCE: 10

Met Val Ala Gly Met Leu Gly Leu Arg Glu Glu Lys Ser Glu Asp Gln
1               5                   10                  15

Asp Leu Gln Gly Leu Lys Asp Lys Pro Leu Lys Phe Lys Lys Val Lys
            20                  25                  30

Lys Asp Lys Lys Glu Glu Lys Glu Gly Lys His Glu Pro Val Gln Pro
        35                  40                  45

Ser Ala His His Ser Ala Glu Pro Ala Glu Ala Gly Lys Ala Glu Thr
    50                  55                  60

Ser Glu Gly Ser Gly Ser Ala Pro Ala Val Pro Glu Ala Ser Ala Ser
65                  70                  75                  80

Pro Lys Gln Arg Arg Ser Ile Ile Arg Asp Arg Gly Pro Met Tyr Asp
                85                  90                  95

Asp Pro Thr Leu Pro Glu Gly Trp Thr Arg Lys Leu Lys Gln Arg Lys
            100                 105                 110

Ser Gly Arg Ser Ala Gly Lys Tyr Asp Val Tyr Leu Ile Asn Pro Gln
        115                 120                 125

Gly Lys Ala Phe Arg Ser Lys Val Glu Leu Ile Ala Tyr Phe Glu Lys
    130                 135                 140

Val Gly Asp Thr Ser Leu Asp Pro Asn Asp Phe Asp Phe Thr Val Thr
145                 150                 155                 160

Gly Arg Gly Ser Pro Ser Arg Arg Glu Gln Lys Pro Pro Lys Lys Pro
                165                 170                 175

Lys Ser Pro Lys Ala Pro Gly Thr Gly Arg Gly Arg Gly Arg Pro Lys
            180                 185                 190

Gly Ser Gly Thr Thr Arg Pro Lys Ala Ala Thr Ser Glu Gly Val Gln
        195                 200                 205

Val Lys Arg Val Leu Glu Lys Ser Pro Gly Lys Leu Leu Val Lys Met
    210                 215                 220

Pro Phe Gln Thr Ser Pro Gly Gly Lys Ala Glu Gly Gly Gly Ala Thr
225                 230                 235                 240

Thr Ser Thr Gln Val Met Val Ile Lys Arg Pro Gly Arg Lys Arg Lys
                245                 250                 255
```

```
Ala Glu Ala Asp Pro Gln Ala Ile Pro Lys Lys Arg Gly Arg Lys Pro
            260                 265                 270

Gly Ser Val Val Ala Ala Ala Ala Ala Glu Ala Lys Lys Lys Ala Val
        275                 280                 285

Lys Glu Ser Ser Ile Arg Ser Val Gln Glu Thr Val Leu Pro Ile Lys
    290                 295                 300

Lys Arg Lys Thr Arg Glu Thr Val Ser Ile Glu Val Lys Glu Val Val
305                 310                 315                 320

Lys Pro Leu Leu Val Ser Thr Leu Gly Glu Lys Ser Gly Lys Gly Leu
                325                 330                 335

Lys Thr Cys Lys Ser Pro Gly Arg Lys Ser Lys Glu Ser Ser Pro Lys
            340                 345                 350

Gly Arg Ser Ser Ser Ala Ser Ser Pro Pro Lys Lys Glu His His His
        355                 360                 365

His His His His Ser Glu Ser Pro Lys Ala Pro Val Pro Leu Leu Pro
    370                 375                 380

Pro Leu Pro Pro Pro Pro Pro Glu Pro Glu Ser Ser Glu Asp Pro Thr
385                 390                 395                 400

Ser Pro Pro Glu Pro Gln Asp Leu Ser Ser Ser Val Cys Lys Glu Glu
                405                 410                 415

Lys Met Pro Arg Gly Gly Ser Leu Glu Ser Asp Gly Cys Pro Lys Glu
            420                 425                 430

Pro Ala Lys Thr Gln Pro Ala Val Ala Thr Ala Ala Thr Ala Ala Glu
        435                 440                 445

Lys Tyr Lys His Arg Gly Glu Gly Glu Arg Lys Asp Ile Val Ser Ser
    450                 455                 460

Ser Met Pro Arg Pro Asn Arg Glu Glu Pro Val Asp Ser Arg Thr Pro
465                 470                 475                 480

Val Thr Glu Arg Val Ser
                485
```

<210> SEQ ID NO 11
<211> LENGTH: 9443
<212> TYPE: DNA
<213> ORGANISM: Homo sapiens

<400> SEQUENCE: 11

```
aaagcagtat gtgctgagag aggaggatta agctcctgga ggcagagctc tcccacacac     60

ttgctggctt gctgggctcc actgactgga ctgaaaacag ggccaagaaa actgctgctg    120

cagggggtcc tgaaaacagc tggaacccgg cagtgatgtg ggacctaact tgaagttaac    180

ctgtggtggt gaggttggaa ccagttggat tatgatttat tttctacact cttgtacgga    240

atgcagagct gttgtatcct gatgaatcta ctgctaaata tagtcatttg gaataatttt    300

aagtattgat cttaaaactt gtaccacaac aagagtgtct aaaaagcacg gcaagctcat    360

tacgttctta cgaacattca tgaagtctcg tccaacaaaa cagaagctga agcagcgggg    420

aatcttgaaa gagagggtgt ttggttgtga cctgggggaa caccttctaa attctggttt    480

tgaagtgccg caggttcttc aaagctgcac agcattcatt gagagatatg gcatcgtgga    540

tggaatctat cgcctttctg gtgttgcctc caatatccag agactacgcc atgaatttga    600

ctctgagcac gtccccgacc tgacgaaaga accgtatgtt caggacatcc attctgtggg    660

ttccctatgt aagctgtact tccgggaact cccaaaccct ctgcttacct accagctgta    720

tgagaaattt tctgatgcag tttcagcagc aacagatgaa gaaaggctga taaaaatcca    780
```

-continued

```
cgatgtcatc cagcagctcc ccccaccaca ctacagaaca ctggagttcc tgatgagaca    840
cttgtctctt ctagctgact attgttccat cacaaatatg catgcaaaaa atctagcaat    900
tgtttgggct ccaaacctgt taagatcaaa acagatagaa tctgcctgct tcagtggaac    960
agcagctttc atggaagtga ggattcagtc tgtggttgtt gagttcatcc tgaatcacgt   1020
tgatgtgctg ttcagcggca gaatcagcat ggccatgcaa gagggggcag cttctctatc   1080
aaggcccaag tccctcctgg tatcctctcc atccaccaaa ctgctgacat tggaagaggc   1140
ccaggcacga acacaagctc aggtcaattc tccaattgtg acggaaaata aatatatcga   1200
agtaggagaa ggacctgctg cacttcaggg gaaatttcat accataattg agttcccact   1260
tgaaagaaag aggcctcaaa ataagatgaa aaagtctcct gtgggtagct ggcgttcctt   1320
tttcaacttg ggaaatcat catctgtttc taaacgaaag ctgcagcgga atgagagtga   1380
gccttcagag atgaaagcca tggctctgaa aggtggcagg gcagaaggaa ccctccgttc   1440
agctaaaagt gaggagtctc ttacatctct ccatgcagtt gatggtgatt ctaagctctt   1500
ccgacccaga agacccagat cttccagtga tgcactgtct gcctctttta atggagaaat   1560
gctggggaac cgctgtaact cctatgataa tctgcctcat gacaatgaga gtgaggagga   1620
aggagggctg cttcatatcc cagcccttat gtctcctcat tcagctgagg atgttgactt   1680
gagcccacca gacattggag tagccagcct ggattttgat ccaatgtcat ttcaatgtag   1740
tcctcctaag gccgaatcag aatgtctgga gagtggtgct tcctttttag attcaccagg   1800
atactccaag gataaaccaa gtgccaataa aaaggatgca gaaacaggta gtagccaatg   1860
tcagactcca ggaagcacag caagctctga acctgtctct cctcttcagg agaaactgag   1920
tccattcttt accctggact tgagcccaac tgaagataaa tcatctaagc catcctcctt   1980
tactgaaaag gtcgtctatg ctttctctcc gaagatagga cggaaattaa gcaaatcacc   2040
ttctatgagc atatctgagc caatttcagt gaccctacca ccacgggtgt cagaagtcat   2100
tggtacagtc tcaaatacca cagctcagaa tgcatcatct tcaacctggg acaaatgcgt   2160
tgaagaaagg gatgccacaa atagatcccc cacccagata gtaaagatga aaacaaatga   2220
gacagttgcc caagaagcat atgaatctga agtccagccc ctggaccagg tggctgctga   2280
agaagtagaa ttgccaggga aagaggatca gtctgtctca agcagtcaga gtaaggctgt   2340
agcttctgga cagactcaga caggagcagt tacccatgac ccccctcagg attccgttcc   2400
tgtcagttca gtctctctta tcccaccacc accgcctccg aaaaatgttg cccgaatgtt   2460
ggcgctagca ttagctgagt ccgcacagca agcctcaact cagtcattga agagaccagg   2520
gacctctcag gctgggtata caaattatgg agacatagcg gtggctacaa ctgaagataa   2580
tctgtccagt tcttactctg cagttgctct agataaggcc tatttccaaa ccgatcgacc   2640
agcagagcag ttccacctcc agaataatgc accaggaaac tgtgaccatc ctctaccaga   2700
gacaacagct actggggatc ctacccattc caacacaact gaatctgggg agcaacatca   2760
ccaagtagac ttaacaggga atcagccaca tcaagcatat ttatctgggg acccagaaaa   2820
ggccagaatt acttcagttc ccttagactc agagaagtct gatgatcatg taagtttccc   2880
tgaagaccag tctgggaaga acagtatgcc aactgtctcc ttcttggatc aggaccagtc   2940
tccacccccgt ttctacagtg gagatcagcc tccttcttat cttggtgcaa gtgtggataa   3000
actccatcac cctttagaat ttgcagacaa atctcccaca cctcctaatt tacctagcga   3060
taaaatctac cctccttctg ggtcccccga agagaatacc agcacagcca ccatgactta   3120
catgacaact actccagcaa cagcccaaat gagcaccaag gaagccagct gggatgtggc   3180
```

```
tgaacaaccc accactgctg attttgctgc tgccacactt cagcgcacgc acagaactaa   3240
tcgtcccctt cccctccgc cttcccagag atctgcagag cagccaccag ttgtggggca   3300
ggtacaagca gcaaccaata taggattaaa taattcccac aaggttcaag gagtagttcc   3360
agttccagag aggccacctg aacctcgagc catggatgac cctgcgtctg ccttcatcag   3420
tgacagtggt gctgctgctg ctcagtgtcc catggctaca gctgtccagc caggcctgcc   3480
tgagaaagtg cgggacggtg cccgggtccc gctgctgcac ctgcgcgccg agtctgtccc   3540
tgcgcatccc tgtggctttc ctgcaccact gccccccacc aggatgatgg agagtaagat   3600
gattgctgcc atacactcca gcagtgcaga tgccaccagc agttcaaatt atcattcctt   3660
tgtcactgct tcatccacct ctgtggacga tgcattgcct ttaccacttc ctgtcccaca   3720
acctaagcat gcttctcaga aaacagttta ctcctccttt gctaggcccg atgtcaccac   3780
tgaacccttt ggtccagata actgtttgca tttcaatatg actccaaact gccagtaccg   3840
tccccagagt gtacctcccc atcacaataa attggagcag caccaagtgt atggtgccag   3900
gtcagagcca ccagcctcca tgggtcttcg ttataacaca tatgtggccc caggaagaaa   3960
cgcatctgga caccactcca agccatgcag ccgggtcgag tatgtgtctt ctttgagctc   4020
ctctgtcagg aatacctgtt accccgaaga cattccaccg taccctacca tccggagagt   4080
gcagtctctc catgctccgc cgtcttccat gattcgctct gttcccattt cacggacaga   4140
agttccccca gatgatgagc cagcctactg cccaagacct ctgtaccaat ataagccata   4200
tcagtcctcc caggcccgct cagattatca tgtcactcag cttcagcctt actttgagaa   4260
tggccgggtc cactacaggt atagcccata ttccagttct tctagttcct attacagtcc   4320
agatggggcc ctgtgtgatg tggatgccta tggcacagtc cagttgagac cccttcaccg   4380
ccttcccaat cgagactttg ctttctacaa tcctaggctg caaggaaaga gcttgtacag   4440
ttatgctggt ttggctccac gtccccgggc caacgtgact ggctatttct ctcccaacga   4500
ccataatgta gtcagcatgc ctccggctgc tgatgtgaag cacacctaca cctcatggga   4560
tcttgaggac atggaaaaat accgcatgca gtccatccgg agagagagcc gtgctcggca   4620
gaaggtgaaa gggcctgtca tgtcccaata tgataacatg accccggcgg tgcaggacga   4680
cttgggtggg atctatgtca tccatctgcg tagtaaatca gatcctggga aaactggact   4740
tctctcagtg gcagaaggaa aggagagccg ccatgcagcc aaggccatca gtcccgaggg   4800
agaggaccgc ttctatagga ggcatcccga ggcagagatg gacagagccc accatcacgg   4860
aggccatggt agcacgcagc cggagaagcc atccctgcct cagaagcaga gcagcctgag   4920
gagcaggaag cttcctgaca tgggctgcag tcttcctgag cacagggcac accaagaagc   4980
aagccatagg cagttctgtg agtcaaagaa tgggcccccct tatccccagg gagctggcca   5040
gttagattat gggtccaaag ggattccaga cacttctgag ccagtcagct accacaactc   5100
tggagtaaaa tatgctgcat ccgggcaaga atctttaaga ctgaaccaca aagaggtaag   5160
gctctccaaa gagatggagc gaccctgggt taggcagcct tctgccccag agaaacactc   5220
cagagactgc tacaaggagg aagaacacct cactcagtca atcgtcccac cccctaaacc   5280
agagaggagt catagcctca aactccatca tacccagaac gtggagaggg accccagtgt   5340
gctgtaccag taccaaccac acggcaagcg ccagagcagt gtgactgttg tgtcccagta   5400
tgataacctg gaagattacc actccctgcc tcagcaccag cgaggagtct ttggaggggg   5460
cggcatgggg acgtatgtgc cccctggctt tccccatcca cagagcagga cctatgctac   5520
agcgttgggt caaggggcct tcctgcccgc agagttgtcc ttgcagcatc ctgaaacaca   5580
```

-continued

```
gatccatgca gaatgagccc tgcgagcaat agagttgaag cagcctctgc tggacagtgg   5640
actgttctat ttttttcaat aaccaaaaag attaaacaaa aaatactata aaacccctga   5700
ccacatttaa aaaatgataa taaaagtaaa caaatcagca tctttttccc cttccctgct   5760
tcattacccc ctcttccatc tatagacttt gtcatttttg tctttagaaa agatctgaag   5820
gatggtaaag ccccgtgctg aaacccagta gagaaacctg tctcaggaca cacttgccat   5880
ctagggctag cttgaaagag cctgaggact gcctttaact gaatttgaat tcagcattgt   5940
cctttcttct tagtatttgc tgcataattg agagcagttc acatcgattt cctggtaggc   6000
gtctgcattc cctgttgtgt tcctgcttct ccttcagtag ctgcacaact tgcgcagatc   6060
gacacactgt tgtcacttca ttctccccgt ctgagaagga tcttgtgttc agttagagtc   6120
gtggaaaaat ccctgatcct tcaaggtcag tcagacagtt ggcaacatta taattaaaaa   6180
taagaaatta agactttaaa ttaaacattt ggtagagtca tcataaaaca ccagaccact   6240
tagactcagg ctgaaccata ctctttctat tcttattttt catccttgtt cctcacggtt   6300
cagtgaacag gctcatatca tgacagaatg gacttttaaa agttagtact taaggaaact   6360
tctttaggtg gaagaaagta aagttcttat tgtcagtgaa ctttattagc accagaaatc   6420
tctattgatg cttttaatgc attgcctgcc ttcaggtttt cttcttaccc cacccctcaa   6480
taagatttgg tgaattgtaa ttctagtaaa acatgtcata ccattggttt tcctaaatta   6540
tcaactttct ttcattaaaa aaaaaaaaaa aaaaaaaagc ccagcatggt ttgactggat   6600
agacacgcat aatttattat gaatataaat ttccatgttt gtttctgttc ctaaaccaga   6660
gtacgaggtc cctgggaatt taagtagcta cgcattatct attattagac tgcaagttcc   6720
tgcaataact gcttagttca cagccccgtt tcaccagtgg agttctgggc agttattgct   6780
gtcctaaggc attactgtcg tttgcttact ctatacttgt gtggtcacag tcttcttgta   6840
attaccatct acaccagcat ttcaggtata gctctttata actctggaga catgtaaaac   6900
atgtttaaca cccacgagtt ttgaaagttg cattccttat tagagtagga actctctagc   6960
ccaactccat tctatgttct cagctccctc caccccccaa aatacatcag actagcaagg   7020
cagtcctatg tttacaaaac gagtttagat tgtcatttca ttccataact cttaataata   7080
ctcaagtttt atacattcac gtattttaaa tgctcggtct gtagaagaca ctaggagaat   7140
tgcattccaa ttactggatg gttgctgctc tggcttttta gaacttgaaa ttaattttta   7200
tttagagcaa aggaggaaat cttttaagag gctaaaatca tgctgctatt attgctgtga   7260
aattgtataa agattaggat tcatgccagt ttttatttta aaaaataatg tgcattttaa   7320
gggtttatat ttagaaaaaa ataaaatgtt tcaagaacaa cacattgata tgtggaaata   7380
ttctataagg ttttctttg ttcccttaga attcattgga gggatgcagt aaaaactgta   7440
gtagaaacct tgaaacaccc atatgtgaaa aggtctgtgg aaattgaggc ctctacatta   7500
aaagtgcaga accaactgtt ttacagtcaa agtgctagga aacctgatag gatacttccc   7560
tttggcacaa aaacaccctg ggtgctacat acaggagtat gacctttggt gaatatgtgg   7620
cactaatttt ttttacctta atcatattct tgtcaagtag gcaacccatt gccccttgga   7680
gaccacacca gccctgtaag ttctcaccag cagcatggag attaggaaga ggggctgctg   7740
tgaccaggag atacacacgg ctttaagtaa ctgagagcct aaagaaagta acccagggag   7800
tccggtccag ttttaatatt tgtggatttg ttgtcacaca cattgtttag tcctgaaact   7860
aaaacctatt ttataaatag tagggttaat tcctcgaaac aatttcttta ttaataaatg   7920
tcctgtgggt ttagaaatat caggtaaata tttgaataca gaatgatgat tgcaattact   7980
```

```
gttacaagcg tgaaacacaa acttcagatc aaatctagag ttgcttcatt taatgcatgc   8040
tagcaacagc cttaactttg gattcagtta tttgaaacac ttttccggca tctttccctt   8100
tctaatgttg tggggtggaa accggatggc aaatcactgt gagccggata cctcagcaca   8160
gtccaccttg tgtgtgactt cacaaatggg ggacttcaca aatggggtaa ctgaatgtta   8220
ttactttcaa attttgacat ggagcattat gatcaaggaa atggagctgc cttatacatt   8280
aaacccgtga tttaatccta ttgacatttt catagccatg cctccagatt ttatcttttt   8340
ggcaaaattc tgattccaca gtttggtctg attgaaataa atattccctg gacgtctggc   8400
taaaaatttt gctaacaatc ccagaggtgc cattttctta ttaataaatt tcattggagc   8460
cttatttctt actatattca atttcgtttc aaacctgcaa gtccctggga tggtcccacg   8520
actagggcct gcacatttct tacaatggca aagcattttt taaaatttag ggtcaggttg   8580
aaaaattcta ggactaattc tgtagagagg agggactgtt aactaacgtg agtggggacg   8640
gaggagtagg ttaccacatt tggagcagta atagatgcaa acgatgtaaa tttgaaattt   8700
gcccctttag ttaaagaagg agcctgcaaa gtccatttct ctgttttcag ccctgtcagt   8760
cacccattta ggatgttggc aaagtactgc ttgagcagaa tgtgtaagaa agtaataatg   8820
aaagcaaaag tatgtcagac agttacttct tccacatggt tagaggcatg tgattttcag   8880
cactgtgtgt tacagaaatg tcaggaatgg tgtattataa cgtgtgcaag ataatgtcag   8940
tgtgcacaga gggtcttttt tccttatctg attagtactg ttaatgttca aagaataaaa   9000
atggttttac agtttagatt ctgagatagc aaaacctgat tttcaacca tgacctgcat    9060
gagagaagca tcctaggaag tcttagatca tacttttgag tttttaattt taatttatat   9120
agtgtttttt tatgtcttaa tatttttgtg aactggtgta aattgttaat gcatataagc   9180
ttgtgtattt ttgtaaatag ttttgtgatt tatttcttgc cccatatgta aatatttaga   9240
gtctcatttc ttgcaaactt atttgaagct gagttgtggg tttgggtttt gtttgtttct   9300
ttggttgcag ggtggggtgg ggggtggcag gggagggagg aagggatttt tgtacctgga   9360
gatggagata tcttgtggtt taaagcaaat gtcccactga aagtgattca aatatcaaca   9420
gaattatttc aggttaaaac aga                                           9443
```

<210> SEQ ID NO 12
<211> LENGTH: 1738
<212> TYPE: PRT
<213> ORGANISM: Homo sapiens

<400> SEQUENCE: 12

```
Met Lys Ser Arg Pro Thr Lys Gln Lys Leu Lys Gln Arg Gly Ile Leu
1               5                   10                  15

Lys Glu Arg Val Phe Gly Cys Asp Leu Gly Glu His Leu Leu Asn Ser
            20                  25                  30

Gly Phe Glu Val Pro Gln Val Leu Gln Ser Cys Thr Ala Phe Ile Glu
        35                  40                  45

Arg Tyr Gly Ile Val Asp Gly Ile Tyr Arg Leu Ser Gly Val Ala Ser
    50                  55                  60

Asn Ile Gln Arg Leu Arg His Glu Phe Asp Ser Glu His Val Pro Asp
65                  70                  75                  80

Leu Thr Lys Glu Pro Tyr Val Gln Asp Ile His Ser Val Gly Ser Leu
                85                  90                  95

Cys Lys Leu Tyr Phe Arg Glu Leu Pro Asn Pro Leu Leu Thr Tyr Gln
            100                 105                 110
```

```
Leu Tyr Glu Lys Phe Ser Asp Ala Val Ser Ala Ala Thr Asp Glu Glu
        115                 120                 125

Arg Leu Ile Lys Ile His Asp Val Ile Gln Gln Leu Pro Pro Pro His
    130                 135                 140

Tyr Arg Thr Leu Glu Phe Leu Met Arg His Leu Ser Leu Leu Ala Asp
145                 150                 155                 160

Tyr Cys Ser Ile Thr Asn Met His Ala Lys Asn Leu Ala Ile Val Trp
                165                 170                 175

Ala Pro Asn Leu Leu Arg Ser Lys Gln Ile Glu Ser Ala Cys Phe Ser
            180                 185                 190

Gly Thr Ala Ala Phe Met Glu Val Arg Ile Gln Ser Val Val Val Glu
        195                 200                 205

Phe Ile Leu Asn His Val Asp Val Leu Phe Ser Gly Arg Ile Ser Met
    210                 215                 220

Ala Met Gln Glu Gly Ala Ala Ser Leu Ser Arg Pro Lys Ser Leu Leu
225                 230                 235                 240

Val Ser Ser Pro Ser Thr Lys Leu Leu Thr Leu Glu Glu Ala Gln Ala
                245                 250                 255

Arg Thr Gln Ala Gln Val Asn Ser Pro Ile Val Thr Glu Asn Lys Tyr
            260                 265                 270

Ile Glu Val Gly Glu Gly Pro Ala Ala Leu Gln Gly Lys Phe His Thr
        275                 280                 285

Ile Ile Glu Phe Pro Leu Glu Arg Lys Arg Pro Gln Asn Lys Met Lys
    290                 295                 300

Lys Ser Pro Val Gly Ser Trp Arg Ser Phe Phe Asn Leu Gly Lys Ser
305                 310                 315                 320

Ser Ser Val Ser Lys Arg Lys Leu Gln Arg Asn Glu Ser Glu Pro Ser
                325                 330                 335

Glu Met Lys Ala Met Ala Leu Lys Gly Gly Arg Ala Glu Gly Thr Leu
            340                 345                 350

Arg Ser Ala Lys Ser Glu Glu Ser Leu Thr Ser Leu His Ala Val Asp
        355                 360                 365

Gly Asp Ser Lys Leu Phe Arg Pro Arg Arg Pro Arg Ser Ser Ser Asp
    370                 375                 380

Ala Leu Ser Ala Ser Phe Asn Gly Glu Met Leu Gly Asn Arg Cys Asn
385                 390                 395                 400

Ser Tyr Asp Asn Leu Pro His Asp Asn Glu Ser Glu Glu Glu Gly Gly
                405                 410                 415

Leu Leu His Ile Pro Ala Leu Met Ser Pro His Ser Ala Glu Asp Val
            420                 425                 430

Asp Leu Ser Pro Pro Asp Ile Gly Val Ala Ser Leu Asp Phe Asp Pro
        435                 440                 445

Met Ser Phe Gln Cys Ser Pro Pro Lys Ala Glu Ser Glu Cys Leu Glu
    450                 455                 460

Ser Gly Ala Ser Phe Leu Asp Ser Pro Gly Tyr Ser Lys Asp Lys Pro
465                 470                 475                 480

Ser Ala Asn Lys Lys Asp Ala Glu Thr Gly Ser Ser Gln Cys Gln Thr
                485                 490                 495

Pro Gly Ser Thr Ala Ser Ser Glu Pro Val Ser Pro Leu Gln Glu Lys
            500                 505                 510

Leu Ser Pro Phe Phe Thr Leu Asp Leu Ser Pro Thr Glu Asp Lys Ser
        515                 520                 525
```

-continued

```
Ser Lys Pro Ser Ser Phe Thr Glu Lys Val Val Tyr Ala Phe Ser Pro
    530                 535                 540

Lys Ile Gly Arg Lys Leu Ser Lys Ser Pro Ser Met Ser Ile Ser Glu
545                 550                 555                 560

Pro Ile Ser Val Thr Leu Pro Pro Arg Val Ser Glu Val Ile Gly Thr
                565                 570                 575

Val Ser Asn Thr Thr Ala Gln Asn Ala Ser Ser Ser Thr Trp Asp Lys
            580                 585                 590

Cys Val Glu Glu Arg Asp Ala Thr Asn Arg Ser Pro Thr Gln Ile Val
        595                 600                 605

Lys Met Lys Thr Asn Glu Thr Val Ala Gln Glu Ala Tyr Glu Ser Glu
    610                 615                 620

Val Gln Pro Leu Asp Gln Val Ala Ala Glu Glu Val Glu Leu Pro Gly
625                 630                 635                 640

Lys Glu Asp Gln Ser Val Ser Ser Ser Gln Ser Lys Ala Val Ala Ser
                645                 650                 655

Gly Gln Thr Gln Thr Gly Ala Val Thr His Asp Pro Pro Gln Asp Ser
            660                 665                 670

Val Pro Val Ser Ser Val Ser Leu Ile Pro Pro Pro Pro Pro Pro Lys
        675                 680                 685

Asn Val Ala Arg Met Leu Ala Leu Ala Leu Ala Glu Ser Ala Gln Gln
    690                 695                 700

Ala Ser Thr Gln Ser Leu Lys Arg Pro Gly Thr Ser Gln Ala Gly Tyr
705                 710                 715                 720

Thr Asn Tyr Gly Asp Ile Ala Val Ala Thr Thr Glu Asp Asn Leu Ser
                725                 730                 735

Ser Ser Tyr Ser Ala Val Ala Leu Asp Lys Ala Tyr Phe Gln Thr Asp
            740                 745                 750

Arg Pro Ala Glu Gln Phe His Leu Gln Asn Asn Ala Pro Gly Asn Cys
        755                 760                 765

Asp His Pro Leu Pro Glu Thr Thr Ala Thr Gly Asp Pro Thr His Ser
    770                 775                 780

Asn Thr Thr Glu Ser Gly Glu Gln His His Gln Val Asp Leu Thr Gly
785                 790                 795                 800

Asn Gln Pro His Gln Ala Tyr Leu Ser Gly Asp Pro Glu Lys Ala Arg
                805                 810                 815

Ile Thr Ser Val Pro Leu Asp Ser Glu Lys Ser Asp Asp His Val Ser
            820                 825                 830

Phe Pro Glu Asp Gln Ser Gly Lys Asn Ser Met Pro Thr Val Ser Phe
        835                 840                 845

Leu Asp Gln Asp Gln Ser Pro Pro Arg Phe Tyr Ser Gly Asp Gln Pro
    850                 855                 860

Pro Ser Tyr Leu Gly Ala Ser Val Asp Lys Leu His His Pro Leu Glu
865                 870                 875                 880

Phe Ala Asp Lys Ser Pro Thr Pro Pro Asn Leu Pro Ser Asp Lys Ile
                885                 890                 895

Tyr Pro Pro Ser Gly Ser Pro Glu Glu Asn Thr Ser Thr Ala Thr Met
            900                 905                 910

Thr Tyr Met Thr Thr Thr Pro Ala Thr Ala Gln Met Ser Thr Lys Glu
        915                 920                 925

Ala Ser Trp Asp Val Ala Glu Gln Pro Thr Thr Ala Asp Phe Ala Ala
    930                 935                 940
```

```
Ala Thr Leu Gln Arg Thr His Arg Thr Asn Arg Pro Leu Pro Pro Pro
945                 950                 955                 960

Pro Ser Gln Arg Ser Ala Glu Gln Pro Pro Val Val Gly Gln Val Gln
                965                 970                 975

Ala Ala Thr Asn Ile Gly Leu Asn Asn Ser His Lys Val Gln Gly Val
            980                 985                 990

Val Pro Val Pro Glu Arg Pro Pro  Glu Pro Arg Ala Met  Asp Asp Pro
        995                 1000                 1005

Ala Ser  Ala Phe Ile Ser Asp  Ser Gly Ala Ala Ala  Ala Gln Cys
    1010                 1015                 1020

Pro Met  Ala Thr Ala Val Gln  Pro Gly Leu Pro Glu  Lys Val Arg
    1025                 1030                 1035

Asp Gly  Ala Arg Val Pro Leu  Leu His Leu Arg Ala  Glu Ser Val
    1040                 1045                 1050

Pro Ala  His Pro Cys Gly Phe  Pro Ala Pro Leu Pro  Pro Thr Arg
    1055                 1060                 1065

Met Met  Glu Ser Lys Met Ile  Ala Ala Ile His Ser  Ser Ser Ala
    1070                 1075                 1080

Asp Ala  Thr Ser Ser Ser Asn  Tyr His Ser Phe Val  Thr Ala Ser
    1085                 1090                 1095

Ser Thr  Ser Val Asp Asp Ala  Leu Pro Leu Pro Leu  Pro Val Pro
    1100                 1105                 1110

Gln Pro  Lys His Ala Ser Gln  Lys Thr Val Tyr Ser  Ser Phe Ala
    1115                 1120                 1125

Arg Pro  Asp Val Thr Thr Glu  Pro Phe Gly Pro Asp  Asn Cys Leu
    1130                 1135                 1140

His Phe  Asn Met Thr Pro Asn  Cys Gln Tyr Arg Pro  Gln Ser Val
    1145                 1150                 1155

Pro Pro  His His Asn Lys Leu  Glu Gln His Gln Val  Tyr Gly Ala
    1160                 1165                 1170

Arg Ser  Glu Pro Pro Ala Ser  Met Gly Leu Arg Tyr  Asn Thr Tyr
    1175                 1180                 1185

Val Ala  Pro Gly Arg Asn Ala  Ser Gly His His Ser  Lys Pro Cys
    1190                 1195                 1200

Ser Arg  Val Glu Tyr Val Ser  Ser Leu Ser Ser Ser  Val Arg Asn
    1205                 1210                 1215

Thr Cys  Tyr Pro Glu Asp Ile  Pro Pro Tyr Pro Thr  Ile Arg Arg
    1220                 1225                 1230

Val Gln  Ser Leu His Ala Pro  Pro Ser Ser Met Ile  Arg Ser Val
    1235                 1240                 1245

Pro Ile  Ser Arg Thr Glu Val  Pro Pro Asp Asp Glu  Pro Ala Tyr
    1250                 1255                 1260

Cys Pro  Arg Pro Leu Tyr Gln  Tyr Lys Pro Tyr Gln  Ser Ser Gln
    1265                 1270                 1275

Ala Arg  Ser Asp Tyr His Val  Thr Gln Leu Gln Pro  Tyr Phe Glu
    1280                 1285                 1290

Asn Gly  Arg Val His Tyr Arg  Tyr Ser Pro Tyr Ser  Ser Ser Ser
    1295                 1300                 1305

Ser Ser  Tyr Tyr Ser Pro Asp  Gly Ala Leu Cys Asp  Val Asp Ala
    1310                 1315                 1320

Tyr Gly  Thr Val Gln Leu Arg  Pro Leu His Arg Leu  Pro Asn Arg
    1325                 1330                 1335
```

-continued

```
Asp Phe  Ala Phe Tyr Asn Pro  Arg Leu Gln Gly Lys  Ser Leu Tyr
    1340                 1345                 1350

Ser Tyr  Ala Gly Leu Ala Pro  Arg Pro Arg Ala Asn  Val Thr Gly
    1355                 1360                 1365

Tyr Phe  Ser Pro Asn Asp His  Asn Val Val Ser Met  Pro Pro Ala
    1370                 1375                 1380

Ala Asp  Val Lys His Thr Tyr  Thr Ser Trp Asp Leu  Glu Asp Met
    1385                 1390                 1395

Glu Lys  Tyr Arg Met Gln Ser  Ile Arg Arg Glu Ser  Arg Ala Arg
    1400                 1405                 1410

Gln Lys  Val Lys Gly Pro Val  Met Ser Gln Tyr Asp  Asn Met Thr
    1415                 1420                 1425

Pro Ala  Val Gln Asp Asp Leu  Gly Gly Ile Tyr Val  Ile His Leu
    1430                 1435                 1440

Arg Ser  Lys Ser Asp Pro Gly  Lys Thr Gly Leu Leu  Ser Val Ala
    1445                 1450                 1455

Glu Gly  Lys Glu Ser Arg His  Ala Ala Lys Ala Ile  Ser Pro Glu
    1460                 1465                 1470

Gly Glu  Asp Arg Phe Tyr Arg  Arg His Pro Glu Ala  Glu Met Asp
    1475                 1480                 1485

Arg Ala  His His His Gly Gly  His Gly Ser Thr Gln  Pro Glu Lys
    1490                 1495                 1500

Pro Ser  Leu Pro Gln Lys Gln  Ser Ser Leu Arg Ser  Arg Lys Leu
    1505                 1510                 1515

Pro Asp  Met Gly Cys Ser Leu  Pro Glu His Arg Ala  His Gln Glu
    1520                 1525                 1530

Ala Ser  His Arg Gln Phe Cys  Glu Ser Lys Asn Gly  Pro Pro Tyr
    1535                 1540                 1545

Pro Gln  Gly Ala Gly Gln Leu  Asp Tyr Gly Ser Lys  Gly Ile Pro
    1550                 1555                 1560

Asp Thr  Ser Glu Pro Val Ser  Tyr His Asn Ser Gly  Val Lys Tyr
    1565                 1570                 1575

Ala Ala  Ser Gly Gln Glu Ser  Leu Arg Leu Asn His  Lys Glu Val
    1580                 1585                 1590

Arg Leu  Ser Lys Glu Met Glu  Arg Pro Trp Val Arg  Gln Pro Ser
    1595                 1600                 1605

Ala Pro  Glu Lys His Ser Arg  Asp Cys Tyr Lys Glu  Glu Glu His
    1610                 1615                 1620

Leu Thr  Gln Ser Ile Val Pro  Pro Pro Lys Pro Glu  Arg Ser His
    1625                 1630                 1635

Ser Leu  Lys Leu His His Thr  Gln Asn Val Glu Arg  Asp Pro Ser
    1640                 1645                 1650

Val Leu  Tyr Gln Tyr Gln Pro  His Gly Lys Arg Gln  Ser Ser Val
    1655                 1660                 1665

Thr Val  Val Ser Gln Tyr Asp  Asn Leu Glu Asp Tyr  His Ser Leu
    1670                 1675                 1680

Pro Gln  His Gln Arg Gly Val  Phe Gly Gly Gly Gly  Met Gly Thr
    1685                 1690                 1695

Tyr Val  Pro Pro Gly Phe Pro  His Pro Gln Ser Arg  Thr Tyr Ala
    1700                 1705                 1710
```

```
Thr Ala  Leu Gly Gln Gly Ala  Phe Leu Pro Ala Glu  Leu Ser Leu
    1715                1720                1725

Gln His  Pro Glu Thr Gln Ile  His Ala Glu
    1730                1735


<210> SEQ ID NO 13
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 13

cgaccatggc tgtagactgt ta                                         22


<210> SEQ ID NO 14
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 14

ggccgtgact ggagactgtt a                                          21
```

MODULATION OF HUMAN CYTOMEGALOVIRUS REPLICATION BY MICRO-RNA 132 (MIR132), MICRO-RNA 145 (MIR145) AND MICRO-RNA 212 (MIR212)

RELATED APPLICATIONS

This application is a divisional of U.S. patent application Ser. No. 14/563,512, filed Dec. 8, 2014, which is a divisional of U.S. patent application Ser. No. 13/227,117 (now U.S. Pat. No. 8,933,045), filed Sep. 7, 2011, which is a continuation of International Application No. PCT/US2010/027040, filed Mar. 11, 2010. PCT/US2010/027040 claims priority to U.S. Provisional Patent Application No. 61/159,391, filed Mar. 11, 2009, and to U.S. Provisional Patent Application No. 61/159,420, filed Mar. 11, 2009. The entire contents of each of the foregoing applications are incorporated herein by reference.

SEQUENCE LISTING

The instant application contains a Sequence Listing which has been submitted electronically in ASCII format and is hereby incorporated by reference in its entirety. Said ASCII copy, created on Dec. 19, 2016, is named SL_122274_14604.txt and is 66,522 bytes in size.

BACKGROUND OF THE INVENTION

RNAs that do not function as messenger RNAs, transfer RNAs or ribosomal RNAs are collectively termed non-coding RNAs (ncRNAs). ncRNAs can range in size from 21-25 nucleotides (nt) up to >10,000 nt, and estimates for the number of ncRNAs per genome range from hundreds to thousands. The functions of ncRNAs, although just beginning to be revealed, appear to vary widely from the purely structural to the purely regulatory, and include effects on transcription, translation, mRNA stability and chromatin structure (G. Storz, *Science* (2002) 296:1260-1262). Two recent pivotal discoveries have placed ncRNAs in the spotlight: the identification of large numbers of very small ncRNAs of 20-24 nucleotides in length, termed micro RNAs (miRNAs), and the relationship of these miRNAs to intermediates in a eukaryotic RNA silencing mechanism known as RNA interference (RNAi).

RNA silencing refers to a group of sequence-specific, RNA-targeted gene-silencing mechanisms common to animals, plants, and some fungi, wherein RNA is used to target and destroy homologous mRNA, viral RNA, or other RNAs. RNA silencing was first observed in plants, where it was termed posttranscriptional gene silencing (PTGS). A similar phenomenon observed in Fungi was termed quelling. These phenomena were subsequently found to be related to a process in animals called RNA interference (RNAi). In RNAi, experimentally introduced double-stranded RNA (dsRNA) leads to loss of expression of the corresponding cellular gene. A key step in the molecular mechanism of RNAi is the processing of dsRNA by the ribonuclease Dicer into short dsRNAs, called small interfering RNAs (siRNAs), of ~21-23 nt in length having specific features including 2 nt 3'-overhangs, a 5'-phosphate group and 3'-hydroxyl group. siRNAs are incorporated into a large nucleoprotein complex called an RNA-induced silencing complex (RISC). A distinct ribonuclease component of RISC uses the sequence encoded by the antisense strand of the siRNA as a guide to find and then cleave mRNAs of complementary sequence. The cleaved mRNA is ultimately degraded by cellular exonucleases. Thus, in PTGS, quelling, and RNAi, the silenced gene is transcribed normally into mRNA, but the mRNA is destroyed as quickly as it is made. In plants, it appears that PTGS evolved as a defense strategy against viral pathogens and transposons. While the introduction of long dsRNAs into plants and invertebrates initiates specific gene silencing (Hannon, 2002; Hutvagner, 2002), in mammalian cells, long dsRNA can induce the potent translational inhibitory effects of the interferon response (Samuel, 2001). Short dsRNAs of <30 bp, however, evade the interferon response and are successfully incorporated into RISC to induce RNAi (Zamore et al., Cell, 101(1):25-33 (2000); Elbashir, 2001).

Another group of small ncRNAs, called micro RNAs (miRNAs), are related to the intermediates in RNAi and appear to be conserved from flies to humans (Lau, 2001; Lagos-Quintana, 2001; Rhoades, 2002). To date, all metazoans examined have been found to encode miRNAs. MicroRNAs are initially transcribed as a long, single-stranded miRNA precursor known as a pri-miRNA, which may contain one or several miRNAs, and these transcripts are then processed to ~70 nt pre-miRNAs having a predicted stem-loop structure. The enzyme Dicer cleaves pre-miRNA to produce ~20-25 nt miRNAs that function as single-stranded RNAi mediators capable of directing gene silencing (Hutvagner, 2002; McManus, 2002). These small transcripts have been proposed to play a role in development, apparently by suppressing target genes to which they have some degree of complementarity. The canonical miRNAs lin-4 and let-7 influence gene expression by binding to sequences of partial complementarity in the 3' UTR of mRNA, thereby preventing mRNA translation (McCaffrey, 2002). In recent studies, however, miRNAs bearing perfect complementarity to a target RNA could function analogously to siRNAs, specifically directing degradation of the target sequences (Hutvagner, 2002b; Llave, 2002). Thus, the degree of complementarity between an miRNA and its target may determine whether the miRNA acts as a translational repressor or as a guide to induce mRNA cleavage. The discovery of miRNAs as endogenous small regulatory ncRNAs may represent the tip of an iceberg, as other groups of regulatory ncRNAs likely remain to be discovered.

Numerous recent studies have highlighted the importance of miRNAs in regulating gene expression. miRNAs can "fine-tune" gene expression by binding to nearly perfect complementary sequences in mRNAs, thus preventing their translation. The importance of miRNAs in the regulation of specific genes has been demonstrated in a variety of organisms, where their function impacts such universal cellular pathways as cell death, development, proliferation, and hematopoiesis (Ambros, 2004). Additionally, it has been demonstrated that several animal viruses encode their own miRNAs, which target either cellular or viral mRNAs (Cullen, 2006; Nair, 2006; Sarnow, 2006). Recent studies have further underscored the critical role of miRNAs in the maintenance of cellular homeostasis by demonstrating that miRNAs are misregulated in various forms of cancer. Furthermore, specific tumor types have been found to have specific patterns of miRNA expression, or "miRNA signatures" (Calin, 2006; Calin, 2002; Volinia, 2006; Yanaihara, 2006).

The discovery of particular miRNAs that display altered patterns of expression during other disease conditions would help elucidate the role of specific cellular miRNAs and their corresponding target genes is pathogenesis. Such miRNAs could be used, for example, as therapeutic and diagnostic targets.

SUMMARY OF THE INVENTION

The present invention is based, at least in part, on the surprising discovery that miR145 is significantly downregulated during HCMV infection. The present invention is based on the further discovery that transfection of fibroblasts with a miR145 mimetic prior to HCMV infection reduced HCMV replication, and likewise reduced expression of the HCMV proteins Immediate Early 2 (IE-2), the Early (E) protein pp65, and the Late (L) protein gB55. This discovery implicates miR145 in HCMV pathogenesis and replication.

In another embodiment, the present invention is based, at least in part, on the surprising discovery that miR132 and miR212 are significantly upregulated during HCMV infection. The present invention is based on the further discovery that transfection of fibroblasts with an antisense miR132 and/or antisense miR212 locked nucleic acid (LNA) prior to HCMV infection reduced HCMV replication, and likewise reduced expression of the HCMV proteins Immediate Early 2 (IE-2), the Early (E) protein pp65, and the Late (L) protein gB55. This discovery implicates miR132 in HCMV pathogenesis and replication.

Accordingly, in one aspect, the present invention features methods of inhibiting HCMV replication in a cell or organism, comprising contacting the cell or organism with a miR145 agent in an amount effective to decrease the level of one or more miR145 targets, such that HCMV replication is inhibited. In another aspect, the invention features methods of inhibiting HCMV replication in a cell or organism, comprising contacting the cell or organism with an RNA silencing agent capable of mediating RNAi of a miR145 target in an amount effective to decrease the level of the miR145 target, such that HCMV replication is inhibited. In certain embodiments, the miR145 agent or the RNA silencing agent are administered to an organism to treat or ameliorate the symptoms of an HCMV infection. In some embodiments, the miR145 agent or the RNA silencing agent are administered to an organism in combination with an additional agent, e.g., an antiviral agent.

In another aspect, the invention features kits that contain a composition comprising a miR145 agent and instructions for administration of the composition to a subject for the treatment of HCMV. In another aspect, the invention features kits that contain a composition comprising an RNA silencing agent capable of reducing expression of a miR145 target, and instructions for administration of the composition to a subject for the treatment of HCMV. In some embodiments, the kits further contain an additional agent, e.g., an antiviral agent.

In another aspect, the invention features a method of detecting an HCMV infection in a subject by determining a level of miR145 expression in a subject, and comparing the level of miR145 expression to a suitable control, wherein a reduction in the level of miR145 expression relative to the suitable control indicates the presence of an HCMV infection in the subject.

In one aspect, the present invention features methods of inhibiting HCMV replication in a cell or organism, comprising contacting the cell or organism with a miR132 antagonist and/or a miR212 antagonist in an amount effective to decrease the level of one or more miR132 targets and/or miR212 targets, such that HCMV replication is inhibited. In another aspect, the invention features methods of inhibiting HCMV replication in a cell or organism, comprising contacting the cell or organism with a miR132 target activating agent in an amount effective to increase the level of a miR132 target, such that HCMV replication is inhibited. In another aspect, the invention features methods of inhibiting HCMV replication in a cell or organism, comprising contacting the cell or organism with a miR212 target activating agent in an amount effective to increase the level of a miR212 target, such that HCMV replication is inhibited. In certain embodiments, the miR132 antagonist, the miR212 antagonist, the miR132 target activating agent, or the miR212 target activating agent are administered to an organism to treat or ameliorate the symptoms of an HCMV infection. In some embodiments, the miR132 antagonist, the miR212 antagonist, the miR132 target activating agent, or the miR212 target activating agent are administered to an organism in combination with an additional agent, e.g., an antiviral agent.

In another aspect, the invention features kits that contain a composition comprising a miR132 antagonist, a miR212 antagonist, or combinations thereof, and instructions for administration of the composition to a subject for the treatment of HCMV. In another aspect, the invention features kits that contain a composition comprising a miR132 target activating agent capable of reducing expression of a miR132 target, a miR212 target activating agent capable of reducing expression of a miR212 target, or combinations thereof, and instructions for administration of the composition to a subject for the treatment of HCMV. In some embodiments, the kits further contain an additional agent, e.g., an antiviral agent.

In another aspect, the invention features a method of detecting an HCMV infection in a subject by determining a level of miR132 expression and/or a level of miR212 expression in a subject, and comparing the level of miR132 and/or miR212 expression to a suitable control, wherein an increase in the level of miR132 and/or miR212 expression relative to the suitable control indicates the presence of an HCMV infection in the subject.

Other features and advantages of the invention will be apparent from the following detailed description, and from the claims.

BRIEF DESCRIPTION OF THE DRAWINGS

FIG. 20A depicts the nucleic acid sequence and structure of the mature stem-loop form of miR132 (hsa-miR-132; SEQ ID NO:3).

FIG. 20B depicts the nucleic acid sequence of the mature (processed) form of miR132 (hsa-miR-132; SEQ ID NO:4).

FIG. 20C depicts the nucleic acid sequence and structure of the mature stem-loop form of miR212 (hsa-miR-212; SEQ ID NO:5).

FIG. 20D depicts the nucleic acid sequence and structure of the mature (processed) form of miR212 (hsa-miR212; SEQ ID NO:6)

FIG. 21A-FIG. 21B depict the nucleic acid sequence of IRS-1 (SEQ ID NO:7; gi187761322).

FIG. 22A-FIG. 22B depict the nucleic acid sequence of MAPK (SEQ ID NO:8; gi75709178).

FIG. 23A-FIG. 23C depict the nucleic acid sequence of MeCP2 (SEQ ID NO:9; gi160707948).

FIG. 24 depicts the polypeptide sequence of MeCP2 (SEQ ID NO:10; gi4826830).

FIG. 25A-FIG. 25C depict the nucleic acid sequence of RICS (SEQ ID NO:11; gi218083782).

FIG. 26 depicts the polypeptide sequence of RICS (SEQ ID NO:12; gi29469071).

DETAILED DESCRIPTION OF THE INVENTION

Figure 1:
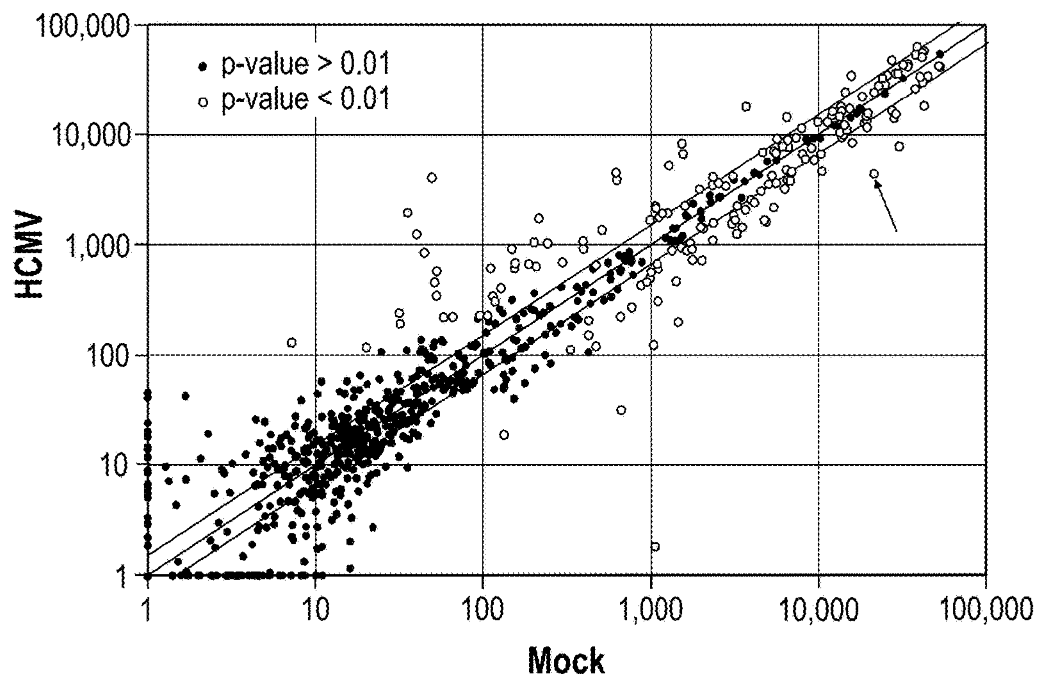
FIG. 1 graphically depicts the alteration in miR145 expression following HCMV infection in HEL fibroblasts, as determined by microarray analysis.

The present invention is based in part on the discovery that miR145 is significantly downregulated during HCMV infection, and miR132 and miR212 are significantly upregulated during HCMV infection. The instant inventors further discovered that transfection of fibroblasts with a miR145 mimic prior to HCMV infection reduced HCMV replication, and likewise reduced expression of the HCMV proteins Immediate Early 2 (IE-2), the Early (E) protein pp65, and the Late (L) protein gB55. In addition, transfection of fibroblasts with a miR132 antagonist and/or a miR212 antagonist prior to HCMV infection reduced HCMV replication, and reduced expression of the HCMV proteins Immediate Early 2 (IE-2), the Early (E) protein pp65, and the Late (L) protein gB55. This discovery implicates miR145, miR132, and miR212 during HCMV IE, E, and L gene expression, indicating that the foregoing microRNAs have a role in HCMV pathogenesis and replication. HCMV infection was shown to upregulate the miR145 target molecule Insulin Receptor Substrate-1 (IRS-1) in fibroblasts, and to alter IRS-1 localization, implicating downstream targets of miR145 in HCMV pathogenesis. HCMV infection was also shown to downregulate the miR132 and miR212 target molecule MeCP2 in fibroblasts, implicating downstream targets of miR132 and miR212 in HCMV pathogenesis. These findings indicate that miR145, miR132, and miR212 are important cellular mediator of HCMV infection. Misregulation of these miRNAs by HCMV also indicates that the cellular or viral targets of these miRNAs will likewise be aberrantly regulated during infection.

The concept that HCMV specifically modifies cellular miR145, miR132, and miR212 expression represents a hitherto unidentified mechanism by which HCMV produces an environment conducive to infection. The finding that disruption of miR145 downregulation, and/or miR132 or miR212 upregulation, results in attenuation of viral infection thus provides novel anti-viral approaches.

Cellular and/or viral genes or gene products whose expression is altered as a consequence of miR145 downregulation following HCMV infection make attractive targets for novel therapeutic anti-viral strategies. Such strategies include, for example, administration of a compound that increases or mimics expression of miR145. Such a compound may include, for example, an expression vector, a recombinant miRNA, or a miRNA mimic. Likewise, cellular and/or viral genes or gene products whose expression is altered as a consequence of miR132 or miR212 upregulation following HCMV infection make attractive targets for novel therapeutic anti-viral strategies. Such strategies include, for example, administration of a compound that antagonizes or reduces expression of miR132 and/or miR212. Such a compound may include, for example, an antisense miR132 LNA, an antisense miR212 LNA, an antagomir, a 2'O-methyl antisense miR132 RNA, or a 2'O-methyl antisense miR212 RNA.

As the genes or gene products targeted by miR145 are expressed at elevated levels in HCMV infected cells due to the HCMV-mediated reduction in expression of miR145, such anti-viral strategies also include, for example, administration of a compound that inhibits or reduces expression of a gene or gene product that is targeted by miR145. Such a compound may include, for example, an siRNA, an miRNA, a shRNA, an antisense nucleic acid molecule, or a ribozyme.

As the genes or gene products targeted by miR132 and/or miR212 are expressed at reduced levels in HCMV infected cells due to the HCMV-mediated increase in expression of miR132 and miR212, such anti-viral strategies also include, for example, administration of a compound that increases, upregulates, or mimics expression of a gene or gene product that is targeted by miR132 or miR212. Such a compound may include, for example, an expression vector encoding a miR132 target or a miR212 target, an RNA transcript encoding a miR132 target or a miR212 target, a miR132 target polypeptide, a miR212 target polypeptide, a recombinant miR132 target polypeptide, a recombinant miR212 target polypeptide, or an active domain thereof.

Accordingly, the invention provides, in a first aspect, a method of inhibiting HCMV replication in a cell, comprising contacting the cell with a miR145 agent in an amount effective to decrease the level of one or more miR145 targets, such that HCMV replication is inhibited. In one embodiment of this aspect, the miR145 agent is a miR145 mimic, a synthetic miR145 oligonucleotide, and an expression vector encoding miR145. In an exemplary embodiment, the agent contains a nucleic acid molecule comprising the nucleotide sequence of SEQ ID NO:1. In another exemplary embodiment, the agent contains a nucleic acid molecule comprising the nucleotide sequence of SEQ ID NO:2.

In certain embodiments of the foregoing aspect, the level of one or more miR145 targets is determined by measuring the level of expression of a miR145 target, and comparing the level of expression to a suitable control. In particular embodiments, the measuring or determining the level of expression of a miR145 target may be performed using Western blot, ELISA, or antibody microarray. In other embodiments of the foregoing aspect, the level of one or more miR145 targets is determined by measuring the level of expression of the miR145 target, and comparing the level of expression to a suitable control. In particular embodiments, the miR145 target is an mRNA, e.g., an mRNA encoding a polypeptide. Accordingly, in some embodiments, measuring the level of expression of the miR145 target may be performed using Northern blot, quantitative Real Time PCR (qRT-PCR), or microarray. In exemplary embodiments of the foregoing aspects, the miR145 target is IRS-1 (e.g., an IRS-1 polypeptide, an mRNA encoding an IRS-1 polypeptide).

In certain embodiments of the foregoing aspects, the cell is in a organism. In some embodiments, the organism is infected with HCMV. In other embodiments, the organism is at risk of developing an HCMV infection. In some embodiments, the decrease in the level of one or more miR145 targets occurs in a cell contacted by the miR145 agent.

In another aspect, the invention provides methods of inhibiting HCMV replication in a cell, comprising contacting the cell with an RNA silencing agent capable of mediating RNAi of a miR145 target in an amount effective to decrease the level of the miR145 target, such that HCMV replication is inhibited. In exemplary embodiments, the RNA silencing agent is selected from the group consisting of an siRNA, a shRNA, an antisense RNA, and a ribozyme. In particular embodiments, the RNA silencing agent is at least 90% complementary to a portion of the miR145 target.

In certain embodiments of the foregoing aspect, the level of a miR145 target is determined by measuring the level of expression of a polypeptide encoded by the miR145 target, and comparing the level of expression to a suitable control. In some embodiments, measuring or determining the level of expression of a polypeptide encoded by the miR145 target is performed using Western blot, ELISA, or antibody microarray. In another embodiment of the foregoing aspect, the level of a miR145 target is determined by measuring the level of expression of a miR145 target, and comparing the level of expression to a suitable control. In particular embodiments, the miR145 target is an m RNA. In some embodiments, measuring or determining the level of expression of a miR145 target is performed using Northern blot, quantitative Real Time PCR (qRT-PCR), or microarray. In an exemplary embodiment, the miR145 target is an mRNA encoding IRS-1.

In some embodiments of the foregoing aspect, the cell is in an organism. In some embodiments, the organism is infected with HCMV. In other embodiments, the organism is at risk of developing an HCMV infection. In some embodiments, the decrease in the level of one or more miR145 targets occurs in a cell contacted by the miR145 agent.

In certain embodiments of the foregoing aspects, the miR145 target is selected based on having sequence complementarity with all or a portion of miR145 (SEQ ID NO:1, SEQ ID NO:2). In some embodiments, the miR145 target has a region of 6-8 contiguous nucleotides that are complementary to the seed region of miR145. In exemplary embodiments, the 6-8 contiguous nucleotides are located within the 3'UTR of the miR145 target. In other embodiments, the 6-8 contiguous nucleotides are located within an open reading frame of the miR145 target.

In some embodiments, the foregoing methods further involve contacting the cell with an additional therapeutic agent. In certain embodiments, the additional therapeutic agent is an antiviral agent. In exemplary embodiments, the antiviral agent is Ganciclovir, Valganciclovir, Cidofovir, Foscarnet, Formivirsen, Acyclovir, Valacyclovir, CMX001, Artesunate, BAY-384766, T-611, GW-275175X, or Maribavir.

In another aspect, the invention features methods of detecting an HCMV infection in a subject, comprising determining a level of miR145 expression in a subject, and comparing the level of miR145 expression to a suitable control, wherein a reduction in the level of miR145 expression relative to the suitable control indicates the presence of an HCMV infection in the subject.

In another aspect, the invention features kits comprising a composition containing a miR145 agent, and instructions for administration of the composition to a subject for the treatment of HCMV. In exemplary embodiments, the miR145 agent is a miR145 mimic, a synthetic miR145 oligonucleotide, or an expression vector encoding miR145.

In another aspect, the invention features kits comprising a composition containing an RNA silencing agent capable of reducing expression of a miR145 target, and instructions for administration of the composition to a subject for the treatment of HCMV. In some embodiments, the agent is an siRNA, a shRNA, an antisense RNA, or a ribozyme. In some embodiments, the miR145 target has a region of 6-8 contiguous nucleotides that are complementary to the seed region of miR145. In an exemplary embodiment, the miR145 target is an mRNA encoding IRS-1.

In one embodiment of the foregoing aspects, the kits further contain an additional agent, e.g., an antiviral agent. In exemplary embodiments, the antiviral agent is Ganciclovir, Valganciclovir, Cidofovir, Foscarnet, Formivirsen, Acyclovir, Valacyclovir, CMX001, Artesunate, BAY-384766, T-611, GW-275175X, or Maribavir, or combinations thereof.

In another aspect, the invention provides a method of inhibiting HCMV replication in a cell, comprising contacting the cell with a miR132 antagonist in an amount effective to increase the level of one or more miR132 targets, such that HCMV replication is inhibited. In another aspect, the invention provides a method of inhibiting HCMV replication in a cell, comprising contacting the cell with a miR212 antagonist in an amount effective to increase the level of one or more miR212 targets, such that HCMV replication is inhibited.

In some embodiments of the foregoing aspects, the antagonist is selected from the group consisting of an antisense locked nucleic acid (LNA), an antagomir, or a 2'O-methyl antisense RNA. In exemplary embodiments, the miR132 antagonist comprises a nucleic acid molecule that is complementary to all or a part of SEQ ID NO:3 or SEQ ID NO:4. In some embodiments, the miR132 antagonist is at least 70% complementary to all or a part of SEQ ID NO:3 or SEQ ID NO:4. In other exemplary embodiments, the miR212 antagonist comprises a nucleic acid molecule that is complementary to all or a part of SEQ ID NO:5 or SEQ ID NO:6. In some embodiments, the miR212 antagonist is at least 70% complementary to all or a part of SEQ ID NO:5 or SEQ ID NO:6.

In some embodiments of the foregoing aspects, the level of one or more targets is determined by measuring the level of expression of a polypeptide encoded by the target, and comparing the level of expression to a suitable control. In some embodiments, measuring the level of expression of a polypeptide encoded by the target is performed using a method selected from the group consisting of Western blot, ELISA, or antibody microarray. In other embodiments, the level of one or more targets is determined by measuring the level of expression of an RNA corresponding to the target, and comparing the level of expression to a suitable control. In particular embodiments, the RNA is an mRNA. In exemplary embodiments, measuring the level of expression of the target is performed using a method selected from the group consisting of Northern blot, quantitative Real Time PCR (qRT-PCR), or microarray.

In some embodiments of the foregoing aspects, the target is methyl CpG-binding protein 2 (MeCP2). In other embodiments, the target is Rho GTPase-activating protein (RICS). In some embodiments, the cell is in an organism, for example, an organism infected with HCMV. In some embodiments, the increase in the level of one or more targets occurs in a cell contacted by the antagonist.

In another aspect, the invention provides a method of inhibiting HCMV replication in a cell, comprising contacting the cell with a miR132 target activating agent in an amount effective to increase the level of a miR132 target, such that HCMV replication is inhibited. In one embodiment of this aspect, the miR132 target activating agent may be an expression vector encoding a miR132 target, a synthetic miR132 target RNA transcript, a miR132 target polypeptide, and a recombinant miR132 target polypeptide. In another aspect, the invention provides a method of inhibiting HCMV replication in a cell, comprising contacting the cell with a miR212 target activating agent in an amount effective to increase the level of a miR212 target, such that HCMV replication is inhibited. In one embodiment of this aspect, the miR212 target activating agent may be an expression vector encoding a miR212 target, a synthetic miR212 target RNA transcript, a miR212 target polypeptide, and a recombinant miR212 target polypeptide.

In one embodiment of the foregoing aspects, the level of the target is determined by measuring the level of expression of a polypeptide encoded by the target, and comparing the level of expression to a suitable control. In another embodiment, measuring the level of expression of a polypeptide encoded by the target is performed using Western blot, ELISA, or antibody microarray. In one embodiment, the level of one or more targets is determined by measuring the level of expression of an RNA corresponding to the target, and comparing the level of expression to a suitable control. In some embodiments, the RNA is a mRNA. In exemplary embodiments, measuring the level of expression of the target is performed using a method such as Northern blot, quantitative Real Time PCR (qRT-PCR), or microarray. In one embodiment of the foregoing aspects, the target is an mRNA encoding MeCP2. In another embodiment, the target is an mRNA encoding RICS. In one embodiment of the foregoing aspects, the cell is in an organism, for example, an organism infected with HCMV. In one embodiment, the increase in the level of one or more targets occurs in a cell contacted by the RNA agent.

In an exemplary embodiment of the foregoing aspects, the miR132 target is selected based on having sequence complementarity with all or a portion of SEQ ID NO:3 or SEQ ID NO:4. In another exemplary embodiment, the miR212 target is selected based on having sequence complementarity with all or a portion of SEQ ID NO:5 or SEQ ID NO:6. In one embodiment, the miR132 target has a region of 6-8 contiguous nucleotides that are complementary to the seed region of miR132. In another embodiment, the 6-8 contiguous nucleotides are located within the 3'UTR of the miR132 target. In another embodiment, the 6-8 contiguous nucleotides are located within an open reading frame of the miR132 target. In another embodiment of the foregoing aspects, the miR212 target has a region of 6-8 contiguous nucleotides that are complementary to the seed region of miR212. In one embodiment, the 6-8 contiguous nucleotides are located within the 3'UTR of the miR212 target. In another embodiment, the 6-8 contiguous nucleotides are located within an open reading frame of the miR212 target.

In some embodiments of the foregoing aspects, the foregoing methods further involve contacting the cell with an additional therapeutic agent, for example, an antiviral agent. In exemplary embodiments, the antiviral agent is Ganciclovir, Valganciclovir, Cidofovir, Foscarnet, Formivirsen, Acyclovir, Valacyclovir, CMX001, Artesunate, BAY-384766, T-611, GW-275175X, or Maribavir, or a combination thereof.

In another aspect, the invention provides a method of detecting an HCMV infection in a subject, by determining a level of miR132 or miR212 expression in a subject; and comparing the level of miR132 or miR212 expression to a suitable control; wherein an increase in the level of miR132 or miR212 expression relative to the suitable control indicates the presence of an HCMV infection in the subject.

In another aspect, the invention provides a kit comprising a composition comprising a miR132 antagonist, a miR212 antagonist, or combinations thereof; and instructions for administration of the composition to a subject for the treatment of HCMV. In some embodiments, the antagonist is selected from the group consisting of an antisense locked nucleic acid (LNA), an antagomir, and a 2'O-methyl antisense RNA.

In another aspect, the invention provides a kit comprising a composition comprising a miR132 target activating agent capable of increasing expression of a miR132 target, a miR212 target activating agent capable of increasing expression of a miR212 target, or combinations thereof; and (b) instructions for administration of the composition to a subject for the treatment of HCMV.

In exemplary embodiments of the foregoing aspects, the miR132 target activating agent is an expression vector encoding a miR132 target, a synthetic miR132 target RNA transcript, a miR132 target polypeptide, or a recombinant miR132 target polypeptide. In other exemplary embodiments of the foregoing aspects, the miR212 target activating agent is an expression vector encoding a miR212 target, a synthetic miR212 target RNA transcript, a miR212 target polypeptide, or a recombinant miR212 target polypeptide. In some embodiments, the miR132 target has a region of about 6-8 contiguous nucleotides that are complementary to the seed region of miR132. In other embodiments, the miR212 target has a region of about 6-8 contiguous nucleotides that are complementary to the seed region of miR212. In other embodiments, the target is MeCP2 or RICS. In some embodiments, the foregoing kits further contain an antiviral agent, for example, Ganciclovir, Valganciclovir, Cidofovir, Foscarnet, Formivirsen, Acyclovir, Valacyclovir, CMX001, Artesunate, BAY-384766, T-611, GW-275175X, or Maribavir, or combinations thereof.

I. Definitions

So that the invention may be more readily understood, certain terms are first defined.

The term "target gene," as used herein, refers to a gene or gene product intended for downregulation via RNA silencing. The term "target protein" refers to a protein intended for downregulation via RNA silencing of a target RNA encoding the target protein. The term "target RNA" refers to an RNA molecule intended for downregulation (e.g., repression or degradation) by RNA silencing. The term "target RNA" includes both non-coding RNA molecules (transcribed from a DNA but not encoding polypeptide sequence) and coding RNA molecules (i.e., mRNA molecules). A "target RNA" is also referred to herein as a "transcript".

The term "microRNA target, "miRNA target" or "miR target", as used herein, refers to a gene, gene transcript, or gene product whose expression is altered (e.g., downregulated) by a microRNA (miRNA or miR). A miRNA may alter the expression of a miRNA target by interacting with an RNA transcript, and preventing translation of a polypeptide encoded by the RNA transcript. A miRNA may alternatively alter the expression of a miRNA target by interacting with an RNA transcript, and directing degradation or destabilization of the RNA transcript. miRNA targets can be identified based on having a region of sequence complementarity to a portion of a miRNA. In a preferred embodiment, miRNA targets contain a region that is complementary to 6-8 nucleotides in a miRNA seed.

The term "miR145 target," as used herein, refers to a gene, gene transcript, or gene product (e.g., a polypeptide) whose expression is altered (e.g., downregulated) by miR145. miR145 may alter the expression of a miR145 target by interacting with an RNA transcript, and preventing translation of a polypeptide encoded by the RNA transcript. miR145 may alternatively alter the expression of a miR145 target by interacting with an RNA transcript, and directing degradation or destabilization of the RNA transcript. miR145 targets can be identified based on having a region of sequence complementarity to a portion of miR145. In a preferred embodiment, miR145 targets contain a region that is complementary to about 6-8 nucleotides in a miR145 seed. In exemplary embodiments, a miR145 target is a component of an HCMV replication pathway, e.g., a signaling pathway, that, when altered, modulates HCMV replication.

The term "miR132 target," as used herein, refers to a gene, gene transcript, or gene product (e.g., a polypeptide) whose expression is altered (e.g., downregulated) by miR132. miR132 may alter the expression of a miR132 target by interacting with an RNA transcript, and preventing translation of a polypeptide encoded by the RNA transcript. miR132 may alternatively alter the expression of a miR132 target by interacting with an RNA transcript, and directing degradation or destabilization of the RNA transcript. miR132 targets can be identified based on having a region of sequence complementarity to a portion of miR132. In a preferred embodiment, miR132 targets contain a region that is complementary to about 6-8 nucleotides in a miR132 seed. In exemplary embodiments, a miR132 target is a component of an HCMV replication pathway, e.g., a signaling pathway, that, when altered, modulates HCMV replication.

The term "miR212 target," as used herein, refers to a gene, gene transcript, or gene product (e.g., a polypeptide) whose expression is altered (e.g., downregulated) by miR212. miR212 may alter the expression of a miR212 target by interacting with an RNA transcript, and preventing translation of a polypeptide encoded by the RNA transcript. miR212 may alternatively alter the expression of a miR212 target by interacting with an RNA transcript, and directing degradation or destabilization of the RNA transcript. miR212 targets can be identified based on having a region of sequence complementarity to a portion of miR212. In a preferred embodiment, miR212 targets contain a region that is complementary to about 6-8 nucleotides in a miR212 seed. In exemplary embodiments, a miR212 target is a component of an HCMV replication pathway, e.g., a signaling pathway, that, when altered, modulates HCMV replication.

A miRNA seed, as used herein, refers to a region of about 6-8 contiguous nucleotides (e.g., 5-9, preferably 6-8 contiguous nucleotides) in a miRNA having perfect or near perfect complementarity with about 6-8 contiguous nucleotides in a target RNA. In a preferred embodiment, a miRNA seed encompasses about nucleotides 2-7 (e.g., nucleotides 3-8, nucleotides 1-6, preferably nucleotides 2-7) of a mature miRNA sequence. In exemplary embodiments, a miRNA seed has perfect complementarity with about 6-8 contiguous nucleotides in the 3'UTR of a target RNA.

The term "RNA silencing," as used herein, refers generally to a sequence-specific or selective process by which a target molecule (e.g., a target gene, protein or RNA) is downregulated. In some embodiments, the process of RNA silencing features post-transcriptional repression of RNA translation triggered by an RNA silencing agent (e.g., a miRNA). In other embodiments, the process of RNA silencing includes "RNA interference" or "RNAi," which features degradation of RNA molecules, e.g., RNA molecules within a cell, said degradation being triggered by an RNA silencing agent (e.g., a siRNA). Degradation is catalyzed by an enzymatic, RNA-induced silencing complex (RISC). RNAi occurs in cells naturally to remove foreign RNAs (e.g., viral RNAs). Natural RNAi proceeds via fragments cleaved from free dsRNA which direct the degradative mechanism to other similar RNA sequences. Alternatively, RNAi can be initiated by the hand of man, for example, to silence the expression of target genes.

The term "RNA silencing agent", as used herein, refers to an RNA (or analog thereof), having sufficient sequence complimentarity to a target RNA (i.e., the RNA being down regulated (e.g., repressed or degraded)) to direct RNA silencing. A RNA silencing agent having a "sequence sufficiently complementary to a target RNA sequence to direct RNA silencing" means that the RNA silencing agent has a sequence sufficient to repress translation of a polypeptide encoded by the target RNA, or that the RNA silencing agent has a sequence sufficient to trigger destruction of the target RNA by the RNAi machinery (e.g., the RISC complex). RNA silencing agents can include, for example, siRNA, shRNA, antisense RNA, miRNA, or other RNA-based or RNA-like silencing agents.

The term "RNAi agent", as used herein, refers to an RNA (or analog thereof), having sufficient sequence complimentarity to a target RNA (i.e., the RNA being degraded) to direct RNAi. A RNAi agent having a "sequence sufficiently complementary to a target RNA sequence to direct RNAi" means that the RNA agent has a sequence sufficient to trigger the destruction of the target RNA by the RNAi machinery (e.g., the RISC complex) or process. An RNAi agent can include, for example, an siRNA or an shRNA.

The term "miRNA agent," as used herein, refers to a miRNA, or an agent (e.g., an oligonucleotide agent) that mimics, replicates, or simulates the activity of an miRNA in RNA silencing (e.g., via translational repression, or sometimes, via RNA degradation, etc.) of one or more miRNA targets. Accordingly, a miRNA agent can include, for example, a miRNA, a miRNA mimic, a synthetic miRNA oligonucleotide, or an expression vector encoding a miRNA. A miRNA agent may also include a miRNA precursor that is capable of being cleaved by cellular machinery to form a miRNA, e.g., a pre-RNA a pri-RNA, or a miRNA stem-loop. Accordingly, a miRNA agent can include, for example, a pre-miRNA, a pri-miRNA, a miRNA stem-loop, an expression vector encoding a pre-miRNA, an expression vector encoding a pri-miRNA, or an expression vector encoding a miRNA stem-loop. An expression vector encoding a miRNA agent can include, for example, a plasmid expression vector or a viral expression vector. As with RNAi agents, miRNA agents act on target RNA via RISC.

The term "miR145 agent," as used herein, refers to miR145, or an agent (e.g., an oligonucleotide agent) that mimics, replicates, or simulates the activity of miR145 as a translational repressor of one or more miR145 targets. Accordingly, a miR145 agent can include, for example, miR145, a miR145 mimic, a synthetic miR145 oligonucleotide, or an expression vector encoding miR145. A miR145 agent may also include a miR145 precursor that is capable of being cleaved by cellular machinery to form a miR145, e.g., a miR145 pre-RNA, a miR145 pri-RNA, or a mir145 stem-loop. Accordingly, a miR145 agent can include, for example, a miR145 pre-miRNA, a miR145 pri-miRNA, a mir145 stem-loop, an expression vector encoding a miR145 pre-miRNA, an expression vector encoding a miR145 pri-miRNA, or an expression vector encoding a mir145 stem-loop. An expression vector encoding a miR145 agent can include, for example, a plasmid expression vector or a viral expression vector.

The term "miRNA antagonist," as used herein, refers to an agent that reduces or inhibits the expression, stability, or activity of a miRNA. A miRNA antagonist may function, for example, by blocking the activity of a miRNA (e.g., blocking the ability of a miRNA to function as a translational repressor of one or more miRNA targets), or by mediating miRNA degradation. Exemplary miRNA antagonists include, for example, antisense locked nucleic acid molecules (LNAs), antagomirs, or 2'O-methyl antisense RNAs targeting a miRNA.

For example, the term "miR132 antagonist," as used herein, refers to an agent that reduces or inhibits the expression, stability, or activity of miR132. A miR132 antagonist may function, for example, by blocking miR132 activity (e.g., blocking the ability of miR132 to function as a translational repressor of miR132 targets), or by mediating miR132 degradation. Exemplary miR132 antagonists include, for example, antisense locked nucleic acid molecules (LNAs), antagomirs, or 2'O-methyl antisense RNAs targeting miR132. Likewise, the term "miR212 antagonist," as used herein, refers to an agent that reduces or inhibits the expression, stability, or activity of miR212. A miR212 antagonist may function, for example, by blocking miR212 activity (e.g., blocking the ability of miR212 to function as a translational repressor of miR212 targets), or by mediating miR212 degradation. Exemplary miR212 antagonists include, for example, antisense locked nucleic acid molecules (LNAs), antagomirs, or 2'O-methyl antisense RNAs targeting miR212.

The term "miR132 target activating agent," as used herein, refers to a compound that increases, upregulates, enhances or mimics expression of a gene or gene product that is targeted by miR132. Such a compound may include, for example, an expression vector encoding a miR132 target, a synthetic RNA transcript encoding a miR132 target, a miR132 target polypeptide, a recombinant miR132 target polypeptide, or an active domain thereof.

The term "miR212 target activating agent," as used herein, refers to a compound that increases, upregulates, enhances or mimics expression of a gene or gene product that is targeted by miR212. Such a compound may include, for example, an expression vector encoding a miR212 target, a synthetic RNA transcript encoding a miR212 target, a miR212 target polypeptide, a recombinant miR212 target polypeptide, or an active domain thereof.

The term "RNA" or "RNA molecule" or "ribonucleic acid molecule" refers to a polymer of ribonucleotides. The term "DNA" or "DNA molecule" or deoxyribonucleic acid molecule" refers to a polymer of deoxyribonucleotides. DNA and RNA can be synthesized naturally (e.g., by DNA replication or transcription of DNA, respectively). RNA can be post-transcriptionally modified. DNA and RNA can also be chemically synthesized. DNA and RNA can be single-stranded (i.e., ssRNA and ssDNA, respectively) or multi-stranded (e.g., double-stranded, i.e., dsRNA and dsDNA, respectively).

The term RNA includes noncoding ("ncRNAs") and coding RNAs (i.e., mRNAs). ncRNAs are single- or double-stranded RNAs that do not specify the amino acid sequence of polypeptides (i.e., do not encode polypeptides). By contrast, ncRNAs affect processes including, but not limited to, transcription, gene silencing, replication, RNA processing, RNA modification, RNA stability, mRNA translation, protein stability, and/or protein translation. ncRNAs include, but are not limited to, bacterial small RNAs ("sRNA"), microRNAs ("miRNAs"), and/or small temporal RNAs ("stRNAs").

The term "mRNA" or "messenger RNA" refers to a single-stranded RNA that specifies the amino acid sequence of one or more polypeptide chains. This information is translated during protein synthesis when ribosomes bind to the mRNA.

The term "transcript" refers to a RNA molecule transcribed from a DNA or RNA template by a RNA polymerase template. The term "transcript" includes RNAs that encode polypeptides (i.e., mRNAs) as well as noncoding RNAs ("ncRNAs").

As used herein, expression of an RNA corresponding to a miRNA target (e.g., an mRNA, an miRNA, an ncRNA, etc.) is "upregulated" or "increased" when the amount of RNA, or of a polypeptide encoded by the RNA, present in a cell or biological sample is greater than the amount of RNA, or of a polypeptide encoded by the RNA, present in a control cell or biological sample. Likewise, expression of an RNA is "downregulated" or "decreased" when the amount of RNA, or of a polypeptide encoded by the RNA, present in a cell or biological sample is less than the amount of RNA, or of a polypeptide encoded by the RNA, present in a control cell or biological sample.

As used herein, expression of a polypeptide corresponding to a miRNA target is "upregulated" or "increased" when the amount of the polypeptide present in a cell or biological sample is greater than the amount of the polypeptide present in a control cell or biological sample. Likewise, expression of a polypeptide is "downregulated" or "decreased" when the amount of the polypeptide present in a cell or biological sample is less than the amount of the polypeptide present in a control cell or biological sample.

As used herein, the term "small interfering RNA" ("siRNA") (also referred to in the art as "short interfering RNAs") refers to an RNA agent, preferably a double-stranded agent, of about 10-50 nucleotides in length (the term "nucleotides" including nucleotide analogs), preferably between about 15-25 nucleotides in length, e.g., about 20-24 or 21-23 nucleotides in length, more preferably about 15, 16, 17, 18, 19, 20, 21, 22, 23, 24, or 25 nucleotides in length, the strands optionally having overhanging ends comprising, for example 1, 2 or 3 overhanging nucleotides (or nucleotide analogs), which is capable of directing or mediating RNA interference. Naturally-occurring siRNAs are generated from longer dsRNA molecules (e.g., >25 nucleotides in length) by a cell's RNAi machinery (e.g., Dicer or a homolog thereof).

As used herein, the term "miRNA" or "microRNA" refers to an RNA agent, preferably a single-stranded agent, of about 10-50 nucleotides in length (the term "nucleotides" including nucleotide analogs), preferably between about 15-25 nucleotides in length, e.g., about 20-24 or 21-23 nucleotides in length, more preferably about 15, 16, 17, 18, 19, 20, 21, 22, 23, 24, or 25 nucleotides in length, which is capable of directing or mediating RNA silencing. Naturally-occurring miRNAs are generated from stem-loop precursor RNAs (i.e., pre-miRNAs) by Dicer. The term "Dicer" as used herein, includes Dicer as well as any Dicer orthologue or homologue capable of processing dsRNA structures into siRNAs, miRNAs, siRNA-like or miRNA-like molecules. The term microRNA (or "miRNA") is used interchangeably with the term "small temporal RNA" (or "stRNA") based on the fact that naturally-occurring microRNAs (or "miRNAs") have been found to be expressed in a temporal fashion (e.g., during development).

The term "pri-miRNA," as used herein, refers to an RNA molecule that is capable of being processed by a ribonuclease (e.g., Drosha) into an about 60-150 nucleotide hairpin RNAs. A pri-miRNA may be about 100-2000 nucleotides long, more preferably, about 200-1500 nucleotides, more preferably about 300-1000 nucleotides. The term "pre-miRNA," as used herein, refers to an about 60-150 nucleotide hairpin RNA molecule that is capable of being processed by a ribonuclease (e.g., Dicer) into an about 10-50 nucleotide miRNA.

The term "shRNA", as used herein, refers to an RNA agent having a stem-loop structure, comprising a first and second region of complementary sequence, the degree of complementarity and orientation of the regions being sufficient such that base pairing occurs between the regions, the first and second regions being joined by a loop region, the loop resulting from a lack of base pairing between nucleotides (or nucleotide analogs) within the loop region. shRNAs may be substrates for the enzyme Dicer, and the products of Dicer cleavage may participate in RNAi. shRNAs may be derived from transcription of an endogenous gene encoding a shRNA, or may be derived from transcription of an exogenous gene introduced into a cell or organism on a vector, e.g., a plasmid vector or a viral vector. An exogenous gene encoding an shRNA can additionally be introduced into a cell or organism using other methods known in the art, e.g., lipofection, nucleofection, etc.

The term "nucleoside" refers to a molecule having a purine or pyrimidine base covalently linked to a ribose or deoxyribose sugar. Exemplary nucleosides include adenosine, guanosine, cytidine, uridine and thymidine. The term "nucleotide" refers to a nucleoside having one or more phosphate groups joined in ester linkages to the sugar moiety. Exemplary nucleotides include nucleoside monophosphates, diphosphates and triphosphates. The terms "polynucleotide" and "nucleic acid molecule" are used interchangeably herein and refer to a polymer of nucleotides joined together by a phosphodiester linkage between 5' and 3' carbon atoms.

The term "nucleotide analog" or "altered nucleotide" or "modified nucleotide" refers to a non-standard nucleotide, including non-naturally occurring ribonucleotides or deoxyribonucleotides. Preferred nucleotide analogs are modified at any position so as to alter certain chemical properties of the nucleotide yet retain the ability of the nucleotide analog to perform its intended function. Examples of positions of the nucleotide which may be derivitized include the 5 position, e.g., 5-(2-amino)propyl uridine, 5-bromo uridine, 5-propyne uridine, 5-propenyl uridine, etc.; the 6 position, e.g., 6-(2-amino)propyl uridine; the 8-position for adenosine and/or guanosines, e.g., 8-bromo guanosine, 8-chloro guanosine, 8-fluoroguanosine, etc. Nucleotide analogs also include deaza nucleotides, e.g., 7-deaza-adenosine; O- and N-modified (e.g., alkylated, e.g., N6-methyl adenosine, or as otherwise known in the art) nucleotides; and other heterocyclically modified nucleotide analogs such as those described in Herdewijn, *Antisense Nucleic Acid Drug Dev.,* 2000 Aug. 10(4):297-310.

Nucleotide analogs may also comprise modifications to the sugar portion of the nucleotides. For example the 2' OH-group may be replaced by a group selected from H, OR, R, F, Cl, Br, I, SH, SR, $NH_2$, NHR, $NR_2$, COOR, or OR, wherein R is substituted or unsubstituted $C_1$-$C_6$ alkyl, alkenyl, alkynyl, aryl, etc. Other possible modifications include those described in U.S. Pat. Nos. 5,858,988, and 6,291,438.

The phosphate group of the nucleotide may also be modified, e.g., by substituting one or more of the oxygens of the phosphate group with sulfur (e.g., phosphorothioates), or by making other substitutions which allow the nucleotide to perform its intended function such as described in, for example, Eckstein, *Antisense Nucleic Acid Drug Dev.* 2000 Apr. 10(2):117-21, Rusckowski et al. *Antisense Nucleic Acid Drug Dev.* 2000 Oct. 10(5):333-45, Stein, *Antisense Nucleic Acid Drug Dev.* 2001 Oct. 11(5): 317-25, Vorobjev et al. *Antisense Nucleic Acid Drug Dev.* 2001 Apr. 11(2):77-85, and U.S. Pat. No. 5,684,143. Certain of the above-referenced modifications (e.g., phosphate group modifications) preferably decrease the rate of hydrolysis of, for example, polynucleotides comprising said analogs in vivo or in vitro.

The term "oligonucleotide" refers to a short polymer of nucleotides and/or nucleotide analogs. The term "RNA analog" refers to an polynucleotide (e.g., a chemically synthesized polynucleotide) having at least one altered or modified nucleotide as compared to a corresponding unaltered or unmodified RNA but retaining the same or similar nature or function as the corresponding unaltered or unmodified RNA. As discussed above, the oligonucleotides may be linked with linkages which result in a lower rate of hydrolysis of the RNA analog as compared to an RNA molecule with phosphodiester linkages. For example, the nucleotides of the analog may comprise methylenediol, ethylene diol, oxymethylthio, oxyethylthio, oxycarbonyloxy, phosphorodiamidate, phophoroamidate, and/or phosphorothioate linkages. Preferred RNA analogues include sugar- and/or backbone-modified ribonucleotides and/or deoxyribonucleotides. Such alterations or modifications can further include addition of non-nucleotide material, such as to the end(s) of the RNA or internally (at one or more nucleotides of the RNA). An RNA analog need only be sufficiently similar to natural RNA that it has the ability to mediate (mediates) RNA interference.

As used herein, the term "nuclease-resistant oligonucleotide" refers to any oligonucleotide that has been modified to inhibit degradation by enzymes such as, for example, the exonucleases known to be present in the cytoplasm of a eukaryotic cell. RNA molecules (e.g., RNA oligonucleotides) are particularly at risk of degradation when combined with a composition comprising a cell extract or when introduced to a cell or organism, and a "ribonuclease-resistant" oligonucleotide is thus defined as an antisense molecule/agent that is relatively resistant to ribonuclease enzymes (e.g., exonucleases), as compared to an unmodified form of the same oligonucleotide. Preferred antisense molecules/agents of the invention include those that have been modified to render the oligonucleotide relatively nuclease-resistant or ribonuclease-resistant. In a preferred embodiment, the antisense agents and/or oligonucleotides of the invention have been modified with a 2'-O-methyl group (e.g., 2'-O-methylcytidine, 2'-O-methylpseudouridine, 2'-O-methylguanosine, 2'-O-methyluridine, 2'-O-methyladenosine, 2'-O-methyl) and additionally comprise a phosphorothioate backbone.

The terms "2'-O-methyl modification" and "phosphorothioate modification" as used herein, possess their art-recognized meanings.

The term "locked nucleic acid (LNA)," as used herein, refers to a nucleic acid analogue containing one or more LNA nucleotide monomers with a bicyclic furanose unit locked in an RNA mimicking sugar conformation. The ribose moiety of an LNA nucleotide is modified with an extra bridge (e.g., a 2'-O,4'-C methylene bridge) connecting the 2' and 4' carbons. The bridge 'locks' the ribose in the 3'endo structural conformation, which is often found in the A-form of RNA. LNA oligonucleotides display unprecedented hybridization affinity toward complementary single-stranded RNA, including miRNA. Structural studies have shown that LNAs are effective RNA mimics that induce an A-type (RNA-like) duplex geometry. The locked ribose conformation of LNAs enhances base stacking and significantly increases the thermal stability of oligonucleotides containing LNAs. Additional properties of LNAs have been described in U.S. Patent Publication No. 20050227256A1 (U.S. Ser. No. 10/998,364), the entire contents of which are incorporated herein by reference. LNAs have been shown to be highly effective in silencing miRNAs.

The term "antagomir," as used herein, refers to small synthetic RNA-like oligonucleotides that are complementary to a specific miRNA target (i.e., miR132), and that harbor various modifications for RNAse protection. Antagomirs have beneficial pharmacologic properties such as enhanced tissue and cellular uptake. Antagomirs differ from normal RNA by complete 2'-O-methylation of sugar, phosphorothioate backbone and a cholesterol-moiety at 3'-end. In some embodiments, antagomirs can have either mispairing at the cleavage site of Ago2, or a base modification at this site to inhibit Ago2 cleavage. Antagomirs are believed to silence miRNA by irreversibly binding to miRNA molecules, rendering them nonfunctional.

The terms "morpholinos" or "morpholino oligos," as used herein, refers to nucleic acid analogs having standard nucleic acid bases that are bound to morpholine rings, rather than to deoxyribose rings, and are linked through phosphorodiamidate groups, rather than phosphates. Based on the similarity to natural nucleic acid structure, morpholinos bind to complementary sequences of mRNA by standard Watson-Crick base pairing. Instead of degrading their target RNA molecules, morpholinos act by steric blocking, binding to a target sequence within an RNA (e.g., a miRNA, i.e., miR132) and inhibiting interaction of molecules which might otherwise interact with the RNA.

The term "antisense" refers generally to any approach reliant upon agents, e.g., oligonucleotides, that are sufficiently complementary to a target sequence to associate with the target sequence in a sequence-specific manner (e.g., hybridize to the target sequence). Exemplary uses of antisense in the instant application involve use of an oligoribonucleotide agent that hybridizes to a target RNA and blocks an activity/effect of the targeted RNA sequence, but antisense approaches commonly are used to target DNA or RNA for transcriptional inhibition, translational inhibition, degradation, etc. Antisense is a technology that can be initiated by the hand of man, for example, to modulate splicing and/or silence the expression of target genes.

As used herein, the term "isolated RNA" (e.g., "isolated mRNA", "isolated miRNA" or "isolated RNAi agent") refers to RNA molecules which are substantially free of other cellular material, or culture medium when produced by recombinant techniques, or substantially free of chemical precursors or other chemicals when chemically synthesized.

The term "in vitro" has its art recognized meaning, e.g., involving purified reagents or extracts, e.g., cell extracts. The term "in vivo" also has its art recognized meaning, e.g., involving living cells, e.g., immortalized cells, primary cells, cell lines, and/or cells in an organism.

As used herein, the term "druggable target" refers to a target (i.e, gene or gene product) having certain desired properties which indicate a potential for drug discovery, i.e., for use in the identification, research and/or development of therapeutically relevant compounds. A druggable target is distinguished based on certain physical and/or functional properties selected by a person skilled in the art of drug discovery. A druggable target (i.e., gene or gene product) of the instant invention, for example, is distinguished from other genes and/or gene products based on the fact that that it is regulated by miR145, miR132, and/or miR212.

Based on the fact that these targets are regulated by HCMV infection, it is believed that the targets are important in essential cellular processes, for example, maintenance of cellular homeostasis, host cell defense mechanisms, and the like, or in essential viral processes, for example, processes involved in viral replication. Control of such processes, including situations in which such processes are misregulated (i.e., in the biology of a disease), has obvious therapeutic appeal. Additional criteria for identifying and/or selecting druggable targets include, but are not limited to (1) cellular localization susceptible to systemically administered (e.g., orally administered) drugs; (2) homology or similarity to other genes and/or gene products (e.g., members of a gene family) previously successfully targeted; and (3) data (e.g., expression and/or activity data) indicating a role for the gene/gene product at a critical intervention points in a disease pathway.

The term "antiviral drug target", as used herein, refers to a target (i.e, gene or gene product) having certain desired properties which indicate a potential for antivral drug discovery, i.e., for use in the identification, research and/or development of compounds useful in antiviral therapies. A druggable target (i.e., gene or gene product) of the instant invention, for example, is indicated as an antiviral drug target based on the fact that miR145, miR132, miR212, and targets thereof, are regulated by HCMV expression.

A gene "involved" in a disorder includes a gene, the normal or aberrant expression or function of which effects or causes or contributes to a disease or disorder or at least one symptom of said disease or disorder.

The phrase "examining the function of a gene in a cell or organism" refers to examining or studying the expression, activity, function or phenotype arising therefrom.

Various methodologies of the instant invention include step that involves comparing a value, level, feature, characteristic, property, etc. to a "suitable control", referred to interchangeably herein as an "appropriate control". A "suitable control" or "appropriate control" is any control or standard familiar to one of ordinary skill in the art useful for comparison purposes. In one embodiment, a "suitable control" or "appropriate control" is a value, level, feature, characteristic, property, etc. determined prior to performing a given methodology, as described herein. For example, a transcription rate, mRNA level, translation rate, protein level, biological activity, cellular characteristic or property, genotype, phenotype, etc. can be determined prior to introducing a compound (e.g., a compound that increases or mimics expression of miR145; a compound that inhibits or reduces expression of a gene or gene product that is targeted by miR145; a compound that antagonizes miR132 and/or miR212; a compound that increases, upregulates, enhances or mimics expression of a gene or gene product that is targeted by miR132 and/or miR212, etc.) of the invention into a cell or organism. In certain embodiments, a suitable control is a value, level, feature, characteristic, property, etc. determined in a cell or organism, e.g., a cell or organism infected with HCMV, in the absence of a miR145 agent or an RNA silencing agent. In other embodiments, a suitable control is a value, level, feature, characteristic, property, etc. determined in a cell or organism, e.g., a cell or organism infected with HCMV, in the absence of a miR132 antagonist, a miR212 antagonist, a miR132 target activating agent, or a miR212 target activating agent. In methodologies that involve infecting a cell or organism with a virus, e.g., HCMV, the properties of a "suitable control" or an "appropriate control" can also be determined in cells or organisms that are uninfected or mock infected. In another embodiment, a "suitable control" or "appropriate control" is a value, level, feature, characteristic, property, etc. determined in a cell or organism, e.g., a control or normal cell or organism, exhibiting, for example, normal traits. In yet another embodiment, a "suitable control" or "appropriate control" is a predefined value, level, feature, characteristic, property, etc.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Various aspects of the invention are described in further detail in the following subsections.

II. miRNAs and RNA Interference

MicroRNAs (miRNAs) are small (e.g., 10-50 nucleotides), single-stranded noncoding RNA molecules that regulate gene expression in eukaryotes at the level of translation. MicroRNAs are initially transcribed as a long, single-stranded miRNA precursor known as a pri-miRNA, which may contain one or several miRNAs. These pri-miRNAs typically contain regions of localized stem-loop hairpin structures that contain the mature miRNA sequences. Pri-miRNAs are processed into 60-150 nucleotide pre-miRNAs in the nucleus by the double-stranded RNA-specific nuclease Drosha. These pre-miRNAs typically adopt a hairpin conformation with at least one stem-loop structure. The 60-150 nucleotide pre-miRNAs are transported to the cytoplasm, where they are processed by the enzyme Dicer into single-stranded mature miRNAs of about 10-50 nucleotides (more preferably, 15-25 nucleotides). This is in contrast with siRNAs, which are of a similar size but are double-stranded, and are usually processed from a double-stranded RNA precursor.

Following processing, mature miRNAs are incorporated into an effector complex termed miRISC (miRNA-Induced Silencing Complex), which participates in RNA silencing. miRNAs can pair with target mRNAs that contain sequences only partially complementary (e.g., 30%, 35%, 40%, 50%, 55%, 60%, 65%, 70%, 75%, 80%, 90% or more) to the miRNA. Such pairing typically occurs in the 3'untranslated regions (3'UTR) of mRNA, and results in repression of mRNA translation without altering mRNA stability. Alternatively, miRNAs with a substantial degree of complementarity to their targets can effect gene silencing by mediating mRNA degradation, e.g., via RNAi (Hutvagner and Zamore (2002) *Science* 297:2056-2060). As expression of precursor microRNAs (i.e., pri-miRNAs) is often developmentally regulated, miRNAs are often referred to interchangeably in the art as "small temporal RNAs" or "stRNAs".

*C. elegans* contains approximately 100 endogenous miRNA genes, about 30% of which are conserved in vertebrates. Mammalian genomes are predicted to encode at least 200 to 1000 distinct miRNAs, many of which are estimated to interact with 5-10 different mRNA transcripts. Accordingly, miRNAs are predicted to regulate up to one-third of all genes. miRNAs are differentially expressed in various tissues, such that each tissue is characterized by a specific set of miRNAs. miRNAs have been shown to be important modulators of cellular pathways including growth and proliferation, apoptosis, and developmental timing. Given the pathways over which miRNAs exert a regulatory effect, it is not surprising that alterations in miRNA expression have been detected in several types of cancer, including breast and lung carcinomas. These recognized pathways likely represent the tip of an iceberg, however, as the abundance of miRNAs within eukaryotic cells indicates that many downstream effects of miRNA-induced silencing remain to be identified.

III. Viral Modulation of Cellular miRNA Expression

Viruses possess small genomes made up of nucleic acid. Examples of viruses possessing genomes made up of DNA are known in the art and include, but are not limited to, poxvirus, herpes virus, adenovirus, papillomavirus, and parvovirus. Examples of viruses possessing genomes made up of RNA are likewise known in the art and include, but are not limited to, influenza virus, rotavirus, mumps virus, rabies virus, HIV/AIDS virus, corona virus, LCM virus and poliovirus. The viral genome can be either single- or double-stranded, and is packaged in a capsid, or protein coat, which in enveloped viruses is further enclosed by a lipid envelope. Nonenveloped viruses leave an infected cell by lysing and thereby killing the cell. Enveloped viruses can leave the cell by budding, without disrupting the plasma membrane and, therefore, without killing the cell. Enveloped viruses can thus cause chronic infections, in some cases helping transform an infected cell into a cancer cell.

All viruses use the basic host cell machinery for most aspects of their reproduction, including transcription and translation. Many viruses encode proteins that modify the host transcription or translation apparatus to modulate expression of host cell genes to create an environment that favors the synthesis of viral proteins over those of the host cell. Some viruses, including HCMV, additionally encode miRNAs. These miRNAs may likewise modify expression of host cell factors to create an environment favorable for viral replication.

If cellular miRNAs are involved in inhibition of viral replication, it is possible that viruses counter this process by interfering with cellular miRNA expression. Indeed, PFV-1 has been shown to encode the protein Tas, which broadly suppresses miRNA activity. Remarkably, instances of positive regulation of cellular miRNA expression by viruses have also been reported. Human miRNA miR-122 interacts with the 5'-non-coding region of HCV and increases viral RNA production, through a mechanism which remains to be elucidated (Jopling (2005) *Science* 309:1577-1581). In addition, latency type III Epstein-Barr Virus (EBV) infections have been associated with induction of miR-155 in human B cells (Nair (2006) *TRENDS in Microbiology* 14:169-175), indicating that this miRNA is beneficial for EBV replication.

IV. HCMV Specifically Modulates Expression of miR145

The present invention is based, at least in part, on the discovery that miR145 is significantly downregulated following infection with HCMV, indicating that miR145 is an important cellular mediator of HCMV infection. HCMV is a herpesvirus that has developed mechanisms to modify the cellular environment. One of its strategies is to alter the cellular miRNA expression pattern. Microarray analysis indicated that 48 hours after HCMV infection of Human Embryonic Lung (HEL) fibroblasts, cellular miRNA expression pattern changed significantly with no unidirectional trend, suggesting that HCMV specifically utilizes this pathway, rather than inhibits it. Without wishing to be bound by theory, HCMV may be reprogramming cells through miRNA expression. The discovery that HCMV modulates expression of cellular miRNAs including miR145 indicates that HCMV alters cellular miRNA expression to enhance its replication.

The data set forth herein demonstrate that miRNA 145 expression is significantly downregulated during HCMV infection. miR145 regulates expression of Insulin Receptor Substrate-1 (IRS-1). In particular, miR145 binds to the 3'UTR of IRS-1, causing translational repression. IRS-1 plays a fundamental role in the Insulin Receptor signaling pathway. Upon activation by phosphorylation, IRS-1 functions as a scaffolding protein that mediates downstream signaling events, which lead to upregulation of cellular metabolic activity, such as mitogen activated protein kinase (MAPK) and phosphatidyl inositol 3-phosphate kinase (PI3K) pathways. miR145 downregulation was confirmed by Northern blot and quantitative Real Time PCR (qRT-PCR). In addition, a differential localization of IRS-1 protein was observed in infected cells by immunofluorescence, indicating that HCMV induces relocalization of this protein. To counteract the effect of HCMV-induced miR145 downregulation, a miR145 mimic was transfected into fibroblast cells, which were subsequently infected with HCMV. Decreased levels of the viral proteins at Immediate Early (IE), Early (E), and Late (L) stages of HCMV replication (e.g., IE2, pp65, and gB55), in addition to >1 log reduction in viral titers, were observed in cells transfected with the miR145 mimic, indicating that the specific reduction of cellular miR145 by HCMV enhances viral replication. Reduction of cellular miR145 can also alter signaling pathways downstream of IRS-1, such as MAPK and PI3K. Modulation of these downstream signaling pathways may further promote HCMV replication.

The foregoing discoveries pertaining to the downregulation of cellular miR145 following HCMV infection can provide relevant information about the cellular mechanisms modified by this virus that may enhance its replication and pathogenicity. These discoveries indicate that miR145 agents (i.e., miR145 or an agent, e.g., an oligonucleotide agent mimicking the activity of miR145 as a translational repressor of one or more miR145 targets) may be used to inhibit HCMV, or to treat an infection caused by HCMV. In addition, these discoveries reveal that miR145 targets, and signaling pathways involving miR145 targets, are attractive druggable targets for therapeutic intervention for the treatment of HCMV infections. Particular targets include, for example, genes or gene products whose expression is regulated by miR145, and signaling pathways involving genes or gene products regulated by miR145. Such targets include, for example, IRS-1 and IRS-1 signaling pathways, including MAPK and PI3K. Moreover, since miR145 is downregulated in certain cancers and malignancies (Akao et al., 2007), downstream targets of miR145 that are useful for treatment of HCMV infections may also be useful therapeutic targets in other diseases mediated by aberrant miR145 regulation, e.g., cancer.

V. HCMV Specifically Modulates Expression of miR132 and miR212

The present invention is also based, at least in part, on the discovery that miR132 and miR212 are significantly upregulated following infection with HCMV, indicating that miR132 is an important cellular mediator of HCMV infection. As noted above, the data set forth herein indicates that HCMV may be reprogramming cells through miRNA expression. The discovery that HCMV modulates expression of cellular miRNAs including miR132 and miR212 indicates that HCMV alters cellular miRNA expression to enhance its replication.

The data set forth herein demonstrate that miRNA 132 and miR212 expression is significantly upregulated during HCMV infection. miR132 regulates expression of methyl CpG-binding protein 2 (MeCP2). miR212 is encoded by a gene located adjacent to miR212, and both miR132 and miR212 share a common seed sequence. miR212 also regulates expression of MeCP2. Methylation of CpG residues is associated with gene silencing. MeCP2 binds to methyl-CpGs, where it functions as a transcriptional repressor. MeCP2 plays a major role in brain development, and mutations in MeCP2 are largely responsible for the development of mental retardation in a severe form of autism known as Retts Syndrome. In addition, mis-expression of Brain Derived Neurotrophic Factor (BDNF) by MeCP2 in neuron cultures affects dendritic and axonal arborization. The data set forth herein indicates that MeCP2 expression is downregulated in fibroblasts during HCMV infection, consistent with the observed increase in miR132 and/or miR212 expression. Moreover, transfection with an antisense miR132 LNA oligonucleotide, an antisense miR212 LNA oligonucleotide, and combinations thereof, increased intracellular levels of MeCP2, indicating that miR132 and miR212 are targeting MeCP2. Another target of miR132 and miR212 is Rho GTPase-activating protein (RICS; also known in the art as p250GAP). Like MeCP2, RICS is also involved in neuronal development and maturation. RICS is expressed at high levels in the Central Nervous System (CNS), where it regulates neurite outgrowth. Increases in miR132 resulting in altered levels of RICS have been shown to lead to exaggerated arborization of cultured neurons. Accordingly, alterations in RICS and MEcP2 expression resulting from upregulation of miR132 during HCMV infection likely contribute to the pathology of HCMV disorders. The data set forth herein demonstrate that inhibition of miR132 function by transfection of cells with an antisense miR132 LNA oligonucleotide and/or a miR212 LNA oligonucleotide attenuates viral replication, evidenced by reduction in virus release, and reduction in expression of viral proteins IE2, pp65, and gB55. This finding implicates HCMV-induced upregulation of miR132 and miR212 in viral replication.

Taken together, it is likely that upregulation of miR132 and/or miR212 is one mechanism by which HCMV infection contributes to HCMV pathogenesis. For example, upregulation of miR132 and/or miR212 is one mechanism by which HCMV infection may cause neurological disorders, including birth defects. HCMV is currently the leading cause of birth defects associated with an infectious agent. Anomalies include CNS malformations, mental retardation, inflammatory diseases, and organ dysfunction. In addition, HCMV is the leading cause of nonfamilial hearing loss in children. The findings set forth herein demonstrate that treatment modalities based on inhibiting miR132 and/or miR212 upregulation, and the corresponding downregulation of miR132 and miR212 targets, in HCMV infected cells can be effective to inhibit HCMV replication and HCMV infection. Accordingly, such treatment modalities can be used to treat or ameliorate the symptoms of HCMV-mediated disorders.

The foregoing discoveries pertaining to the upregulation of cellular miR132 and miR212 following HCMV infection can provide relevant information about the cellular mechanisms modified by this virus that may enhance its replication and pathogenicity. These discoveries indicate that miR132 or miR212 antagonists (i.e., an agent that reduces or inhibits the expression, stability, or activity or miR132 and/or miR212) may be used to inhibit HCMV, or to treat an infection caused by HCMV. In addition, these discoveries reveal that miR132 and/or miR212 targets, and signaling pathways involving these targets, are attractive druggable targets for therapeutic intervention for the treatment of HCMV infections. Particular targets include, for example, genes or gene products whose expression is regulated by miR132 and/or miR212, and signaling pathways involving genes or gene products regulated by miR132 and/or miR212. Such targets include, for example, MeCP2 and MeCP2 signaling pathways, and RICS and RICS signaling pathways.

VI. Therapeutic Applications

As described herein, miR145 and miR145 target molecules (e.g., IRS-1) have therapeutic and diagnostic utility. miR145 and miR145 target molecules (e.g., IRS-1) can further be used experimentally, for example, in identifying antiviral agents that are effective in the treatment of HCMV infection. Likewise, miR132 and miR212, and target molecules thereof (e.g., MeCP2 and RICS) have therapeutic and diagnostic utility. miR132, miR212, and target molecules thereof (e.g., MeCP2 and RICS) can further be used experimentally, for example, in identifying antiviral agents that are effective in the treatment of HCMV infection.

A. Inhibition of HCMV Replication and Treatment of HCMV Infection Using miR145 Agents In one aspect, the invention provides methods of inhibiting HCMV replication in a cell, comprising contacting the cell with a miR145 agent in an amount effective to decrease the level of one or more miR145 targets, or a gene product (e.g., a polypeptide) encoded by one or more miR145 targets, such that HCMV replication is inhibited. A miR145 agent, as used herein, is miR145, or an agent (e.g., an oligonucleotide agent) mimicking, replicating or simulating the activity of miR145 as a translational repressor of one or more miR145 targets. Accordingly, a miR145 agent includes, for example, miR145, a miR145 mimic, a synthetic miR145 oligonucleotide, or an expression vector encoding miR145. In an exemplary embodiment, a miR145 agent comprises a nucleic acid molecule comprising the nucleic acid sequence of the stem-loop form of miR145, as set forth in SEQ ID NO:1: 5'CACCUUGUCCUCACGGUCCAGUUUUCCCAGGAAUCCCUUAGAUGCUAA GAUGGGGAUUCCUGGAAAUACUGUUCUUGAGGUCAUGGUU 3' (miRNA ID No: hsa-mir-145; Accession No: MI0000461). In other exemplary embodiments, a miR145 agent comprises a nucleic acid molecule comprising the nucleic acid sequence of the mature, processed form of miR145, as set forth in SEQ ID NO:2: 5'GUCCAGUUUUCCCAGGAAUCCCU 3'. Contacting a cell with a miR145 agent compensates for the decrease in miR145 that occurs during HCMV infection, thereby negating any beneficial effect derived by HCMV as a consequence of miR145 downregulation. The foregoing methods may additionally comprise measuring the level of HCMV replication in a cell after contacting the cell with a miR145 agent, and comparing the level of HCMV replication to a suitable control. In this embodiment, a preferred miR145 agent, or a preferred quantity of a miR145 agent, is one which decreases the level of HCMV replication when compared to a suitable control, e.g., a comparable cell not contacted with a miR145 agent.

In some embodiments, a miR145 agent can be a single stranded nucleic acid molecule containing the nucleic acid sequence of mature miR145 (SEQ ID NO:2). In other embodiments, a miRNA agent can be a double stranded nucleic acid molecule, wherein one strand contains the nucleic acid sequence of mature miR145, and the other strand is entirely or partially complementary to the nucleic acid sequence of mature miR145. In other embodiments, a miR145 agent can be a single or double stranded nucleic acid molecule containing a nucleic acid sequence having 50% or more identity with the nucleic acid sequence of mature miR145 (SEQ ID NO:2), wherein the miRNA agent has an activity of miR145 (e.g., functions in RNA silencing of one or more miR145 targets). In preferred embodiments, a miR145 agent is a single or double stranded nucleic acid molecule containing a nucleic acid sequence having at least 60%, 70%, 80%, 90%, 95%, 99% or more identity with the nucleic acid sequence of mature miR145 (SEQ ID NO:2). In some embodiments, a miR145 agent is a single or double stranded nucleic acid molecule containing a nucleic acid sequence having 1 or more (e.g., 1 2, 3, 4, 5, 6, 7, 8, 9, 10 or more) nucleic acid substitutions with respect to the nucleic acid sequence of mature miR145 (SEQ ID NO:2), wherein the miRNA agent has an activity of miR145 (e.g., functions in RNA silencing of one or more miR145 targets).

In some embodiments, the foregoing miR145 agents contain one or more modifications to improve stability of the miR145 agents. Such modifications include, for example, the incorporation of nuclease-resistant oligonucleotides, as described herein. Exemplary modifications that improve the stability of miR145 agents include modifications to the 2' position of the nucleotide sugar, such as 2'-O-Me, 2'-F, 2'-deoxy, 2'-MOE, and LNA. In some embodiments, a miR145 agent may be conjugated to a lipophillic moiety, e.g., cholesterol, or formulated in liposomes to enhance delivery of the agent to cells, tissues, or organisms.

In other embodiments, the foregoing miR145 agents can be incorporated within a small hairpin RNA. Such a hairpin RNA can have an identical or similar sequence to a miR145 pre-miRNA (e.g. SEQ ID NO:1). In some embodiments, a miR145 agent can contain a nucleic acid sequence having 50% or more identity with the nucleic acid sequence of a miR145 pre-miRNA (SEQ ID NO:1), wherein the miRNA agent has an activity of miR145 (e.g., functions in RNA silencing of one or more miR145 targets following processing by a ribonuclease, e.g., Dicer). In preferred embodiments, a miR145 agent contains a nucleic acid sequence having 60%, 70%, 80%, 90%, 95%, 99% or more identity with the nucleic acid sequence of a miR145 pre-miRNA (SEQ ID NO:1). In some embodiments, a miRNA agent contains a nucleic acid sequence having 1 or more (e.g., 1 2, 3, 4, 5, 6, 7, 8, 9, 10, 15, or 20) nucleic acid substitutions with respect to the nucleic acid sequence of a miR145 pre-miRNA (SEQ ID NO:1), wherein the miRNA agent has an activity of miR145 (e.g., functions in RNA silencing of one or more miR145 targets following processing by a ribonuclease, e.g., Dicer).

In some embodiments, the foregoing miR145 agents can be expressed from an expression vector, e.g., a DNA vector or a viral vector. In preferred embodiments, the foregoing miR145 agents are expressed from a polymerase II or polymerase III promoter. In exemplary embodiments, an expression vector used to express a miR145 agent is a plasmid vector, an adenovirus vector, a lentivirus vector, or a YAC vector.

A cell that is contacted by a miR145 agent in accordance with the methods of the invention may be found within an organism. In this embodiment, administering a miR145 agent to an organism can inhibit HCMV proliferation, for example, in a cell within the organism that is contacted by the miR145 agent. In preferred embodiments, the organism is infected with HCMV. In these embodiments, administering a miR145 agent to the organism is used to treat HCMV infection. In other embodiments, the organism is at risk of contracting or developing an HCMV infection. In these embodiments, administering a miR145 agent to the organism is used to prevent HCMV infection. miR145 agents may be used, for example, for the treatment or prevention of HCMV-mediated diseases or disorders, e.g., HCMV retinitis, HCMV hepatitis, HCMV-mediated pneumonia, HCMV-mediated birth defects, cytomegalovirus infection associated with transplantation, e.g., transplantation of kidney, lung, liver, pancreas, and heart, polyradiculopathy, encephalitis, gastrointestinal tract disease, myocarditis or pancreatitis. miR145 agents can also be used prophylactically, e.g., for the prophylaxis of cytomegalovirus disease associated with transplantation of kidney, lung, liver, pancreas, and heart, or for the prevention of HCMV-mediated congenital disorders.

B. Inhibition of HCMV Replication and Treatment of HCMV Infection Using RNA Silencing Agents Capable of Mediating Expression of a miR145 Target, or a Component of a Signaling Pathway Involving a miR145 Target In another aspect, the invention provides methods of inhibiting HCMV replication in a cell, comprising contacting the cell with an RNA silencing agent capable of mediating RNAi of a miR145 target in an amount effective to decrease the level of a miR145 target, such that HCMV replication is inhibited. Contacting a cell with an RNA silencing agent that degrades, decreases, or downregulates expression of a miR145 target compensates for the increase in expression of miR145 targets that occurs as a result of miR145 downregulation during HCMV infection. In this way, any beneficial effect derived by HCMV as a consequence of increasing expression of miR145 targets by downregulating miR145 is negated.

An RNA silencing agent, as used herein, refers to an RNA (or analog thereof), having sufficient sequence complimentarity to a target RNA to direct translational repression of the target RNA, or to direct degradation of the target RNA, e.g., through RNAi. A RNA silencing agent having a sequence sufficiently complementary to a target RNA sequence to direct RNAi means that the RNA silencing agent has a sequence sufficient to interact with the target RNA, causing translational repression, or to trigger the destruction of the target RNA by the RNAi machinery (e.g., the RISC complex) or process. Exemplary RNA silencing agents include, for example, siRNA, shRNA, antisense RNA, miRNA, pre-miRNA, pri-miRNA, and ribozymes. Methods for designing RNA silencing agents (e.g., siRNA, shRNA, antisense RNA, miRNA, pre-miRNA, pri-miRNA, or ribozymes) that specifically decrease or downregulate expression of a target gene are well known in the art. In some embodiments, the RNA silencing agent can be expressed in a cell from an expression vector.

In preferred embodiments, the target gene is a miR145 target. In other embodiments, HCMV replication can be inhibited by contacting a cell with an RNA silencing agent that targets components of signaling pathways involving a miR145 target. For example, an exemplary miR145 target is IRS-1. Downstream signaling from IRS-1 activates MAPK and PI3K. Accordingly, in exemplary embodiments the invention provides methods of inhibiting HCMV replication by contacting a cell with an RNA silencing agent capable of mediating RNAi of IRS-1 in an amount effective to decrease the level of IRS-1, such that HCMV replication is inhibited. In other embodiments, the invention provides methods of inhibiting HCMV replication by contacting a cell with an RNA silencing agent capable of mediating RNAi of MAPK or PI3K in an amount effective to decrease the level of MAPK or PI3K, such that HCMV replication is inhibited. Accordingly, in exemplary embodiments, an RNA silencing agent has sufficient sequence complementarity to IRS-1

(SEQ ID NO:7), MAPK (SEQ ID NO:8), or PI3K (NM_181523.1, GI:32455247; NM_181504.2, GI:32455251; NM_006218.2, GI:54792081; NM_006219.1, GI:5453893; NM_005026.3, GI:156564404) to direct translational repression of IRS-1, MAPK, or PI3K, or to direct degradation of IRS-1, MAPK, or PI3K, e.g., through RNAi.

The foregoing methods may additionally comprise measuring the level of HCMV replication in a cell after contacting the cell with an RNA silencing agent, and comparing the level of HCMV replication to a suitable control. In this embodiment, a preferred RNA silencing agent, or a preferred quantity of a RNA silencing agent, is one which decreases the level of HCMV replication when compared to a suitable control, e.g., a comparable cell not contacted with a RNA silencing agent.

A cell that is contacted by an RNA silencing agent in accordance with the methods of the invention may be found within an organism. In this embodiment, administering an RNA silencing agent to an organism can inhibit HCMV proliferation, for example, in a cell within the organism that is contacted by the RNA silencing agent. In preferred embodiments, the organism is infected with HCMV. In these embodiments, administering an RNA silencing agent to the organism is used to treat HCMV infection. In other embodiments, the organism is at risk of contracting or developing an HCMV infection. In these embodiments, administering an RNA silencing agent to the organism is used to prevent HCMV infection. RNA silencing agents may be used, for example, for the treatment or prevention of HCMV-mediated diseases or disorders, e.g., HCMV retinitis, HCMV hepatitis, HCMV-mediated pneumonia, HCMV-mediated birth defects, cytomegalovirus infection associated with transplantation, e.g., transplantation of kidney, lung, liver, pancreas, and heart; and HCMV-mediated polyradiculopathy, encephalitis, gastrointestinal tract disease, myocarditis or pancreatitis. RNA silencing agents can also be used prophylactically, e.g., for the prophylaxis of cytomegalovirus disease associated with transplantation of kidney, lung, liver, pancreas, and heart, or for the prevention of HCMV-mediated congenital disorders.

C. Inhibition of HCMV Replication and Treatment of HCMV Infection Using miR132 Antagonists or miR212 Antagonists In one aspect, the invention provides methods of inhibiting HCMV replication in a cell, comprising contacting the cell with a miR132 antagonist in an amount effective to increase the level of one or more miR132 targets, or a gene product (e.g., a polypeptide) encoded by one or more miR132 targets, such that HCMV replication is inhibited. In another aspect, the invention provides methods of inhibiting HCMV replication in a cell, comprising contacting the cell with a miR212 antagonist in an amount effective to increase the level of one or more miR212 targets, or a gene product (e.g., a polypeptide) encoded by one or more miR212 targets, such that HCMV replication is inhibited. A miR132 or miR212 antagonist, as used herein, is an agent that reduces or inhibits the expression, stability, or activity or miR132 or miR212. Accordingly, miR132 or miR212 antagonists include, for example, antisense locked nucleic acid molecules (LNAs), antagomirs, or 2'O-methyl antisense RNAs targeting miR132 or miR212. In an exemplary embodiment, a miR132 antagonist comprises a nucleic acid molecule that is complementary to all or a part of the nucleic acid sequence of the stem-loop form of miR132, as set forth in SEQ ID NO:3: 5'CCGCCCCCGCGUCUCCA-GGGCAACCGUGGCUUUCGAUUGUUACUGUGG GAACUGGAGGUAACAGUCUACAGCCAUGGUCGC-CCCGCAGCACGCCCAC GCGC 3' (miRNA ID No: hsa-mir-132). In other exemplary embodiments, a miR132 agent comprises a nucleic acid molecule that is complementary to all or a part of the nucleic acid sequence of the mature, processed form of miR132, as set forth in SEQ ID NO:4: 5' UAACAGUCUACAGCCAUGGUCG 3'. In another exemplary embodiment, a miR212 antagonist comprises a nucleic acid molecule that is complementary to all or a part of the nucleic acid sequence of the stem-loop form of miR212, as set forth in SEQ ID NO:5:

CGGGGCACCCCGCCCGGACAGCGCGCCGGCAC-CUUGGCUCUAGAC UGCUUACUGCCCGGGCCGCC-CUCAGUAACAGUCUCCAGUCACGGCCACC GACGCCUGGCCCCGCC (miRNA ID No: hsa-miR-212). In another exemplary embodiment, a miR212 agent comprises a nucleic acid molecule that is complementary to all or a part of the nucleic acid sequence of the mature, processed form of miR212, as set forth in SEQ ID NO:6: UAACAGUCUCCAGUCACGGCC. Contacting a cell with a miR132 or miR212 antagonist compensates for the increase in miR132 or miR212 that occurs during HCMV infection, thereby negating any beneficial effect derived by HCMV as a consequence of miR132 or miR212 upregulation. In certain embodiments, a miR132 antagonist comprises nuclease resistant oligonucleotides that increase the stability of the miR132 antagonist. In other embodiments, a miR212 antagonist comprises nuclease resistant oligonucleotides that increase the stability of the miR212 antagonist.

In some embodiments, a miR132 antagonist contains a nucleic acid molecule that is fully complementary to a miR132 pre-RNA (SEQ ID NO:3) or to the mature form of miR132 (SEQ ID NO:4). In other embodiments, a miR132 antagonist contains a nucleic acid molecule that has 50% complementarity or more to a miR132 pre-RNA (SEQ ID NO:3) or to the mature form of miR132 (SEQ ID NO:4), wherein the miR132 antagonist has the ability to reduce or inhibit the expression, stability, or activity of miR132. In preferred embodiments, a miR132 antagonist contains a nucleic acid molecule having 60%, 70%, 80%, 90%, 95%, 99% or more complementarity with the nucleic acid sequence of a miR132 pre-RNA (SEQ ID NO:3) or with the sequence of mature miR132 (SEQ ID NO:4). In other embodiments, a miR132 antagonist contains a nucleic acid molecule that is fully complementary to the nucleic acid sequence of a miR132 pre-RNA (SEQ ID NO:3), or a mature miR132 (SEQ ID NO:4) at all but one or more (e.g., 1 2, 3, 4, 5, 6, 7, 8, 9, 10, 15, 20, 25 or more) nucleic acids, wherein the miR132 antagonist has the ability to reduce or inhibit the expression, stability, or activity of miR132.

In some embodiments, a miR212 antagonist contains a nucleic acid molecule that is fully complementary to a miR212 pre-RNA (SEQ ID NO:5) or to the mature form of miR212 (SEQ ID NO:6). In other embodiments, a miR212 antagonist contains a nucleic acid molecule that has 50% complementarity or more to a miR212 pre-RNA (SEQ ID NO:5) or to the mature form of miR212 (SEQ ID NO:6), wherein the miR212 antagonist has the ability to reduce or inhibit the expression, stability, or activity of miR212. In preferred embodiments, a miR212 antagonist contains a nucleic acid molecule having 60%, 70%, 80%, 90%, 95%, 99% or more complementarity with the nucleic acid sequence of a miR212 pre-RNA (SEQ ID NO:5) or with the sequence of mature miR212 (SEQ ID NO:6). In other embodiments, a miR212 antagonist contains a nucleic acid molecule that is fully complementary to the nucleic acid sequence of a miR212 pre-RNA (SEQ ID NO:5), or a mature miR212 (SEQ ID NO:6) at all but one or more (e.g., 1 2, 3, 4, 5, 6, 7, 8, 9, 10, 15, 20, 25 or more) nucleic acids, wherein the miR212 antagonist has the ability to reduce or inhibit the expression, stability, or activity of miR212.

In some embodiments, the foregoing miR132 and miR212 antagonists can comprise modified nucleotides, e.g., nuclease-resistant oligonucleotides. In some embodiments, the nucleotide modifications include modifications to the 2'sugar, for example, 2'-O-methyl (2'-OMe), 2'-O-methoxyethyl (2'-MOE), and 2'-flouro (2'F) modifications. miR132 antagonists can additionally or alternatively contain modifications to the phosphorothioate backbone.

In some embodiments, the foregoing miR132 and miR212 antagonists can comprise locked nucleic acids (LNAs). A LNA is a nucleic acid analogue containing one or more LNA nucleotide monomers with a bicyclic furanose unit locked in an RNA mimicking sugar conformation. The ribose moiety of an LNA nucleotide is modified with an extra bridge (e.g., a 2'-0,4'-C methylene bridge) connecting the 2' and 4' carbons. The bridge 'locks' the ribose in the 3'endo structural conformation, which is often found in the A-form of RNA. LNA oligonucleotides display unprecedented hybridization affinity toward complementary single-stranded RNA, including miRNA. Structural studies have shown that LNAs are effective RNA mimics that induce an A-type (RNA-like) duplex geometry. The locked ribose conformation of LNAs enhances base stacking and significantly increases the thermal stability of oligonucleotides containing LNAs. A triplet of LNA nucleotides surrounding a single-base mismatch site can maximize LNA binding specificity. miR132 and/or miR212 antagonists may also comprise chimaeric LNA/2'-O-methoxyethyl oligonucleotides. Chimaeric LNA/2'-O-methoxyethyl oligonucleotides have high thermal stability and potent inhibitory capability. An exemplary LNA useful as a miR132 antagonist has the following nucleic acid sequence: 5' CGA CCA TGG CTG TAG ACT GTT A 3' (SEQ ID NO:13). An exemplary LNA useful as a miR212 antagonist has the following nucleic acid sequence: 5' GGCCGTGACTGGAGACTGTTA 3' (SEQ ID NO:14).

In some embodiments, the foregoing miR132 and/or miR212 antagonists can be antagomirs. An antagomir is a small synthetic RNA-like oligonucleotide that is complementary to a specific miRNA target (e.g., miR132, miR212), and harbors various modifications for RNAse protection and pharmacologic properties such as enhanced tissue and cellular uptake. Antagomirs differ from normal RNA by complete 2'-O-methylation of sugar, phosphorothioate backbone and a cholesterol-moiety at 3'-end. Antagomirs efficiently silence miRNAs in most tissues after three injections at approximately 20-1000 mg/kg bodyweight (bw) (e.g., 20 mg/kg, 30 mg/kg, 40 mg/kg, 50 mg/kg, 60 mg/kg, 70 mg/kg, 80 mg/kg, 90 mg/kg, 100 mg/kg, 125 mg/kg, 150 mg/kg, 175 mg/kg 200 mg/kg, 500 mg/kg, 700 mg/kg, or 1000 mg/kg) on consecutive days. The synthesis and use of antagomirs is described further in Krutzfeldt, J. et al., Silencing of microRNAs in vivo with 'antagomirs' *Nature.* 2005; 438:685-689 and Krutzfeldt, J. et al., *Nucleic Acids Research,* 2007, Vol. 35, No. 9 2885-2892, the entire contents of which are incorporated herein by reference. In certain embodiments, antagomirs have either mispairing at the cleavage site of Ago2, or a base modification at this site to inhibit Ago2 cleavage. Antagomirs are believed to silence miRNA by irreversibly binding to miRNA molecules, rendering them nonfunctional.

In some embodiments, the foregoing miR132 and/or miR212 antagonists can comprise morpholino oligos (i.e., phosphorodiamidate morpholino oligos). Morpholino oligos are nucleic acid analogs having standard nucleic acid bases that are bound to morpholine rings, rather than to deoxyribose rings, and are linked through phosphorodiamidate groups, rather than phosphates. Based on the similarity to natural nucleic acid structure, morpholinos bind to complementary sequences of mRNA by standard Watson-Crick base pairing. Instead of degrading their target RNA molecules, morpholinos act by steric blocking, binding to a target sequence within an RNA (e.g., a miRNA, i.e., miR132 or miR212) and inhibiting interaction of molecules which might otherwise interact with the RNA. Morpholino oligos can be used to effectively inhibit the function of miR132 and/or miR212, thus serving as miR132 or miR212 antagonists.

The foregoing miR132 and/or miR212 antagonists can be conjugated to cholesterol to improve delivery to cells, tissues, or organisms. miR132 and miR212 antagonists can be conjugated to cholesterol in addition to or in alternative to the modifications described herein.

A cell that is contacted by a miR132 and/or a miR212 antagonist in accordance with the methods of the invention may be found within an organism. In this embodiment, administering an antagonist to an organism can inhibit HCMV proliferation, for example, in a cell within the organism that is contacted by the antagonist. In preferred embodiments, the organism is infected with HCMV. In these embodiments, administering a miR132 and/or miR212 antagonist to the organism is used to treat HCMV infection. In other embodiments, the organism is at risk of contracting or developing an HCMV infection. In these embodiments, administering a miR132 and/or miR212 antagonist to the organism is used to prevent HCMV infection. miR132 and/or miR212 antagonists may be used, for example, for the treatment or prevention of HCMV-mediated diseases or disorders, e.g., HCMV retinitis, HCMV hepatitis, HCMV-mediated pneumonia, HCMV-mediated birth defects, or cytomegalovirus infection associated with transplantation, e.g., transplantation of kidney, lung, liver, pancreas, and heart; and HCMV-mediated polyradiculopathy, encephalitis, gastrointestinal tract disease, myocarditis or pancreatitis. miR132 and/or miR212 antagonists can also be used prophylactically, e.g., for the prophylaxis of cytomegalovirus disease associated with transplantation of kidney, lung, liver, pancreas, and heart, or for the prevention of birth defects associated with HCMV.

D. Inhibition of HCMV Replication and Treatment of HCMV Infection Using miR132 Target Activating Agents and/or miR212 Target Activating Agents In another aspect, the invention provides methods of inhibiting HCMV replication in a cell, comprising contacting the cell with a miR132 target activating agent in an amount effective to increase the level of a miR132 target, such that HCMV replication is inhibited. In another aspect, the invention provides methods of inhibiting HCMV replication in a cell, comprising contacting the cell with a miR212 target activating agent in an amount effective to increase the level of a miR212 target, such that HCMV replication is inhibited. A miR132 target activating agent is an agent that increases, upregulates, enhances or mimics expression of a gene or gene product that is targeted by miR132. Likewise, a miR212 target activating agent is an agent that increases, upregulates, enhances or mimics expression of a gene or gene product that is targeted by miR212. Accordingly, a miR132 or miR212 target activating agent may include, for example, an expression vector encoding a miR132 or miR212 target, a synthetic RNA transcript encoding a miR132 or miR212 target, a miR132 or miR212 target polypeptide, a recombinant miR132 or miR212 target polypeptide, or an active domain thereof. Exemplary miR132 and/or miR212 target activating agents include, for example, an expression vector encoding MeCP2, a synthetic RNA transcript encoding MeCP2, a MeCP2 polypeptide (e.g., a purified MeCP2 polypeptide, a recombinant MeCP2 polypeptide), or an active domain of a MeCP2 polypeptide. Additional miR132 and/or miR212 target activating agents include, for example, an expression vector encoding RICS, a synthetic RNA transcript encoding RICS, a RICS polypeptide (e.g., a purified RICS polypeptide, a recombinant RICS polypeptide), or an active domain of a RICS polypeptide. Contacting a cell with a miR132 and/or miR212 target activating agent that increases, upregulates, enhances or mimics expression of a gene or gene product that is targeted by miR132 or miR212 compensates for the decrease in expression of miR132 targets that occurs as a result of miR132 and miR212 downregulation during HCMV infection. In this way, any beneficial effect derived by HCMV as a consequence of decreasing expression of miR132 or miR212 targets by upregulating miR132 or miR212 is negated. In certain embodiments, a miR132 or miR212 target activating agent comprises nuclease resistant oligonucleotides.

In some embodiments, a miR132 or miR212 target activating agent contains a nucleic acid molecule encoding MeCP2 (SEQ ID NO:9), or a biologically active portion thereof. In other embodiments, a miR132 or miR212 target activating agent contains a nucleic acid molecule encoding RICS (SEQ ID NO:11), or a biologically active portion thereof. In other embodiments, a miR132 or miR212 target activating agent contains a MeCP2 polypeptide (SEQ ID NO:10), or a biologically active portion thereof. In other embodiments, a miR132 or miR212 target activating agent contains a RICS polypeptide (SEQ ID NO:12), or a biologically active portion thereof.

In some embodiments, HCMV replication can be inhibited by contacting a cell with an agent that increases, upregulates, enhances or mimics expression of a gene or gene product that is a component of one or more signaling pathways involving a miR132 or miR212 target. For example, an exemplary miR132 target is RICS. Downstream signaling from RICS activates Cdc42 and Rac1. Accordingly, in exemplary embodiments the invention provides methods of inhibiting HCMV replication by contacting a cell with an agent capable of increasing the level or activation of Cdc42 and/or Rac1, such that HCMV replication is inhibited. In other embodiments, the invention provides methods of inhibiting HCMV replication by contacting a cell with an RNA agent capable of mediating RNAi of MAPK or PI3K in an amount effective to decrease the level of MAPK or PI3K, such that HCMV replication is inhibited.

A cell that is contacted by a miR132 or miR212 target activating agent in accordance with the methods of the invention may be found within an organism. In this embodiment, administering a miR132 or miR212 target activating agent to an organism can inhibit HCMV proliferation, for example, in a cell within the organism that is contacted by the miR132 or miR212 target activating agent. In preferred embodiments, the organism is infected with HCMV. In these embodiments, administering a miR132 or miR212 target activating agent to the organism is used to treat HCMV infection. In other embodiments, the organism is at risk of contracting or developing an HCMV infection. In these embodiments, administering a miR132 or miR212 target activating agent to the organism is used to prevent HCMV infection. miR132 or miR212 target activating agents may be used, for example, for the treatment or prevention of HCMV-mediated diseases or disorders, e.g., HCMV retinitis, HCMV hepatitis, HCMV-mediated pneumonia, HCMV-mediated birth defects, or cytomegalovirus infection associated with transplantation, e.g., transplantation of kidney, lung, liver, pancreas, and heart; and HCMV-mediated polyradiculopathy, encephalitis, gastrointestinal tract disease, myocarditis or pancreatitis. miR132 or miR212 target activating agents can also be used prophylactically, e.g., for the prophylaxis of cytomegalovirus disease associated with transplantation of kidney, lung, liver, pancreas, and heart, or for the prevention of birth defects associated with HCMV.

VII. miRNA Targets

A miRNA target (e.g., a miR145 target, a miR132 target, a miR212 target), as used herein, refers to a gene, gene transcript, or gene product whose expression is altered (e.g., downregulated) by a given miRNA (e.g., miR145, miR132, or miR212). miRNAs may alter the expression of a miRNA target by interacting with an RNA transcript, and preventing translation of a polypeptide encoded by the RNA transcript. In this case, the level of expression of a polypeptide encoded by the RNA transcript is decreased in the presence of the miRNA, while the level of the RNA transcript remains substantially unaltered. miRNAs may alternatively alter the expression of a miRNA target by interacting with an RNA transcript, and directing degradation or destabilization of the RNA transcript. In this case, the level of expression of the RNA transcript, and the level of a polypeptide encoded by the RNA transcript, are decreased in the presence of the miRNA (e.g., miR145, miR132, or miR212). In some embodiments, miRNA targets a non-coding RNA. In preferred embodiments, miR145, miR132, and miR212 target a mRNA encoding a polypeptide.

miRNA targets are identified based on having a region of sequence complementarity to a portion of miR145, miRNA132, or miRNA 212. In order to mediate post-transcriptional repression or degradation of targets, miRNAs must recognize their targets by complementary base pairing. miRNA targets typically have conserved Watson-Crick base pairing to a 5' region of a miRNA, known as the miRNA seed. Accordingly, in a preferred embodiment, miRNA targets contain a region that is complementary to 6-8 nucleotides in the miRNA seed. Four types of miRNA seed types are useful for miRNA target identification: the 6mer site, which perfectly matches the 6-nucleotide miRNA seed; the 7mer-m8 site, which comprises the seed match supplemented by a Watson-Crick base pair match to miRNA nucleotide 8, the 7mer-A1 site, which contains the seed match supplemented by an A across from miRNA nucleotide 1, and the 8-mer site, which contains the seed match supplemented by both the m8 and the A1 (Friedman et al., *Genome Res*. (2009) 19:92-105). The region within a miRNA target that is complementary to the miRNA seed may be located at any point within the gene transcript, but is preferably located within the 3'untranslated region (3'UTR) or within an open reading frame of a mRNA transcript.

Methods useful for identifying a miRNA target are known in the art, and are described, for example, in Friedman et al., *Genome Res*. (2009) 19:92-105, incorporated herein by reference in its entirety. Tools that are useful for identifying a miRNA target are maintained through the Whitehead Institute for Biomedical Research (see, for example, www.targetscan.org). miRNA targets identified according to the foregoing methods can be confirmed experimentally using techniques known in the art for determining whether the expression of a miRNA target is modulated (e.g., down-regulated) by a miRNA. As will be apparent to a person of skill in the art, such experiments can be performed in vivo, e.g., in a cell or organism, or in vitro, e.g. using a cell extract or recombinant nucleic acids and/or polypeptides. If levels of an RNA (e.g., an mRNA) decrease following exposure to a miRNA, the gene or gene product corresponding to the RNA may be a miRNA target. Likewise, if levels of an RNA (e.g., an mRNA) increase following disruption of an miRNA, the gene or gene product corresponding to the RNA may be a miRNA target. Similarly, if levels of a polypeptide encoded by a mRNA decrease following exposure to a miRNA, the gene or gene product corresponding to the RNA is a miRNA target. Likewise, if levels of a polypeptide encoded by a mRNA increase following disruption of a miRNA, the gene or gene product corresponding to the RNA is a miRNA target.

In exemplary embodiments, a miR145 target, a miR132 target, and/or a miR212 target is a component of an HCMV replication pathway, e.g., a signaling pathway. An HCMV replication pathway is a pathway, e.g., a signaling pathway, that, when altered, modulates HCMV replication. In an exemplary embodiment, a miR145 target is IRS-1. In another exemplary embodiment, a miR132 and/or miR212 target is MeCP2 or RICS.

VIII. Determining the Level of Expression of a miRNA Target

The level of expression of a miRNA target (e.g., a miR132 target, a miR212 target, a miR145 target, etc.) can be determined using any suitable method known in the art for measuring RNA or protein expression. Such methods include, for example, Northern blot, quantitative Real-Time PCR (qRT-PCR), microarray, in situ hybridization, Western blot, ELISA, or antibody microarray.

The applications described herein can require comparison with a suitable control sample. Such suitable controls will be obvious to one skilled in the art and are considered part of the common knowledge. For example, when contacting a cell with a miR145 agent in an amount effective to decrease the level of one or more miR145 targets, a decrease in the level of one or more miR145 targets may be compared with the level of the miR145 target in a like cell that is not contacted with a miR145 agent (e.g., a mock-transfected cell). When determining the decrease in the level of one or more miR145 targets in response to a miR145 agent, a suitable control may include, for example, a cell infected with HCMV that is not contacted with a miR145 agent. In another example, when contacting a cell with a miR132 and/or miR212 antagonist in an amount effective to increase the level of one or more miR132 or miR212 targets, an increase in the level of one or more targets may be compared with the level of the target in a like cell that is not contacted with a miR132 or miR212 antagonist (e.g., a mock-transfected cell). When determining the increase in the level of one or more miR132 or miR212 targets in response to a miR132 or miR212 antagonist, a suitable control may include, for example, a cell infected with HCMV that is not contacted with a miR132 or miR212 antagonist.

When contacting a cell with an RNA silencing agent capable of mediating expression of a miR145 target (e.g., by RNA interference), a decrease in the level of the miR145 target may be compared with the level of the miR145 target in a like cell that is not contacted with the RNA silencing agent (e.g., a mock-transfected cell). When determining the decrease in the level of a miR145 target in response to an RNA silencing agent, a suitable control may include, for example, a cell infected with HCMV that is not contacted with an RNA silencing agent. Likewise, when contacting a cell with a miR132 or miR212 target activating agent capable of increasing or upregulating expression of a gene or gene product that is targeted by miR132 and/or miR212, an increase in the level of the miR132 or miR212 target may be compared with the level of the target in a like cell that is not contacted with the activating agent (e.g., a mock-transfected cell). When determining the increase in the level of a miR132 or miR212 target in response to a miR132 or miR212 target activating agent, a suitable control may include, for example, a cell infected with HCMV that is not contacted with the agent.

IX. Pharmaceutical Compositions miR145 agents, and RNA silencing agents capable of mediating expression of a miR145 target, can be used therapeutically or prophylactically either alone or in combination. Accordingly, the present invention provides compositions comprising a miR145 agent and/or an RNA silencing agent as described herein, and a pharmaceutically acceptable carrier. The invention further provides methods of treating or attenuating HCMV infection in an organism by administering compositions that include a miR145 agent and/or an RNA silencing agent as described herein, or a pharmaceutical composition including the same.

miR132 antagonists, miR212 antagonists, miR132 target activating agents, and miR212 target activating agents can be used therapeutically or prophylactically either alone or in combination. Accordingly, the present invention provides compositions comprising a miR132 antagonist, a miR212 antagonist, a miR132 target activating agent, a miR212 target activating agent, and combinations thereof, as described herein, and a pharmaceutically acceptable carrier. The invention further provides methods of treating or attenuating HCMV infection in an organism by administering compositions that include a miR132 antagonist, a miR212 antagonist, a miR132 target activating agent, a miR212 target activating agent, and combinations thereof as described herein, or a pharmaceutical composition including the same.

The invention pertains to uses of the above-described agents for therapeutic treatments as described infra. Accordingly, the agents of the present invention can be incorporated into pharmaceutical compositions suitable for administration. As used herein the language "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Examples of routes of administration include parenteral, e.g., intravenous, intradermal, subcutaneous, intraperitoneal, intramuscular, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer. Such methods include those described in U.S. Pat. No. 6,468,798.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

The compounds can also be administered by transfection or infection using methods known in the art, including but not limited to the methods described in McCaffrey et al. (2002), Nature, 418(6893), 38-9 (hydrodynamic transfection); Xia et al. (2002), Nature Biotechnol., 20(10), 1006-10 (viral-mediated delivery); or Putnam (1996), Am. J. Health Syst. Pharm. 53(2), 151-160, erratum at Am. J. Health Syst. Pharm. 53(3), 325 (1996).

In some embodiments, the pharmaceutical compositions described herein (and other optional pharmacological agents) can be delivered directly via a pump device. For example, in some embodiments, the compositions are delivered directly by infusion into a diseased tissue, e.g. a tissue that is infected with HCMV.

The compounds can also be administered by any method suitable for administration of nucleic acid agents, such as a DNA vaccine. These methods include gene guns, bio injectors, and skin patches as well as needle-free methods such as the micro-particle DNA vaccine technology disclosed in U.S. Pat. No. 6,194,389, and the mammalian transdermal needle-free vaccination with powder-form vaccine as disclosed in U.S. Pat. No. 6,168,587. Additionally, intranasal delivery is possible, as described in, inter alia, Hamajima et al. (1998), Clin. Immunol. Immunopathol., 88(2), 205-10. Liposomes (e.g., as described in U.S. Pat. No. 6,472,375) and microencapsulation can also be used. Biodegradable targetable microparticle delivery systems can also be used (e.g., as described in U.S. Pat. No. 6,471,996).

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the compound which achieves a half-maximal inhibition of symptoms) as determined in cell culture. Such information can be used to more accurately determine useful doses in humans. Levels in plasma may be measured, for example, by high performance liquid chromatography.

In some embodiments, a therapeutically effective amount of a composition containing a compound of the invention (e.g., a miR145 agent, etc.) (i.e., an effective dosage) is an amount that increases expression of miR145 or miR145 activity (e.g., translational repression of one or more miR145 targets) by at least 10 percent. Higher percentages, e.g., 20, 30, 40, 50, 60, 70, 80, 90, 100, 150, 100 percent or higher may be preferred in certain embodiments. Exemplary doses include milligram or microgram amounts of the molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. The compositions can be administered one time per week for between about 1 to 10 weeks, e.g., between 2 to 8 weeks, or between about 3 to 7 weeks, or for about 4, 5, or 6 weeks. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a composition can include a single treatment or a series of treatments.

In some embodiments, a therapeutically effective amount of a composition containing a compound of the invention (e.g., an RNA silencing agent, etc.) (i.e., an effective dosage) is an amount that inhibits expression of the polypeptide encoded by a miR145 target by at least 30 percent. Higher percentages of inhibition, e.g., 45, 50, 75, 85, 90 percent or higher may be preferred in certain embodiments. Exemplary doses include milligram or microgram amounts of the molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. The compositions can be administered one time per week for between about 1 to 10 weeks, e.g., between 2 to 8 weeks, or between about 3 to 7 weeks, or for about 4, 5, or 6 weeks. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a composition can include a single treatment or a series of treatments.

In other embodiments, a therapeutically effective amount of a composition containing a compound of the invention (e.g., a miR132 antagonist, a miR212 antagonist, etc.) (i.e., an effective dosage) is an amount that inhibits expression of miR132 or miR132 activity (e.g., translational repression of one or more miR132 targets) by at least 30 percent, or an amount that inhibits expression of miR212 or miR212 activity (e.g., translational repression of one or more miR212 targets) by at least 30 percent. Higher percentages of inhibition, e.g., 45, 50, 75, 85, 90 percent or higher may be preferred in certain embodiments. Exemplary doses include milligram or microgram amounts of the molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. The compositions can be administered one time per week for between about 1 to 10 weeks, e.g., between 2 to 8 weeks, or between about 3 to 7 weeks, or for about 4, 5, or 6 weeks. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a composition can include a single treatment or a series of treatments.

In some embodiments, a therapeutically effective amount of a composition containing a compound of the invention (e.g., a miR132 target activating agent, a miR212 target activating agent, etc.) (i.e., an effective dosage) is an amount that increases expression or activation of a miR132 or miR212 target by at least 10 percent. Higher percentages, e.g., 20, 30, 40, 50, 60, 70, 80, 90, 100, 150, 100 percent or higher may be preferred in certain embodiments. Exemplary doses include milligram or microgram amounts of the molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. The compositions can be administered one time per week for between about 1 to 10 weeks, e.g., between 2 to 8 weeks, or between about 3 to 7 weeks, or for about 4, 5, or 6 weeks. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a composition can include a single treatment or a series of treatments.

It is furthermore understood that appropriate doses of a composition depend upon the potency of composition with respect to the expression or activity to be modulated. When one or more of these molecules is to be administered to an animal (e.g., a human) to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

The pharmaceutical compositions can be included in a container, pack, or dispenser together with instructions for administration.

X. Additional Agents

Compositions comprising a miR145 agent, an RNA silencing agent capable of mediating expression of a miR145 target (e.g. downregulating a miR145 target), a miR132 antagonist, a miR212 antagonist, a miR132 target activating agent, a miR212 target activating agent, and combinations thereof, and pharmaceutical compositions comprising the same, may be used in the methods of the invention in combination with additional therapeutic agents. Such additional agents preferably contribute to the inhibition of HCMV replication or to the treatment of HCMV infection. Accordingly, in certain embodiments, the foregoing compositions are used in combination with an antiviral agent. The antiviral agent may be used to contact cells prior to, simultaneous with, or subsequent to contacting cells with a miR145 agent, an RNA silencing agent capable of mediating expression of a miR145 target, a miR132 antagonist, a miR212 antagonist, a miR132 target activating agent, a miR212 target activating agent, or combinations thereof. Likewise, the antiviral agent may be administered to a subject prior to, simultaneous with, or subsequent to administration of a miR145 agent, an RNA silencing agent capable of mediating expression of a miR145 target, a miR132 antagonist, a miR212 antagonist, a miR132 target activating agent, a miR212 target activating agent, or combinations thereof.

In exemplary embodiments, the antiviral agent is Ganciclovir, Valganciclovir, Cidofovir, Foscarnet, Formivirsen, Acyclovir, Valacyclovir, CMX001, Artesunate, BAY-384766, T-611, GW-275175X, or Maribavir. Dosages and administration schedules of the foregoing agents that are routine in the art are suitable for use in combination with the foregoing compositions.

XI. Detecting an HCMV Infection

The invention further provides methods of detecting an HCMV infection in a subject, comprising determining a level of miR145 expression in a subject, and comparing the level of miR145 expression to a suitable control, wherein a reduction in the level of miR145 expression relative to the suitable control indicates the presence of an HCMV infection in the subject.

The invention likewise provides methods of detecting an HCMV infection in a subject, comprising determining a level of miR132 expression in a subject, and comparing the level of miR132 expression to a suitable control, wherein an increase in the level of miR132 expression relative to the suitable control indicates the presence of an HCMV infection in the subject.

The invention also provides methods of detecting an HCMV infection in a subject, comprising determining a level of miR212 expression in a subject, and comparing the level of miR212 expression to a suitable control, wherein an increase in the level of miR212 expression relative to the suitable control indicates the presence of an HCMV infection in the subject.

Certain methods of the invention, including the foregoing diagnostic methods, require determining the expression level of miR145, miR132, and/or miR212 in a cell or in a biological sample, e.g., a biological sample obtained from a subject. Methods for determining miRNA expression levels in cells or biological samples are within the level of skill in the art. Such methods include, but are not limited to, northern blot analysis, in situ hybridization, microarray analysis, and quantitative reverse transcriptase polymerase chain reaction. Total cellular RNA can be purified from cells by homogenization in the presence of nucleic acid extraction buffer, followed by centrifugation. Nucleic acids are precipitated, and DNA is removed by treatment with DNase and precipitation.

RNA molecules can be separated by gel electrophoresis on agarose gels according to standard techniques, and transferred to nitrocellulose filters by, e.g., the so-called "Northern Blot" technique. The RNA is then immobilized on the filters by heating. Detection and quantification of specific RNA is accomplished using appropriately labeled DNA or RNA probes complementary to the RNA in question (see, for example, *Molecular Cloning: A Laboratory Manual*, J. Sambrook et al., eds., $2^{nd}$ Edition, Cold Spring Harbor Laboratory Press, 1989, Chapters 10 and 11, the disclosures of which are incorporated herein by reference.

Suitable probes for Northern blot hybridization of a given miRNA gene product can be produced using the nucleotide sequence of an miRNA. The sequence of the stem-loop form of miR145 is as follows: 5'CACCUUGUCCUCACGGUC-CAGUUUUCCCAGGAAUCCCUUAGAUGCUAA GAUGGGGAUUCCUGGAAAUACUGUUCUUGAGGU-CAUGGUU3' (SEQ ID NO:1) (miRNA ID No: hsa-mir-145; Accession No: MI0000461). The sequence of the mature, processed form of miR145 is as follows: 5' GUC-CAGUUUUCCCAGGAAUCCCU 3' (SEQ ID NO:2). Likewise, the sequence of the stem-loop form of miR132 is as follows: 5'CCGCCCCCGCGUCUCCAGGGCAACCGUG-GCUUUCGAUUGUUACUGUGG GAACUGGAG-GUAACAGUCUACAGCCAUGGUCGCCCCGCAG-CACGCCCAC GCGC 3' (SEQ ID NO:3) (miRNA ID No: hsa-mir-132). The sequence of the mature, processed form of miR132 is as follows: 5' UAACAGUCUACAGCCAUG-GUCG 3' (SEQ ID NO:4). The sequence of the stem-loop form of miR212 is as follows: 5' CGGGGCACCCCGC-CCGGACAGCGCGCCGGCACCUUGGCUCUA-GACUGCU UACUGCCCGGGCCGCCCUCAGUAACA-GUCUCCAGUCACGGCCACCGACG CCUGGCCCCGCC 3' (SEQ ID NO:5) (miRNA ID No: hsa-miR-212). The sequence of the mature, processed form of miR132 is as follows: 5' UAACAGUCUCCAGUCACG-GCC 3' (SEQ ID NO:6).

Methods for preparation of labeled DNA and RNA probes, and the conditions for hybridization thereof to target nucleotide sequences, are described in *Molecular Cloning: A Laboratory Manual*, J. Sambrook et al., eds., 2nd edition, Cold Spring Harbor Laboratory Press, 1989, Chapters 10 and 11, the disclosures of which are herein incorporated by reference.

For example, the nucleic acid probe can be labeled with, e.g., a radionuclide such as $^{3}H$, $^{32}P$, $^{33}P$, $^{14}C$, or $^{35}S$; a heavy metal; or a ligand capable of functioning as a specific binding pair member for a labeled ligand (e.g., biotin, avidin or an antibody), a fluorescent molecule, a chemiluminescent molecule, an enzyme or the like.

Probes can be labeled to high specific activity by either the nick translation method of Rigby et al. (Rigby (1977), *J. Mol. Biol.* 113:237-251), or by the random priming method of Fienberg et al. (Fienberg (1983), *Anal. Biochem.* 132:6-13, the entire disclosures of which are herein incorporated by reference. The latter is the method of choice for synthesizing $^{32}$P-labeled probes of high specific activity from single-stranded DNA or from RNA templates. For example, by replacing preexisting nucleotides with highly radioactive nucleotides according to the nick translation method, it is possible to prepare $^{32}$P-labeled nucleic acid probes with a specific activity well in excess of $10^8$ cpm/microgram. Autoradiographic detection of hybridization can then be performed by exposing hybridized filters to photographic film. Densitometric scanning of the photographic films exposed by the hybridized filters provides an accurate measurement of miRNA gene transcript levels. Using another approach, miRNA gene transcript levels can be quantified by computerized imaging systems, such the Molecular Dynamics 400-B 2D Phosphorimager available from Amersham Biosciences, Piscataway, N.J.

Where radionuclide labeling of DNA or RNA probes is not practical, the random-primer method can be used to incorporate an analogue, for example, the dTTP analogue 5-(N—(N-biotinyl-epsilon-aminocaproyl)-3-aminoallyl)deoxyuridine triphosphate, into the probe molecule. The biotinylated probe oligonucleotide can be detected by reaction with biotin-binding proteins, such as avidin, streptavidin, and antibodies (e.g., anti-biotin antibodies) coupled to fluorescent dyes or enzymes that produce color reactions.

In addition to Northern and other RNA blotting hybridization techniques, determining the levels of miRNA transcripts can be accomplished using the technique of in situ hybridization. This technique requires fewer cells than the Northern blotting technique, and involves depositing whole cells onto a microscope cover slip and probing the nucleic acid content of the cell with a solution containing radioactive or otherwise labeled nucleic acid (e.g., cDNA or RNA) probes. This technique is particularly well-suited for analyzing tissue biopsy samples from subjects. The practice of the in situ hybridization technique is described in more detail in U.S. Pat. No. 5,427,916, the entire disclosure of which is incorporated herein by reference. Suitable probes for in situ hybridization of a given miRNA gene product can be produced using the nucleotide sequence of an miRNA. In an exemplary embodiment, probes are produced using the nucleic acid sequence of human miR145 (SEQ ID NO:1, SEQ ID NO:2). In another exemplary embodiment, probes are produced using the nucleic acid sequence of human miR132 (SEQ ID NO:3, SEQ ID NO:4). In another exemplary embodiment, probes are produced using the nucleic acid sequence of human miR212 (SEQ ID NO:5, SEQ ID NO:6).

The relative number of miRNA gene transcripts in cells can also be determined by reverse transcription of miRNA gene transcripts, followed by amplification of the reverse-transcribed transcripts by polymerase chain reaction (RT-PCR). The levels of miRNA gene transcripts can be quantified in comparison with an internal standard, for example, the level of mRNA from a "housekeeping" gene present in the same sample. A suitable "housekeeping" gene for use as an internal standard includes, e.g., myosin or glyceraldehyde-3-phosphate dehydrogenase (GAPDH). The methods for quantitative RT-PCR and variations thereof are within the level of skill in the art.

In some embodiments, it is desirable to simultaneously determine the expression level of a plurality of different of miRNAs in a sample. Assessing expression levels for multiple miRNAs is time consuming and requires a large amount of total RNA (at least 20 μg for each Northern blot) and autoradiographic techniques that require radioactive isotopes. To overcome these limitations, an oligolibrary in microchip format may be constructed containing a set of probe oligonucleotides specific for a set of miRNA genes. In one embodiment, the oligolibrary contains probes corresponding to all known miRNAs from the human genome.

The nucleic acid sequences corresponding to miRNA, miRNA* and hairpin miRNAs of miR145, miR132, and miR212 are suitable for use in designing probes, oligonucleotides, primers, etc. for use in the methods and applications of the invention.

Cells or biological samples obtained from a normal cell, tissue, or organism (e.g., one which exhibits normal traits), as described above, can comprise suitable controls for the diagnostic methods set forth herein. The relative miRNA expression in the control or normal samples can further be determined with respect to one or more RNA expression standards. The standards can comprise, for example, a zero miRNA gene expression level, the miRNA gene expression level in a standard cell line, or the average level of miRNA gene expression obtained for a population of normal human controls. Alternatively, a feature of a control sample, for example, a value, level, characteristic, property, etc., has been predefined (e.g., a level of expression of an miRNA, a hybridization signal profile, etc.). In this embodiment, the miRNA expression levels present in a sample are compared with the pre-determined features of a control sample.

XII. Kits Comprising a miR145 Agent or an RNA Silencing Agent Capable of Mediating Expression of a miR145 Target The invention additionally provides kits comprising a composition comprising a miR145 agent, and instructions for administration of the composition to a subject for treating HCMV, for preventing HCMV, or for inhibiting replication of HCMV. In particular embodiments, the miR145 agent is a miR145 mimic, a synthetic miR145 oligonucleotide, or an expression vector encoding miR145.

The invention further provides kits comprising a composition comprising an RNA silencing agent capable of reducing expression of a miR145 target, an instructions for administration of the composition to a subject for treating HCMV, for preventing HCMV, or for inhibiting replication of HCMV. In exemplary embodiments, the RNA silencing agent is an siRNA, a shRNA, an antisense RNA, or a ribozyme. In one embodiment, the miR145 target is IRS-1.

The invention additionally provides kits comprising a composition containing a miR132 antagonist or a miR212 antagonist, or combinations thereof, and instructions for administration of the composition to a subject for treating HCMV, for preventing HCMV, or for inhibiting replication of HCMV. In particular embodiments, the miR132 antagonist is an antisense locked nucleic acid (LNA), an antagomir, or a 2'O-methyl antisense RNA targeting miR132. In other embodiments, the miR212 antagonist is an antisense locked nucleic acid (LNA), an antagomir, or a 2'O-methyl antisense RNA targeting miR212.

The invention further provides kits comprising a composition containing a miR132 target activating agent or a miR212 target activating agent, or a combination thereof, and instructions for administration of the composition to a subject for treating HCMV, for preventing HCMV, or for inhibiting replication of HCMV. In exemplary embodiments, the miR132 target activating agent is an expression vector encoding a miR132 target, a synthetic miR132 target RNA transcript, a miR132 target polypeptide, a recombinant miR132 target polypeptide, or an active portion of a miR132 target polypeptide. In other embodiments, the miR212 target activating agent is an expression vector encoding a miR212 target, a synthetic miR212 target RNA transcript, a miR212 target polypeptide, a recombinant miR212 target polypeptide, or an active portion of a miR212 target polypeptide. In certain embodiments, the miR132 and/or miR212 target is MeCP2 or RICS.

The kits of the invention may additionally contain an additional therapeutic agent. In a preferred embodiment, the additional therapeutic agent is an antiviral agent that contributes to inhibition of HCMV replication, treatment of HCMV infection, or prevention of HCMV infection. In exemplary embodiments, the kits of the invention contain Ganciclovir, Valganciclovir, Cidofovir, Foscarnet, Formivirsen, Acyclovir, Valacyclovir, CMX001, Artesunate, BAY-384766, T-611, GW-275175X, or Maribavir.

This invention is further illustrated by the following examples which should not be construed as limiting. The contents of all references, patents and published patent applications cited throughout this application are incorporated herein by reference in their entirety.

EXAMPLES

Example 1: miR145 is Downregulated Following HCMV Infection

Figure 2:
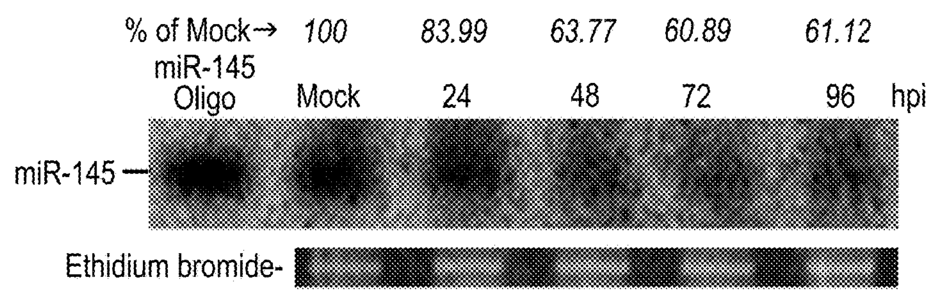
FIG. 2 depicts miR145 downregulation in HEL fibroblasts at 24, 48, 72, and 96 hours post-infection with HCMV, as determined by Northern blot.

Microarray analysis was performed to determine the miRNA expression pattern changes after HCMV infection. HEL fibroblasts were infected with HCMV (Multiplicity of infection (MOI)=5). RNA from mock-infected cells, together with RNA from cells infected with HCMV (48 hours post infection (hpi)), were hybridized to miRNA microarrays (LC Sciences). Hybridization signal intensities for individual miRNAs (average of six replicates) were plotted as mock versus virus-infected. Statistical analysis was performed at LC Sciences, and an additional Golub analysis was performed for maximum confidence. The results of the microarray analysis are depicted in FIG. 1. Red dots indicate statistically significant values ($p<0.01$). Greater than two-fold changes in miRNA expression appear outside of the diagonal lines. The arrow indicates that miR145 is significantly downregulated following HCMV infection (2.31 fold decrease). These data suggest that miR145 is involved in the pathogenesis of HCMV.

miR145 downregulation during HCMV infection was confirmed by Northern blot. HEL fibroblasts were infected with HCMV (MOI=1), and pellets were collected at 24, 48, 72 and 96 hpi. RNA was extracted and 5 μg of RNA from each sample was loaded and electrophoresed in a 15% acrylamide gel. RNA was transferred to a nylon-hybond membrane and a Northern blot was performed. The results of Northern blot analysis are depicted in FIG. 2. Ethidium bromide staining of the gel is shown as a loading control. These data show a sustained downregulation of miR145 levels throughout the time course of infection. These results confirm that HCMV downregulates miR145 expression.

Figure 3:
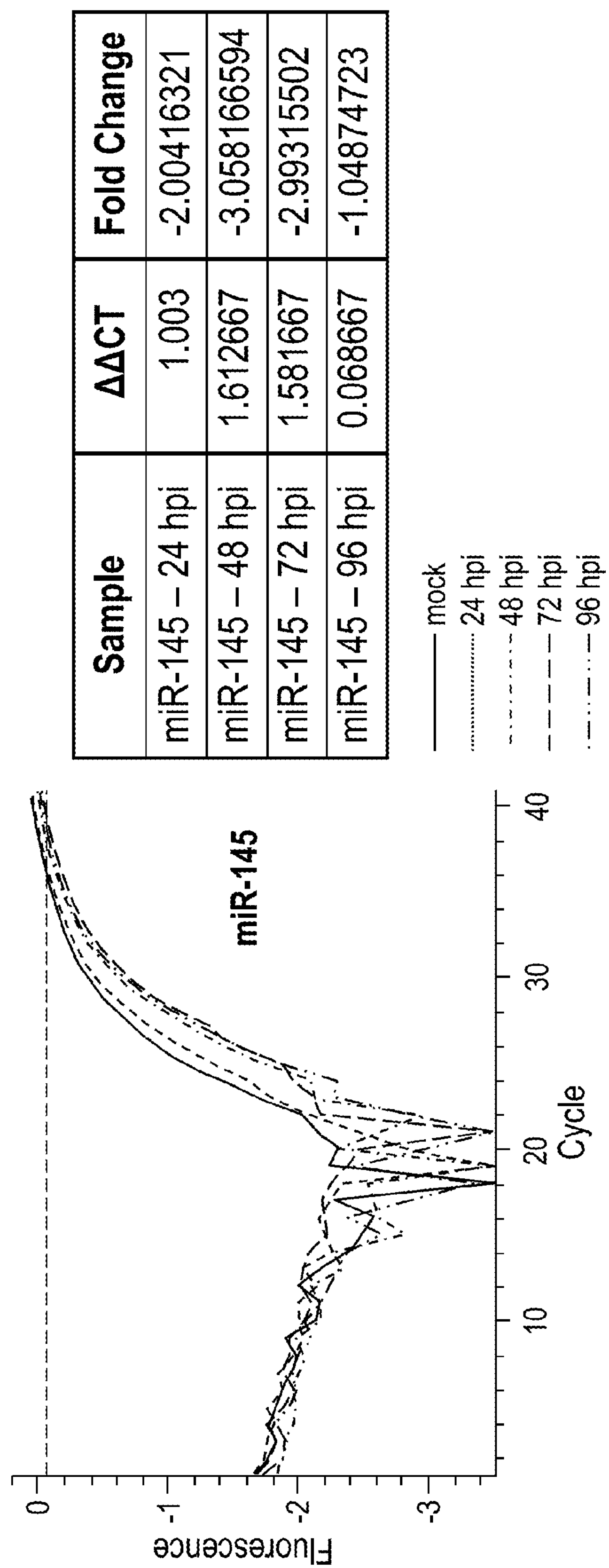
FIG. 3 depicts the expression level of miR145 in HEL fibroblasts at 24, 48, 72, and 96 hours post-infection with HCMV, as determined by quantitative Real Time PCR (qRT-PCR).

The infection-induced decrease in miR145 levels determined by microarray and Northern blot was further confirmed by quantitative Real Time PCR (qRT-PCR). HEL fibroblasts were infected with HCMV (MOI=1), and cell pellets were collected at 24, 48, 72 and 96 hpi. RNA was extracted using Trizol reagent (Invitrogen), and 5 ng of RNA was used for qRT-PCR (TaqMan® MicroRNA Assays, Applied Biosystems). As shown in FIG. 3, miR145 levels are downregulated, as noted by the increase in the cycle threshold (ΔΔCT). A 2-fold decrease at 24 hpi followed by a ~3-fold decrease at 48 hpi (which was sustained until 72 hpi) was detected during the time course infection. These results indicate that mature miR145 levels are reduced from 24 hpi to 72 hpi, further demonstrating that miR145 expression is decreased during HCMV infection. These data are in agreement with data obtained from microarray and Northern blot, indicating that miR145 has a role in HCMV pathogenesis.

Figure 4:
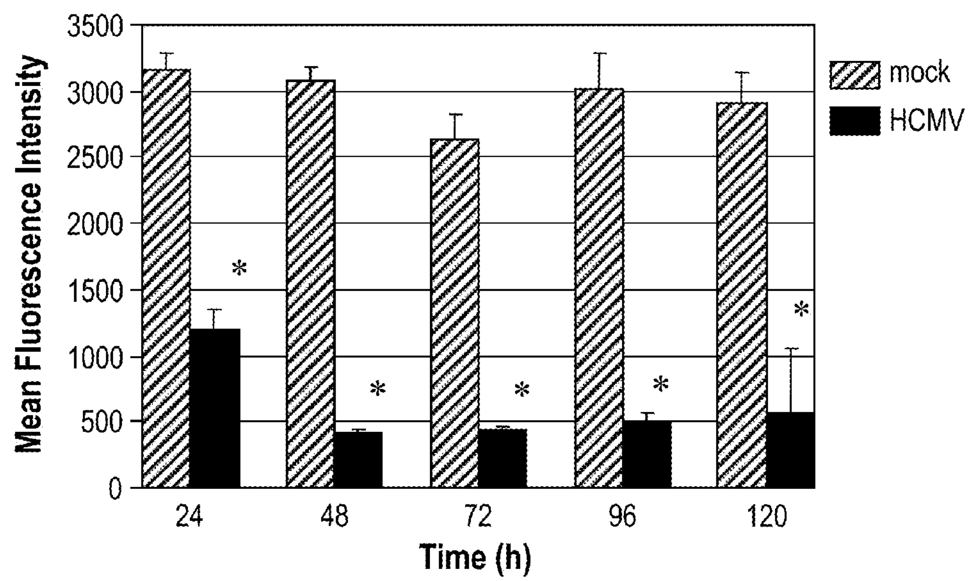
FIG. 4 depicts the results of a microarray time course analysis showing the change in miR145 levels in cells 24-120 hours after HCMV infection.

A microarray time course analysis was also performed to determine changes in miR145 levels after HCMV infection. HEL fibroblasts were infected with HCMV (MOI=5). RNA from mock-infected cells, together with RNA from cells infected with HCMV, was hybridized to miRNA microarrays (LC Sciences). Hybridization signal intensities for miR145 (average of 3 replicates) are plotted during the mock and virus-infected time course (FIG. 4). Statistical analysis was performed at LC Sciences. The results, shown in FIG. 4, indicate that miR145 levels are significantly and consistently downregulated during HCMV infection. (*=$p<0.05$)

Figure 5:
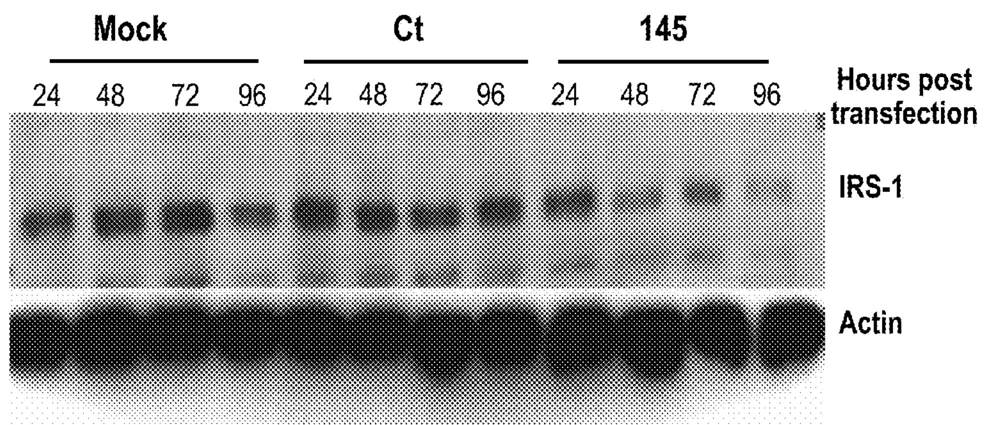
FIG. 5 depicts downregulation in IRS-1 protein levels in HEL fibroblasts following transfection with a miR145 mimic (145), as compared to transfection with a control miRNA (ct) or mock transfected cells.

Example 2: Transfection with a miR145 Mimic Leads to Decreased Levels of IRS-1 Protein This experiment was performed to determine whether a miR145 mimic targets Insulin Receptor Substrate-1 (IRS-1) mRNA, which is a target of miR145, in HEL fibroblasts. HEL fibroblasts were transfected with either a control miRNA (ct) or miR145 mimic (145) (Dharmacon). Cell pellets were collected at 24, 48, 72 and 96 hours post transfection and lysed. Western blot was performed using an anti IRS-1 antibody (Upstate Biothechnology). Actin is shown as a loading control. Downregulation of the IRS-1 protein was observed at 48, 72 and 96 hours post transfection with the miR145 mimic, when compared to control transfected cells, as shown in FIG. 5. This downregulation is not observed in the cells transfected with a control miRNA, or the mock-transfected cells. These data suggest that miR145 targets IRS-1 mRNA in HEL fibroblasts. Since miR145 is downregulated during HCMV infection, it is likely that IRS-1 is upregulated during HCMV infection.

Example 3: Transfection with a miR145 Mimic Reduces Viral Replication

Figure 6:
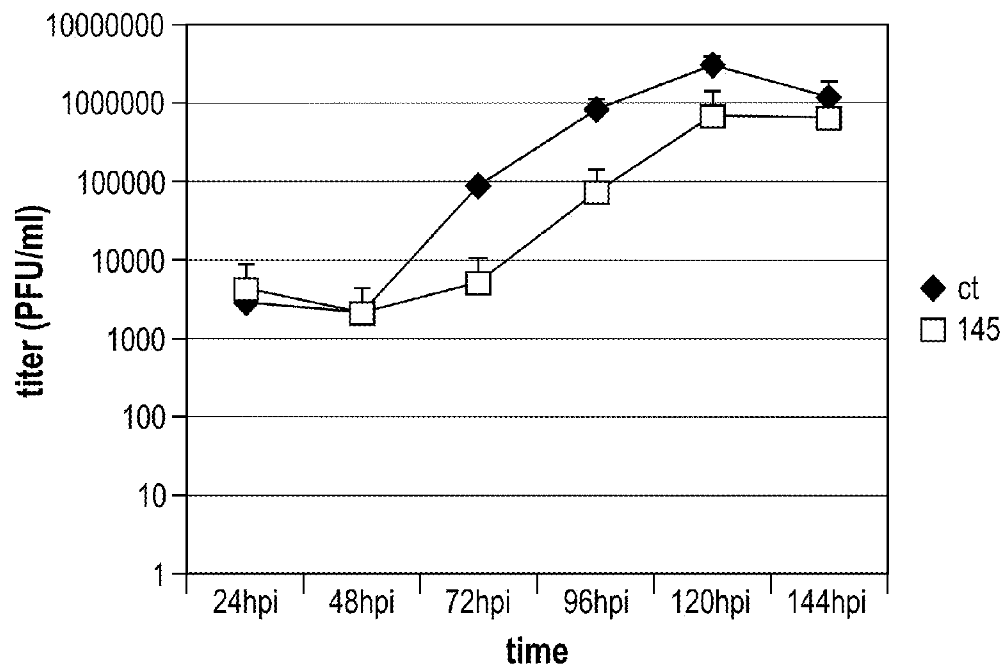
FIG. 6 graphically depicts the reduction in viral replication in HEL fibroblasts that occurs following transfection with a miR145 mimic (145), as compared to transfection with a control miRNA (ct).

This experiment was performed to determine whether altered regulation of miR145 following viral infection affects viral replication. HEL fibroblasts were transfected with either a control (ct) miRNA or a miR145 mimic (145) (Dharmacon). The cells were infected with HCMV (MOI=1) 24 hours after transfection. Supernatants were collected at 24, 48, 72, 96, 120 and 144 hpi and examined for viral titers by plaque assay. These results show decreased viral titers in the supernatants of HEL fibroblasts previously transfected with miR145, when compared to those transfected with the control miRNA, as shown in FIG. 6. A 10-fold difference can be observed from 72 to 96 hpi. At 144 hpi, viral titers are similar in the control and miR145 mimic transfected cells. This result may be due either to miR145 mimic turnover or to HCMV overcoming the effects of miR145 mimic transfection. These data suggest that miR145 transfection decreases viral replication in HEL fibroblasts, and implies a role for miR145 supporting viral replication. This is consistent with the hypothesis that downregulation of miR145 contributes to HCMV pathogenesis by enhancing its replication.

Example 4: miR145 Leads to Decreased HCMV Protein Expression

Figure 7:
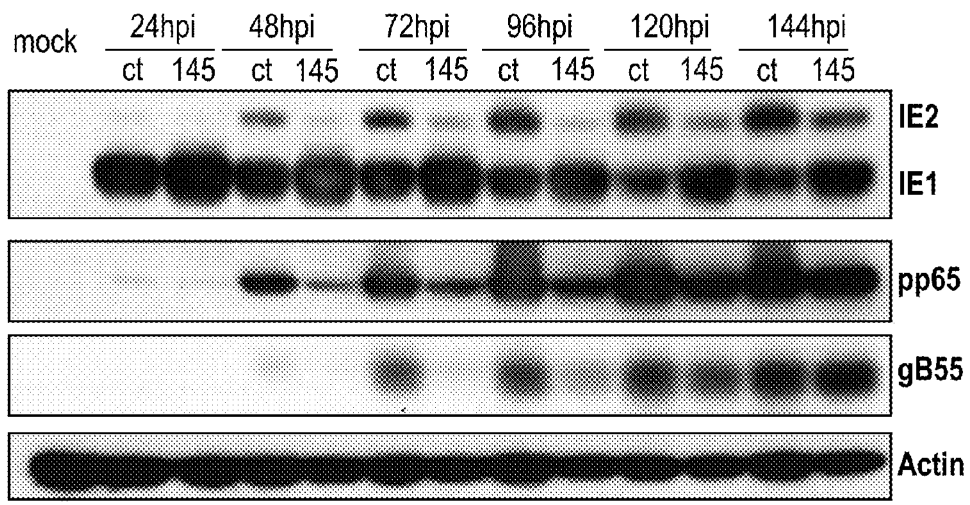
FIG. 7 depicts the reduction in expression of the HCMV proteins IE2, pp65, and gB55 that occurs in HEL fibroblasts previously transfected with a miR145 mimic (145) at 24, 48, 72, 96, 120, and 144 hours post-infection with HCMV, as compared to cells transfected with a control miRNA (ct).

These experiments were performed to establish the role of miR145 on HCMV protein expression. HEL fibroblasts were transfected with either a control miRNA or miR145 mimic (Dharmacon). The cells were infected with HCMV (MOI=1) 24 hours after transfection. Cell pellets were collected at 24, 48, 72, 96, 120 and 144 hpi, lysed and examined for viral protein expression by western blot. Decreased levels of the Immediate Early (IE) 2 protein, the Early (E) protein pp65, and the Late (L) protein gB55 could be seen in those cells transfected with miR145, when compared to the cells transfected with a control miRNA, as shown in FIG. 7. Increased IE1 levels were also observed, likely due to the decreased levels of IE2, as IE2 reduces IE1 expression (Hermiston et al 1990). Actin is shown in FIG. 7 as a loading control. These results indicate that miR145 transfection regulates the HCMV gene expression in HEL fibroblasts. These data implicate miR145 during HCMV IE, E and L gene expression. In agreement with the data in the previous figures, these results suggest that miR145 mediates HCMV pathogenesis and replication.

Example 5: HCMV Infection Upregulates IRS-1 Protein Levels

Figure 8A:
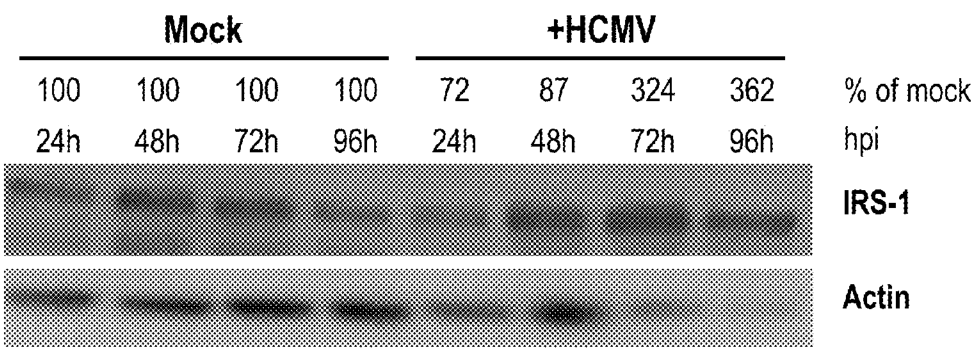
FIG. 8A-FIG. 8B depict upregulation in IRS-1 protein levels following HCMV infection in fibroblasts, as compared with mock-infected cells.

This experiment was performed to determine the effects of HCMV infection on IRS-1 protein levels. Fibroblasts were infected with HCMV (MOI=1). Cell pellets were collected at 24, 48, 72 and 96 hours post infection and lysed. Western blot was performed using an anti-IRS-1 antibody (Upstate Biothechnology), the results of which are shown in FIG. 8A. Actin is shown in FIG. 8A as a loading control. IRS-1 protein levels were normalized to actin and then compared to the mock-infected IRS-1 levels at each time point. These results show an upregulation in the IRS-1 protein levels at 72 and 96 hpi in the cells infected with HCMV. These data indicate that HCMV is upregulating expression of IRS-1 protein, likely by downregulating expression of miR145. These findings implicate overexpression of IRS-1 in HCMV pathogenesis.

Figure 8B:
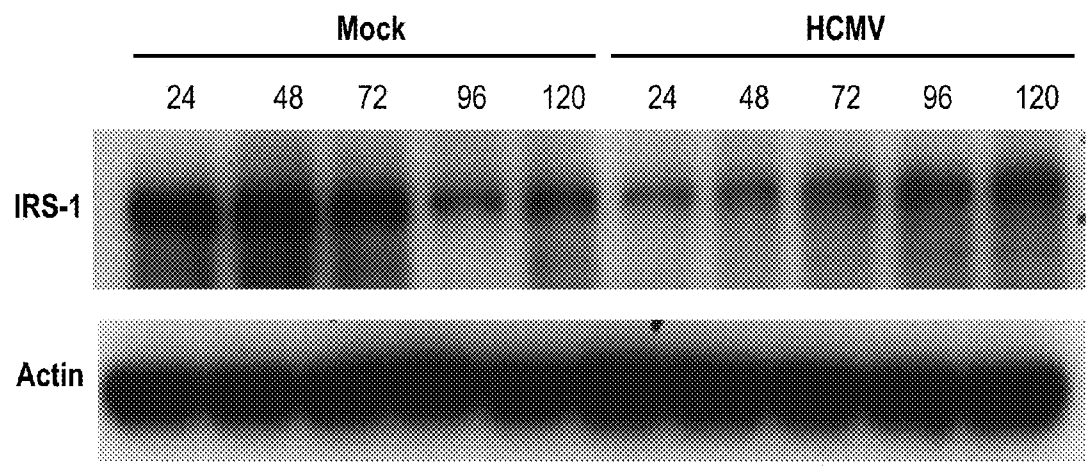

An extended time course was performed to determine the levels of IRS-1 protein during HCMV infection from 24-120 hours. HEL fibroblasts were infected with HCMV (MOI=1) or mock-infected, as a control. This FIG. 8B shows that IRS-1 levels decreased in the uninfected cell time course. However, a gradual increase in the expression of this protein was observed during HCMV infection, starting at 72 hpi (hours post infection). Actin is shown as a loading control. These results suggest that HCMV infection induces IRS-1 upregulation in Hel fibroblasts.

Example 6: IRS-1 is Relocalized During HCMV Infection

Figures 9, 10A, 10B:
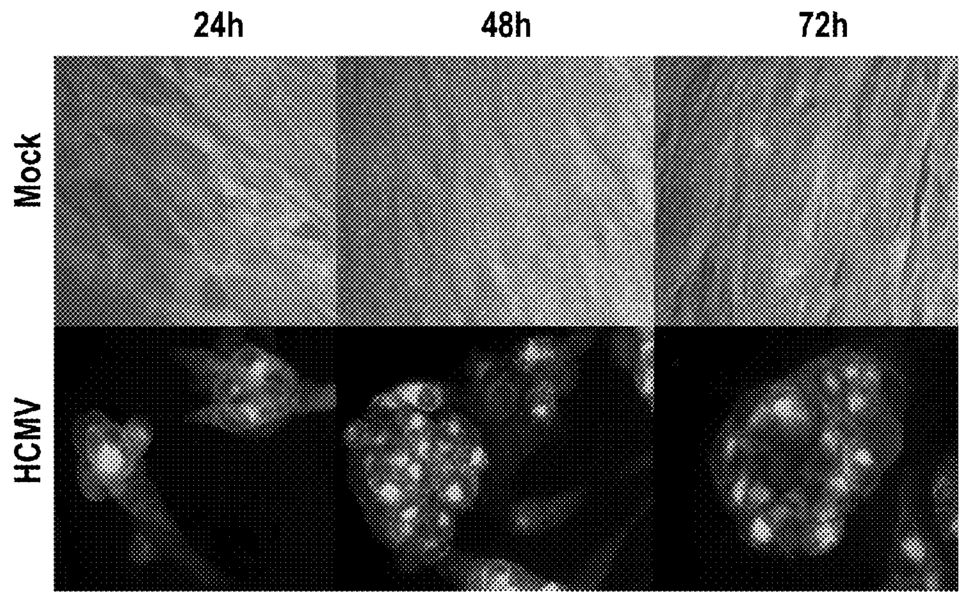
FIG. 9 depicts the re-localization of IRS-1 protein during HCMV infection in HEL fibroblasts, as compared with mock-infected cells.
FIG. 10A depicts the nucleic acid sequence and structure of the mature stem-loop form of miR145 (hsa-miR-145; SEQ ID NO:1).
FIG. 10B depicts the nucleic acid sequence of the mature (processed) form of miR145 (hsa-miR-145; SEQ ID NO:2).

IRS-1 is known to translocate to the plasma membrane after insulin-mediated stimulation of the insulin receptor (Jacobs et al. 2001). This experiment was performed to determine whether IRS-1 is differentially localized after HCMV infection. HEL fibroblasts were grown on coverslips and were either mock infected or infected with HCMV (MOI=1). Cells were fixed at 24, 48 and 72 hpi and stained with primary antibodies against IRS-1, a fluorescein (FITC)-conjugated secondary antibody (green fluorescence), and 4',6-diamidino-2-phenylindole (DAPI, blue fluorescence), for nuclei staining. The fluorescence signal intensity relocalized after HCMV infection when compared to the mock infection, as shown in FIG. 9. These results indicate that a differential localization of IRS-1 occurs during HCMV infection, and that this virus may be altering the distribution of IRS-1 throughout the cell.

Example 7: miR132 is Upregulated Following HCMV Infection

Figure 11:
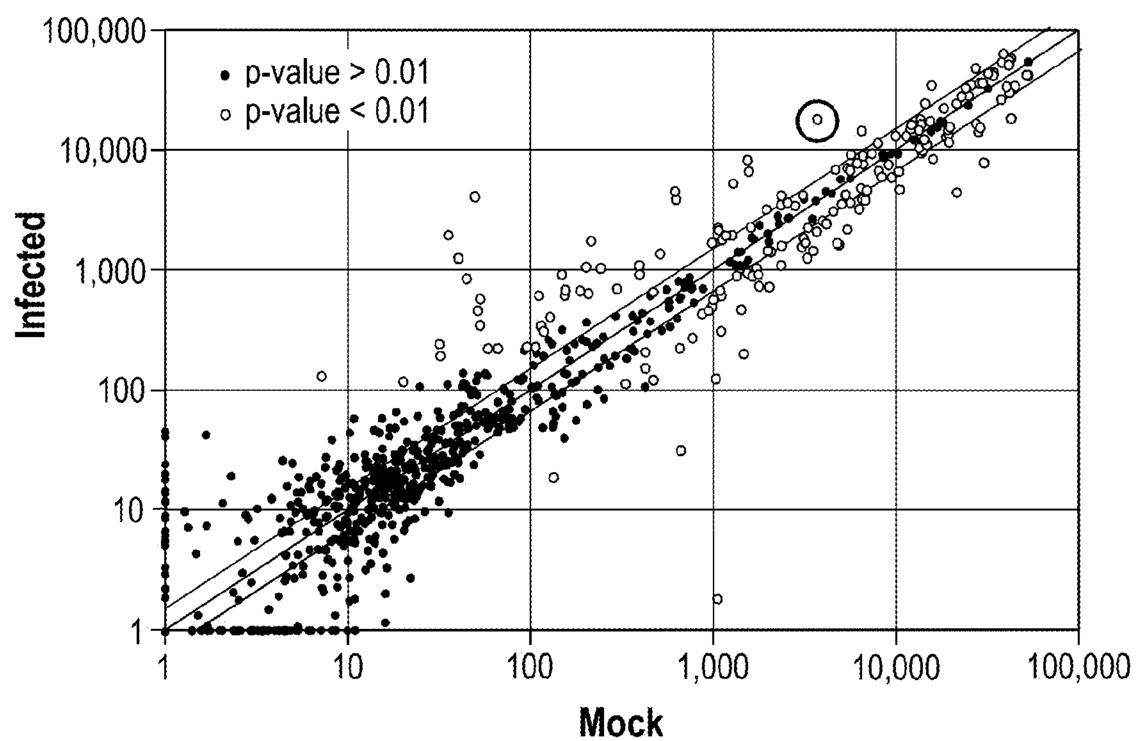
FIG. 11 graphically depicts the alteration in miR132 expression following HCMV infection in HEL fibroblasts, as determined by microarray analysis.

Microarray analysis was performed to determine changes in miRNA expression patterns after HCMV infection. HEL fibroblasts were infected with HCMV (Multiplicity of infection (MOI)=5). RNA from mock-infected cells, together with RNA from cells infected with HCMV (48 hours post infection (hpi)), were hybridized to miRNA microarrays (LC Sciences). Hybridization signal intensities for individual miRNAs (average of six replicates) were plotted as mock versus virus-infected. Statistical analysis was performed at LC Sciences, and an additional Golub analysis was performed for maximum confidence. The results of the microarray analysis are depicted in FIG. 11. Red dots indicate statistically significant values ($p<0.01$). Greater than two-fold changes in miRNA expression appear outside of the diagonal lines. The arrow indicates that miR132 is significantly upregulated following HCMV infection (5 fold increase). These data suggest that miR132 is involved in the pathogenesis of HCMV. The absence of a uni-directional trend in miRNA expression during virus infection suggests that the virus is specifically impacting the expression of particular miRNAs to control the expression of genes required for efficient virus replication.

Figure 12:
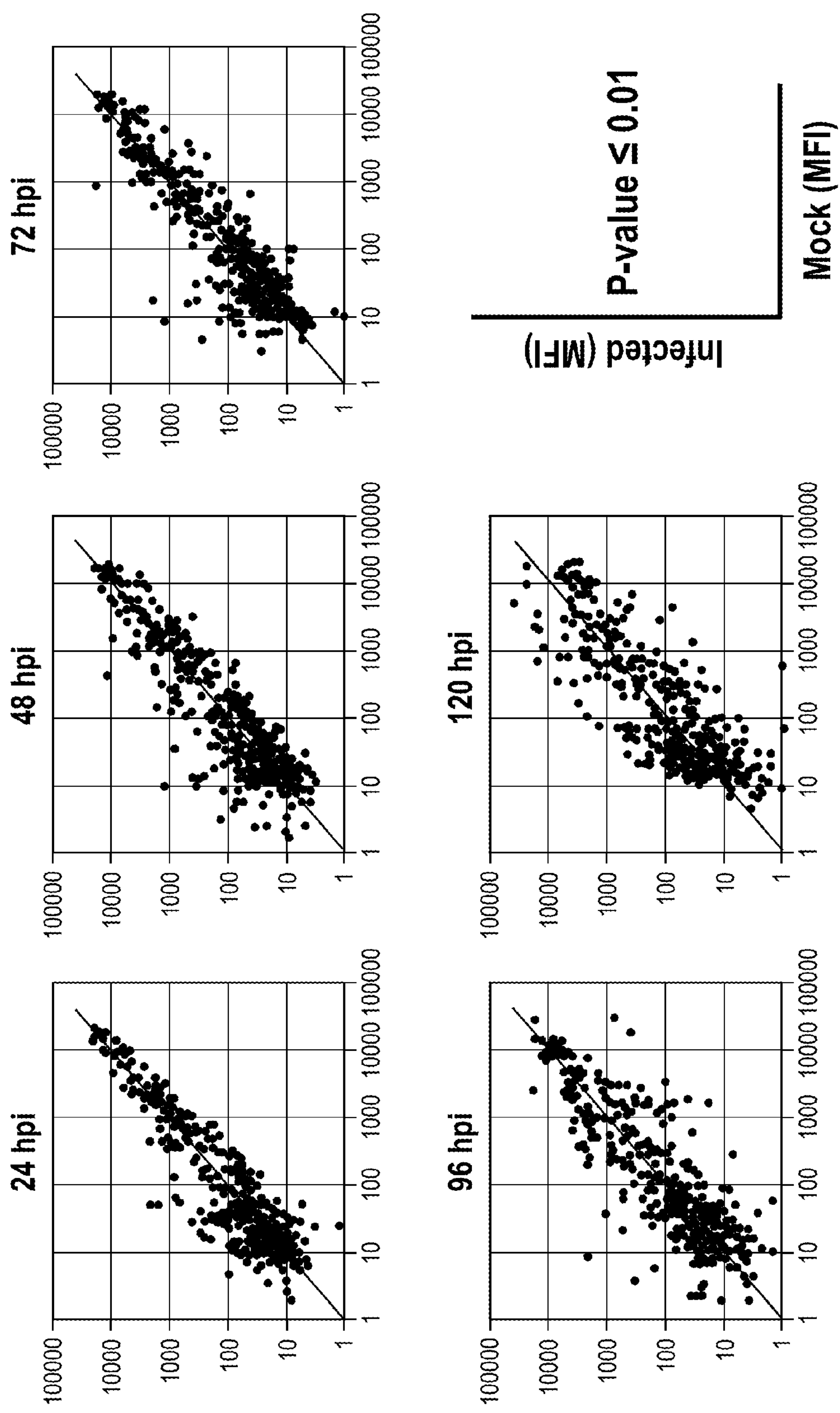
FIG. 12 depicts the differential impact on the expression of cellular miRNAs that occurs during HCMV infection (24-120 hours post-infection).
Figure 13:
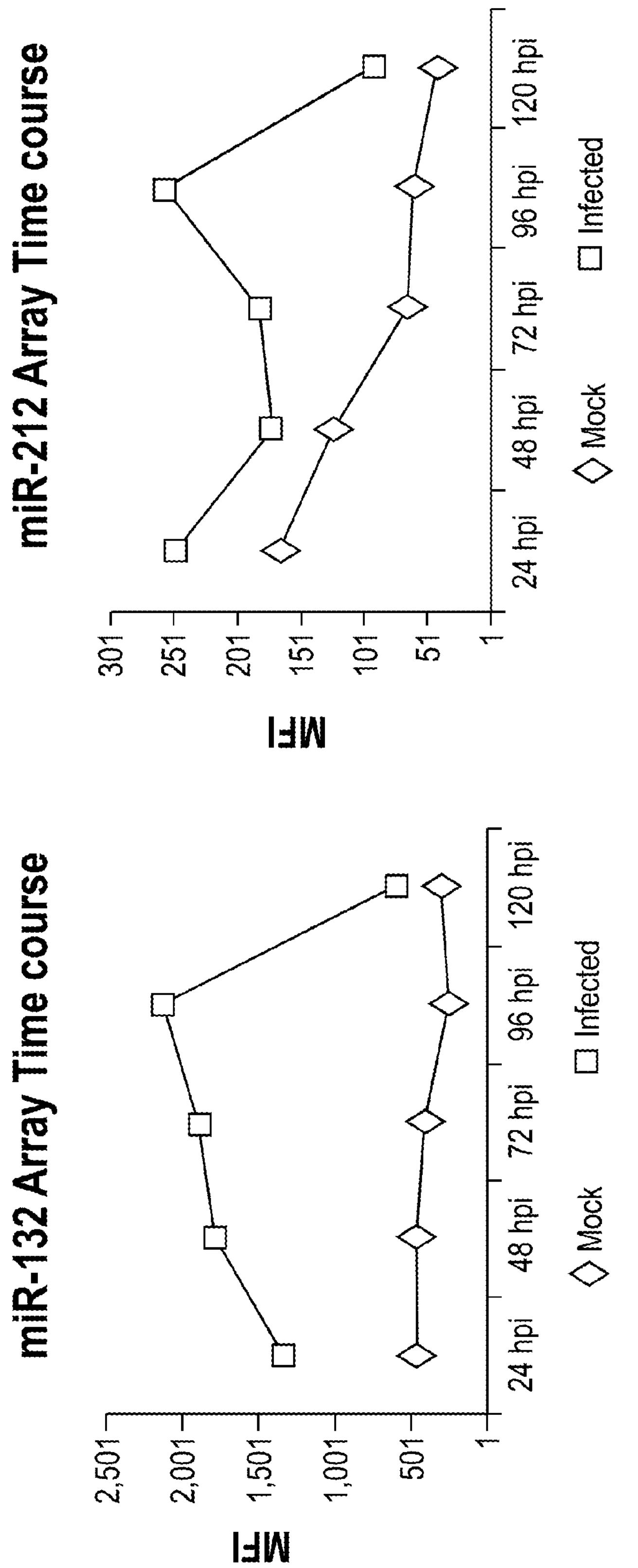
FIG. 13 graphically depicts the relative levels of miR132 and miR212 during HCMV infection between 24-120 hours post-infection.
Figure 14A:
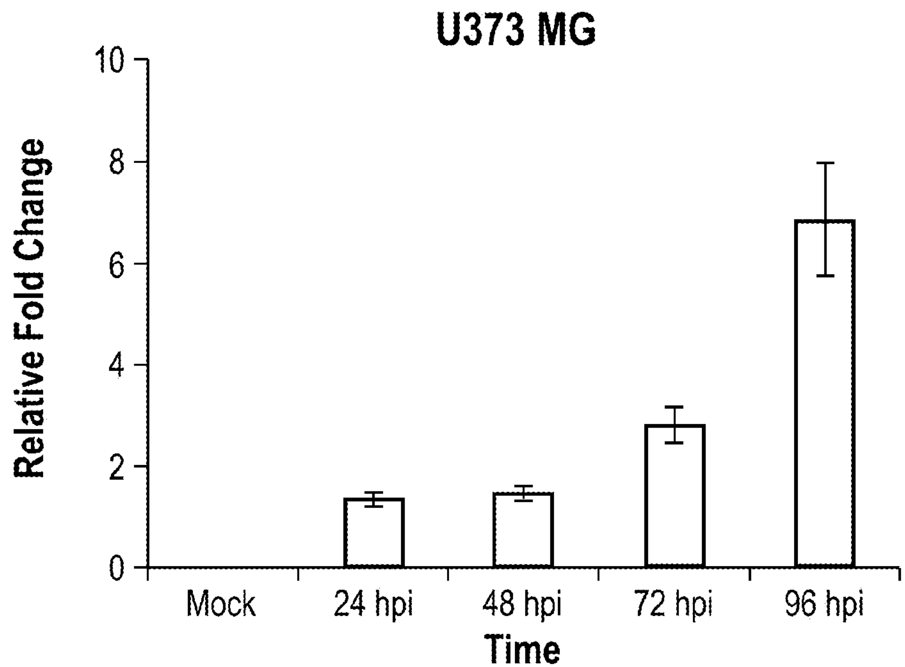
FIG. 14A-FIG. 14B depict miR132 upregulation in HEL fibroblasts and U373 MG glioblastoma-astrocytoma cells at 24, 48, 72, and 96 hours post-infection with HCMV, as determined by quantitative Real Time PCR (qRT-PCR).
Figure 14B:
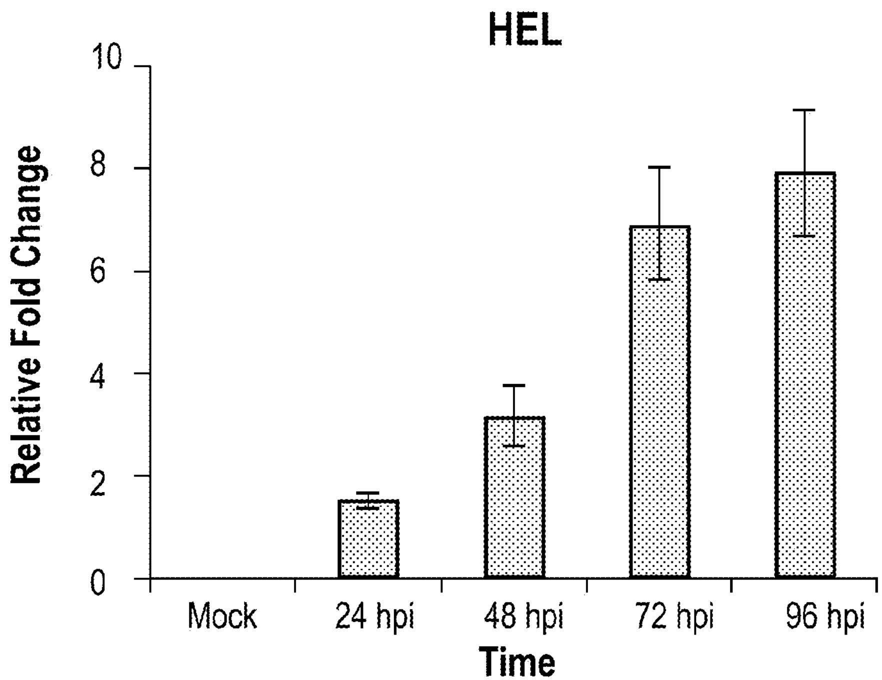

A microarray time course was performed to determine changes in miRNA expression patterns at multiple time points post-infection. HEL cells were either mock or infected with HCMV at an MOI=5, and RNA was extracted with Trizol® (Invitrogen) at the time points indicated in FIG. 12. RNA was hybridized to a microarray (LC Sciences) that harbored probes to all known cellular and viral miRNAs, and the expression of each miRNA was determined by relative quantitation at the respective mock and infected time-points. An ANOVA analysis of variance was used to determine the statistical significance of the change in expression of each miRNA. Results are shown in FIG. 12. Extrapolation of the data corresponding to miR132 and miR212 from the plots shown in FIG. 12 allowed visualization of the expression of miR132 and miR122 over the time course of infection, based on the changes in mean fluorescence intensity (MFI) from the respective mock and infected time points (FIG. 13).

miR132 upregulation during HCMV infection was confirmed by quantitative Real Time PCR (qRT-PCR). Total RNA purified from HEL fibroblasts and U373MG glioblastoma-astrocytoma cells infected with HCMV (MOI=1) was used for Taqman qRT-PCR (Applied Biosystems). Expression of miR132 was normalized to GAPDH. This data, as shown in FIG. 14, validates the >5-fold increase in miR132 expression observed using miRNA microarray, and indicates that HCMV infection results in upregulation of miR132 expression. This phenomenon is further supported by the observation that miR132 expression is similarly regulated in multiple permissive cell lines during infection.

Figure 15:
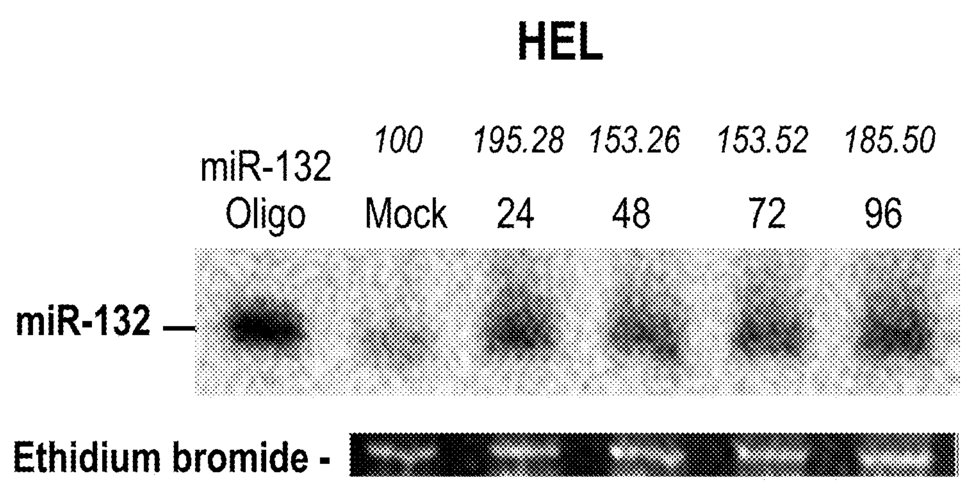
FIG. 15 depicts the expression level of miR132 in HEL fibroblasts at 24, 48, 72, and 96 hours post-infection with HCMV, as determined by Northern Blot.

The observation that miR132 expression increases during HCMV infection was confirmed by Northern blot. Total RNA purified from HEL fibroblasts and U373MG glioblastoma-astrocytoma cells infected with HCMV (MOI=1) analyzed by Northern Blot. The expression of miR132 was quantitated relative to ethidium bromide staining, shown as a loading control. The results depicted in FIG. 15 validate the observation that HCMV infection results in the upregulation of miR132 expression. The effect seen in U373 cells is less dramatic than that seen in HEL cells, likely due to the fact that there is less mature miR132 natively present in this cell line (data not shown).

Figure 16:
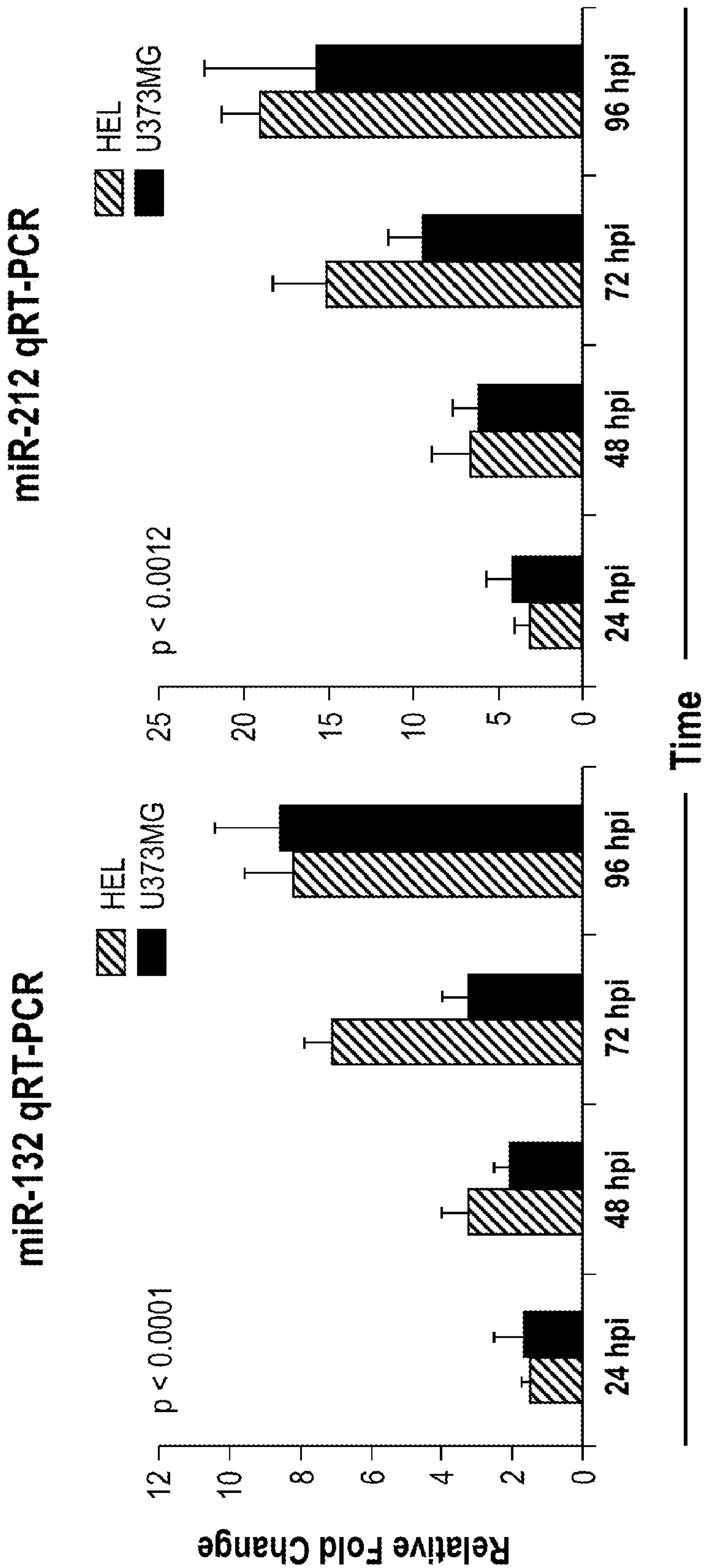
FIG. 16 depicts the relative fold change in miR132 and miR212 expression at 24 hour intervals during HCMV infection, as determined by TaqMan miRNA assay.

TaqMan miRNA assay (Applied Biosystems) further confirmed that miR132 expression was upregulated during HCMV infection, and also indicated that miR212 is upregulated in HEL and U373MG cells during HCMV infection. HEL and U373MG cells were infected with HCMV at MOI=1, and cells were harvested at 24 hour intervals. RNA was then purified from infected cells using Trizol® (Invitrogen) according to the manufacturers protocol, and 5 ng of RNA was used to generate cDNA via reverse transcription. miRNA expression was quantitated using TaqMan® miRNA assay (Applied Biosystems). The histograms in FIG. 16 show the increase in expression of miR-132 and miR-212 relative to GAPDH.

Example 8: HCMV Infection Reduces Expression of MeCP2

Figure 17A:
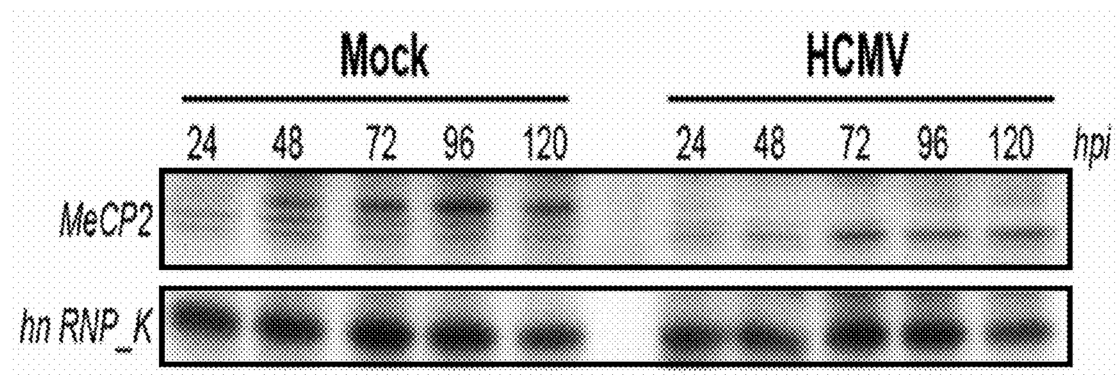
FIG. 17A depicts downregulation of the miR132 and miR212 target MeCP2 in HEL fibroblasts following HCMV infection.
Figure 17B:
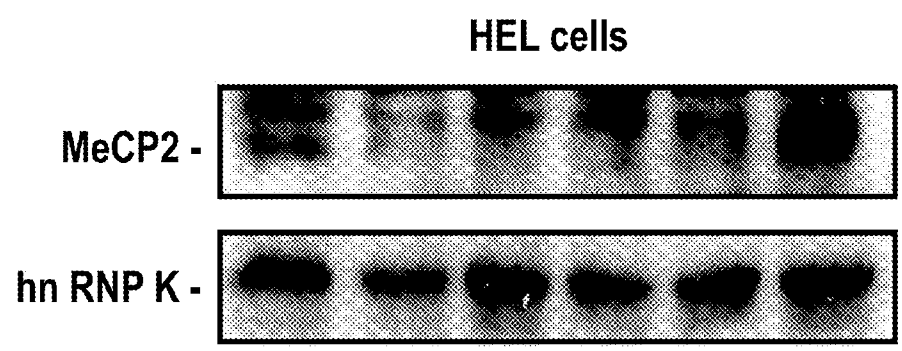
FIG. 17B depicts downregulation of the miR132 target MeCP2 in HEL fibroblasts following HCMV infection.

To determine whether targets of miR-132 were altered during HCMV infection, lysates were prepared at 24 hour intervals from HEL and U373 MG cells infected with HCMV at an MOI=1, or mock infected. Nuclear enriched lysates were prepared and 100 μg of protein lysate was separated by SDS-PAGE. Protein was transferred to PVDF membrane, and MeCP2 and hn RNP_K proteins were detected by Western blot using polyclonal antibodies (Millipore and Santa Cruz). As expected, a decrease in MeCP2 protein levels was observed in HCMV-infected HEL cells (FIG. 17) and U373MG cells (data not shown). These results are consistent with the increase in miR132 and miR212 expression that occurs during HCMV infection. hnRNPK expression is show as a loading control.

Figure 18A:
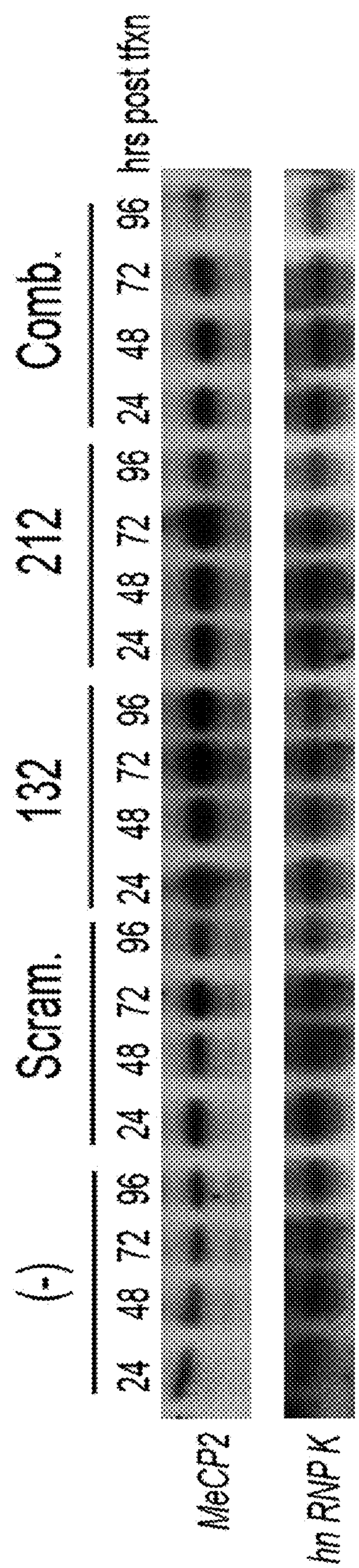
FIG. 18A-FIG. 18B depict the increase in levels of the miR132 and miR212 target MeCP2 that occurs in HEL fibroblasts following treatment with an antisense locked nucleic acid (LNA) targeting miR132 (a-b) or miR212 (a).
Figure 18B:
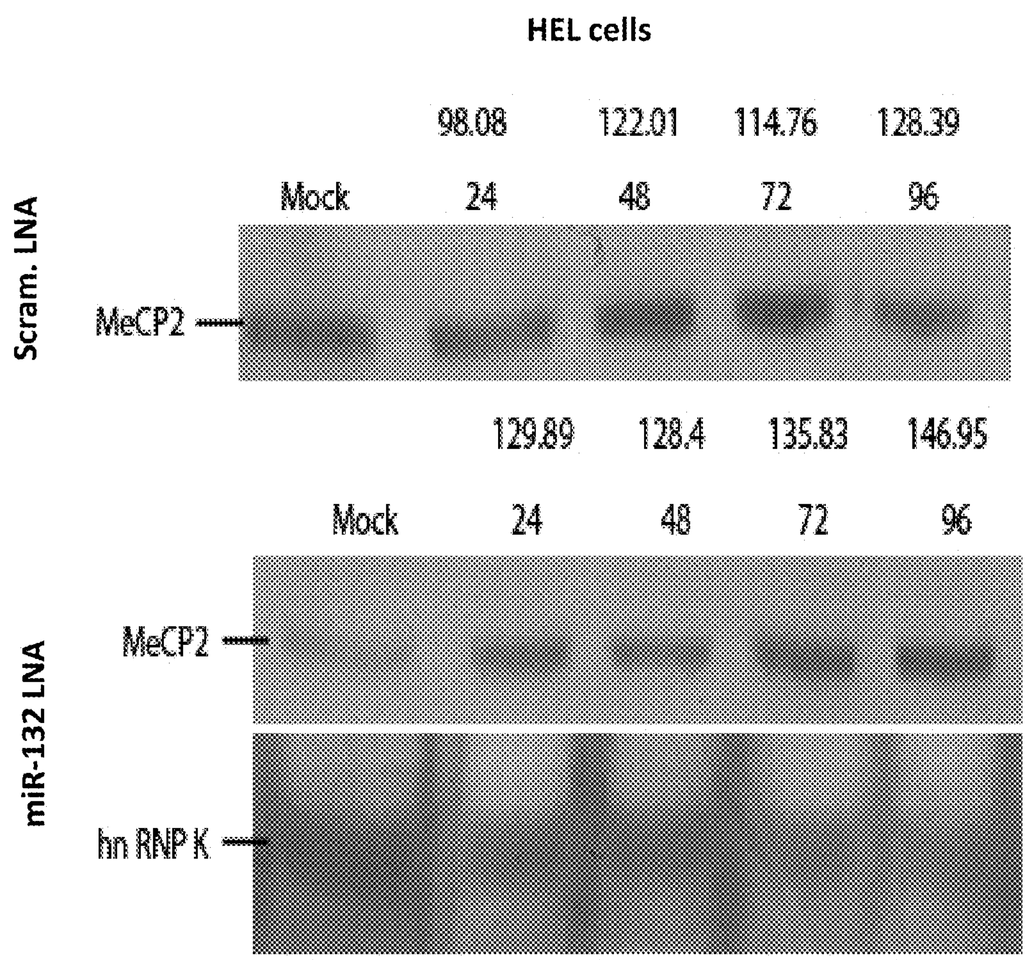

Example 9: Transfection with a miR132 Antagonist or a miR212 Antagonist Increases MeCP2 Protein Accumulation In order to assess the role of miR132 and miR212 in virus replication, miR132 and miR212 were inhibited using antisense locked nucleic acid (LNA) oligonucleotides targeting miR132 or miR212 Inhibition of miR132 and/or miR212 in this way counteracts the increase in miR132 or miR212 expression that occurs during HCMV infection. To test the efficacy of the LNAs, HEL cells were transfected with 500 pmol of scramble, miR132, or miR212 specific locked nucleic acid (Exiqon) to inhibit miRNA function. Nuclear enriched extracts were prepared, and protein levels were determined by Western blot. Transfection with miR132 LNA resulted in a modest increase in MeCP2 protein levels in HEL cells (FIG. 18*a*-*b*), demonstrating that a miR132 antagonist can be used to increase expression of a miR132 target. Likewise, transfection with miR212 LNA resulted in a modest increase in MeCP2 protein levels in HEL cells (FIG. 18*a*), demonstrating that a miR212 antagonist can be used to increase expression of a miR212 target.

Figure 19:
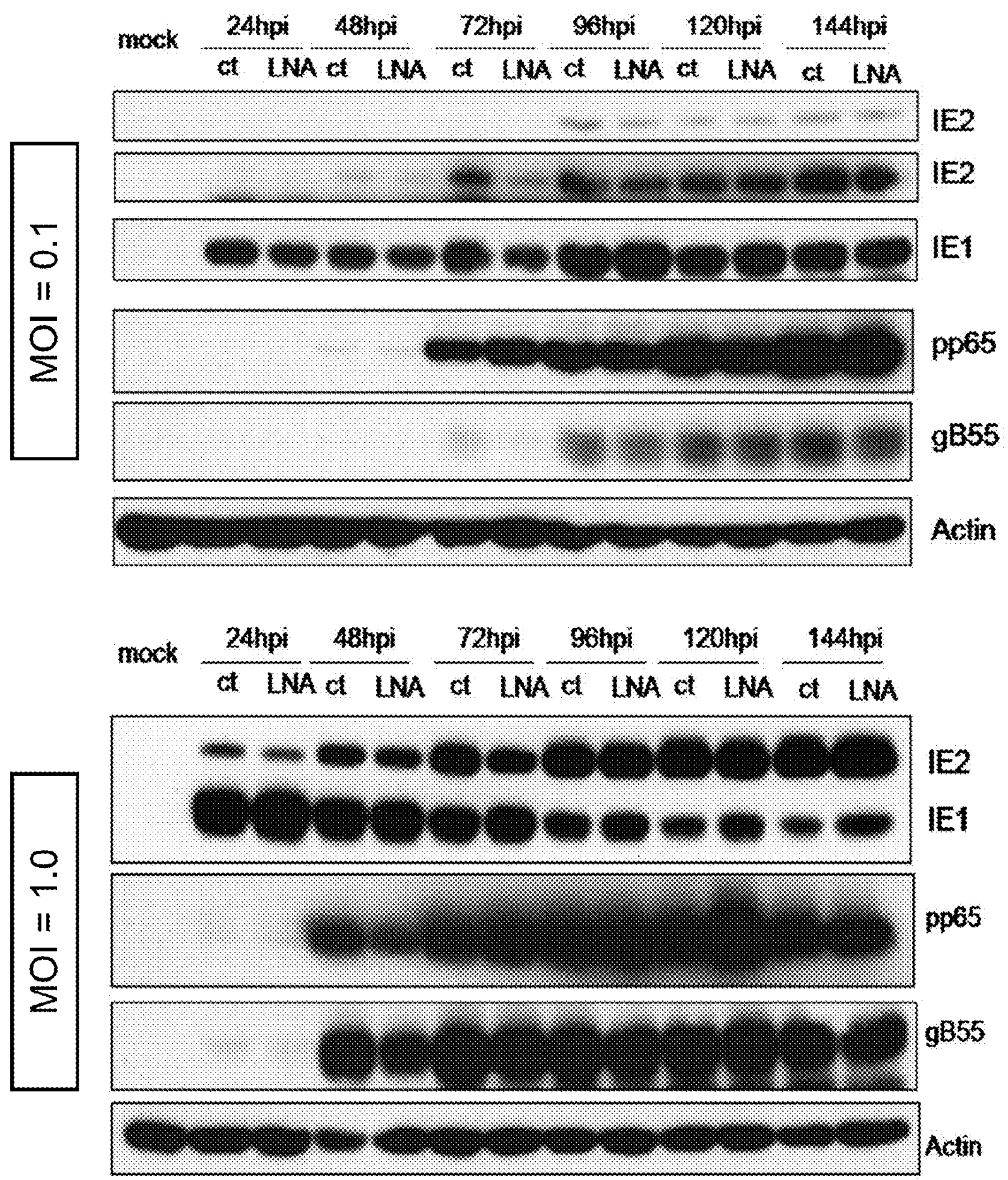
FIG. 19 depicts the reduction in expression of the HCMV proteins IE2, pp65, and gB55 that occurs in HEL fibroblasts previously transfected with an antisense miR132 LNA at 24, 48, 72, 96, 120, and 144 hours post-infection with HCMV, as compared to cells transfected with a control LNA (ct).

Example 10: Inhibition of miR132 with a miR132 Antagonist Attenuates HCMV Replication To determine the role of miR132 on HCMV replication, HEL cells were transfected with antisense miR132 LNA, and were infected with HCMV. The amount of virus released from infected cells was quantitated by plaque assay, and viral protein accumulation was analyzed by Western blot of protein lysates from infected cells. As shown in FIG. 19, expression of viral proteins IE2, pp65, and gB55 was reduced in cells transfected with an antisense miR132 LNA Inhibition of miR132 resulted in a 3-fold decrease in virus replication, as determined by measuring attenuated virus release and viral protein expression. Taken together with the previous data, this experiment confirms that miR132 is necessary for efficient HCMV replication, and that HCMV replication can be effectively attenuated by inhibition of miR132.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed:

1. A method of inhibiting HCMV replication in a cell, comprising contacting the cell with a miR212 antagonist in an amount effective to increase the level of one or more miR212 targets, wherein the miR212 antagonist is selected from the group consisting of an antisense locked nucleic acid (LNA) targeting miR212, an antagomir targeting miR212, or a 2'O-methyl antisense RNA targeting miR212, such that HCMV replication is inhibited.

2. The method of claim 1, wherein the level of one or more targets is determined by measuring the level of expression of a polypeptide encoded by the target, and comparing the level of expression to a suitable control.

3. The method of claim 2, wherein measuring the level of expression of a polypeptide encoded by the target is performed using a method selected from the group consisting of Western blot, ELISA, or antibody microarray.

4. The method of claim 1, wherein the level of one or more targets is determined by measuring the level of expression of an mRNA corresponding to the target, and comparing the level of expression to a suitable control.

5. The method of claim 4, wherein measuring the level of expression of an mRNA corresponding to the target is performed using a method selected from the group consisting of Northern blot, quantitative Real Time PCR (qRT-PCR), or microarray.

6. The method of claim 1, wherein the miR212 target is a nucleic acid molecule having sequence complementarity with all or a portion of SEQ ID NO:5 or SEQ ID NO:6.

7. The method of claim 1, wherein the miR212 target is a nucleic acid molecule containing a region of 6-8 contiguous nucleotides that are complementary to the seed region of miR212.

8. The method of claim 7, wherein the 6-8 contiguous nucleotides are located within the 3'UTR of the miR212 target.

9. The method of claim 7, wherein the 6-8 contiguous nucleotides are located within an open reading frame of the miR212 target.

10. The method of claim 1, wherein the miR212 target is a nucleic acid molecule encoding methyl CpG-binding protein 2 (MeCP2).

11. The method of claim 1, wherein the miR212 target is a nucleic acid molecule encoding Rho GTPase-activating protein (RICS).

12. The method of claim 1, wherein the miR212 antagonist comprises a nucleic acid molecule that is complementary to all or a portion of SEQ ID NO:5 or SEQ ID NO:6.

13. The method of claim 1, wherein the cell is in an organism.

14. The method of claim 1, further comprising contacting the cell with an additional therapeutic agent.

15. The method of claim 14, wherein the additional therapeutic agent is an antiviral agent.

16. The method of claim 15, wherein the antiviral agent is selected from the group consisting of Ganciclovir, Valganciclovir, Cidofovir, Foscarnet, Formivirsen, Acyclovir, Valacyclovir, CMX001, Artesunate, BAY-384766, T-611, GW-275175X, and Maribavir.

17. A method of inhibiting HCMV replication in a cell, comprising contacting the cell with a miR212 antagonist in an amount effective to increase the level of one or more miR212 targets, wherein the miR212 antagonist comprises a nucleic acid molecule that is complementary to all or a portion of SEQ ID NO:5 or SEQ ID NO:6.

18. The method of claim 17, wherein the nucleic acid molecule comprises one or more modified nucleotides, wherein the modified nucleotides comprise a modification selected from the group consisting of 2'-O-methyl (2'-OMe), 2'-O-methoxyethyl (2'-MOE), and 2'-fluoro (2'F).

19. The method of claim 17, wherein the nucleic acid molecule comprises one or more phosphorothioate modifications.

20. The method of claim 17, wherein the miR212 target has a region of 6-8 contiguous nucleotides that are complementary to the seed region of miR212.

21. The method of claim 20, wherein the 6-8 contiguous nucleotides are located within the 3'UTR of the miR212 target, or within an open reading frame of the miR212 target.

22. The method of claim 17, wherein the miR212 target is an mRNA encoding MeCP2, or an mRNA encoding RICS.

23. The method of claim 17, wherein the cell is in an organism.

24. The method of claim 17, further comprising contacting the cell with an additional therapeutic agent.

25. The method of claim 24, wherein the additional therapeutic agent is an antiviral agent.

26. The method of claim 25, wherein the antiviral agent is selected from the group consisting of Ganciclovir, Valganciclovir, Cidofovir, Foscarnet, Formivirsen, Acyclovir, Valacyclovir, CMX001, Artesunate, BAY-384766, T-611, GW-275175X, and Maribavir.

* * * * *